US008892481B2

(12) United States Patent
Landers

(10) Patent No.: US 8,892,481 B2
(45) Date of Patent: Nov. 18, 2014

(54) HEALTH AND FITNESS MANAGEMENT SYSTEM

(71) Applicant: Kinetic Stone, LLC, Edgewater, NJ (US)

(72) Inventor: David B. Landers, Edgewater, NJ (US)

(73) Assignee: Kinetic Stone, LLC, Edgewater, NJ (US)

( * ) Notice: Subject to any disclaimer, the term of this patent is extended or adjusted under 35 U.S.C. 154(b) by 0 days.

(21) Appl. No.: 14/282,918

(22) Filed: May 20, 2014

(65) Prior Publication Data

US 2014/0258208 A1     Sep. 11, 2014

Related U.S. Application Data

(63) Continuation-in-part of application No. 13/743,718, filed on Jan. 17, 2013.

(51) Int. Cl.
    *G06F 15/18*      (2006.01)
    *G06N 5/04*      (2006.01)

(52) U.S. Cl.
    CPC ...................................... *G06N 5/048* (2013.01)

USPC .............. 706/12; 600/587; 600/300; 600/316

(58) Field of Classification Search
None
See application file for complete search history.

(56) References Cited

U.S. PATENT DOCUMENTS

| | | | | |
|---|---|---|---|---|
| 6,635,015 B2* | 10/2003 | Sagel | ............................. | 600/300 |
| 2002/0107433 A1* | 8/2002 | Mault | ........................... | 600/300 |
| 2003/0208113 A1* | 11/2003 | Mault et al. | .................... | 600/316 |
| 2011/0087137 A1* | 4/2011 | Hanoun | ........................ | 600/587 |

* cited by examiner

*Primary Examiner* — Kakali Chaki
*Assistant Examiner* — Luis Sitiriche
(74) *Attorney, Agent, or Firm* — Beverly W. Lubit

(57) ABSTRACT

A health and fitness management system is provided that has a health and fitness application operating, e.g., on a smart phone, that can wirelessly communicate with an activity module worn on the user which has a motion sensor, e.g., an accelerometer. The application accepts food and weight inputs (e.g., from the smart phone) and user activity units (e.g., from the activity unit) and develops a user intrinsic metabolism. The application includes fitness arc and health quotient graphical indicators that guide the user on health and fitness activities.

28 Claims, 37 Drawing Sheets

Today's food intake has exceeded the amount necessary to maintain fitness.

HEALTH AND FITNESS MANAGEMENT SYSTEM

CROSS-REFERENCES TO RELATED APPLICATION

The present application is a continuation-in-part of U.S. patent application Ser. No. 13/743,718, filed Jan. 17, 2013, which claims the benefit of priority to U.S. patent application Ser. No. 13/036,151, filed Feb. 28, 2011, the disclosures of which are incorporated herein by reference in their entirety.

FIELD

The disclosed subject matter relates to a health management system, and to a system for managing the health and fitness of an individual.

BACKGROUND

Counting calories can be an inherently inaccurate process and cannot be successfully used to predict weight loss because food items and physical activity can be subject to wide variation, such as in relation to actual calories ingested or burned, e.g., from individual to individual, over time through life and even on a daily basis. Conventional weight loss programs often require the user to track food intake, which may be subjective. For example, one person's serving size for a particular food item may be different from another person's serving size. Moreover, weighing and measuring food items may be difficult to accomplish, and also difficult to do consistently over a course of a weight loss algorithm. In addition, tracking calories burned may be difficult, as the number of calories burned may vary from exercise to exercise and person to person.

As can be seen, for these and other reasons, there is a need for a more comprehensive health management system that is simple to use (i.e., to input food consumption and physical activity information), and that may adapt to an individual's particular and often changing response to certain food intake and exercise. Beneficially, such a system should also output metabolically related health parameters such as weight gain/loss, food quality, fluids intake and condition, salt intake and levels, percentage of vitamin rich foods, and, in addition, provide an overall health and fitness measurement that can be simply and readily understandable.

SUMMARY

The method for instantaneously and continuously assessing real time energy balance for fitness management of the described invention comprises, in order: (a) collecting food intake information for actual or expected food intake of a user over a specified period of time and contemporaneously converting the food intake information into food intake energy units for the first period of time, wherein the food intake units are based on relative energy content of one food compared to another without relying on standard caloric values; (b) collecting by a device activity information for actual or expected activity by the user over the specified period of time and contemporaneously converting the activity information into energy units for the user for the first period of time, wherein the collecting for actual activity is achieved by wireless transmission by a motion sensor and the motion sensor is a programmable accelerometer, the functional status of which is altered by: (i) positioning the accelerometer inside an engineered magnetic environment; (ii) collecting deflections of the accelerometer during the activity in various positions inside the engineered environment such that it records motion associated with one type of activity while excluding movement characteristic of another form of activity; (iii) applying a multiplier to the accelerometer deflections collected in (ii) to assign a weighted value indicative of the level of effort exerted during the activity; (iv) saving deflections from each type of movement such that deflection counts are segregated by activity type and determining the amount of relative energy expended by the user during any given time period in the activity type; (v) transferring deflection counts and relative energy expended to a device; and (vi) processing the deflection counts and relative energy expended for display by the device; (c) instantaneously deriving, via a computing device, a calculated currently determined constant that reflects efficiency, which is a rate at which the user extracts energy from the food units that can be referenced against predicted and actual changes in weight, wherein the constant is a surrogate for intrinsic metabolic rate; (d) instantaneously calculating by an algorithm from the calculated currently determined constant in (c) a predicted energy balance for the user, by: 1. calculating a ratio of an amount of activity units expected divided by an amount of activity observed; 2. calculating a ratio of an amount of food units expected divided by an amount of food units observed; 3. weighting the ratio in (a) against the ratio in (b) according to goals of the user; and 4. modifying the weighted ratio in (iii) by a rate at which the user performs the activity/work; (e) instantaneously predicting a change in weight from the predicted energy balance; and (f) determining fitness level of the user based on the efficiency of energy consumption.

According to one embodiment, the change in weight is displayable either as a numeric weight or as a colored dot display system. According to another embodiment, the colored dot display system comprises: (a) a red dot representing weight gain other than muscle; (b) a green dot representing muscle growth or weight loss; and (c) a yellow dot representing no change in fat/muscle ratios.

According to one embodiment, the deflection counts in (d) are segregated by activity type in a processor.

According to one embodiment, positioning the accelerometer inside the engineered magnetic environment initiates a programming change to alter the functional status of the accelerometer into activity monitoring modes. According to another embodiment, the activity monitoring modes are selected from the group consisting of a standard mode (S), a running/jogging mode (A+), a bicycle mode (A), a weight lifting/resistance training/yoga mode (W+), an aerobic-based gym equipment mode (W) and a sleep activity mode. According to another embodiment, the standard mode (S) comprises routine daily activity.

According to one embodiment, the type of activity is selected from the group consisting of aerobic activities and non-aerobic. According to another embodiment, the aerobic activity is selected from the group consisting of walking, jogging, running, biking, tennis, basketball, soccer circuit training and elliptical training. According to another embodiment, the non-aerobic activity is selected from the group consisting of weight lifting, yoga, Pilates and resistance training.

According to one embodiment, the accelerometer is a triaxial accelerometer.

According to one embodiment, the engineered magnetic environment is a magnetic field. According to another embodiment, the magnetic field is created by magnets. According to another embodiment, the magnets are contained within a receptacle. According to another embodiment, the receptacle is pouch. According to another embodiment, the receptacle is a pocket. According to another embodiment, the receptacle is connected to a means for attaching the accelerometer to a user.

According to one embodiment, when the type of activity is sleep, the described invention provides a method for measuring quality of sleep comprising:

(i) assigning a time period in which the user is going to bed; (ii) collecting deflections of the accelerometer during the assigned time period of (i); (iii) transferring the deflection counts collected in (ii) corresponding to sleep activity to a device; (iv) ending the time period assigned in (i); and (v) processing the deflection counts for display by the device, wherein an increase in accelerometer deflections recorded compared to an average of accelerometer deflections recorded is indicative of a sleep disorder.

According to one embodiment, the sleep disorder is selected from the group consisting of sleep apnea, insomnia and restless leg syndrome. According to another embodiment, the sleep disorder is sleep apnea.

According to one embodiment, when the type of activity is sleep, the described invention provides a method for determining an increased physiological benefit during sleep comprising: (i) assigning a time period in which the user is going to bed; (ii) collecting deflections of the motion sensor during the assigned time period of (i); (iii) transferring the deflection counts collected in (ii) corresponding to sleep activity to a device; (iv) ending the time period assigned in (i); and (v) processing the deflection counts for display by the device, wherein no change or a decrease in accelerometer deflections recorded compared to an average of accelerometer deflections recorded is indicative of an increased physiological benefit during sleep.

According to one embodiment, the increased physiological benefit is an increase in interstitial space in brain. According to another embodiment, the increased physiological benefit is an increase in convective exchange of cerebrospinal fluid (CSF) and interstitial fluid (ISF) in brain. According to another embodiment, the increased physiological benefit is an increased rate of clearance form brain of a protein linked to neurodegenerative disease. According to another embodiment, the protein is selected from the group consisting of β-amyloid (Aβ), α-synuclein and tau.

According to one embodiment, the information used to determine weight gain other than muscle, muscle growth or weight loss, or no change in fat/muscle ratios, is integrated into multiple parameters that form a health quotient displayed by the device as a single point on a scale ranging from fit to healthy to unhealthy to at risk.

According to another aspect, the described invention provides a machine readable medium storing instructions that, when executed by a computing device, cause the computing device to perform a method for instantaneously and continuously assessing real time energy balance for fitness management, comprising: (a) collecting food intake information for actual or expected food intake of a user over a specified period of time and contemporaneously converting the food intake information into food intake energy units for the specified period of time, wherein the food intake units are based on relative energy content of one food compared to another without relying on standard caloric values; (b) collecting by a device activity information for actual or expected activity by the user over the specified period of time and contemporaneously converting the activity information into activity energy units for the user for the specified period of time; (c) instantaneously deriving, via a computing device, a calculated currently determined constant that reflects efficiency, which is a rate at which the user extracts energy from the food units that can be referenced against predicted and actual changes in weight, wherein the constant is a surrogate for intrinsic metabolic rate (d) instantaneously calculating by an algorithm from the calculated currently determined constant in (c) a predicted energy balance for the user, by: (i) calculating a ratio of an amount of activity units expected divided by an amount of activity observed; (ii) calculating a ratio of an amount of food units expected divided by an amount of food units observed; (iii) weighting the ratio in (a) against the ratio in (b) according to goals of the user; and (iv) modifying the weighted ratio in (iii) by a rate at which the user performs the activity/work; (e) instantaneously predicting a change in weight from the predicted energy balance; and (f) determining fitness level of the user based on the efficiency of energy consumption.

According to another aspect, the described invention provides a system for instantaneously and continuously assessing real time energy balance for fitness management comprising: a computing device configured to: (a) collect food intake information for actual or expected food intake of a user over a specified period of time and contemporaneously converting the food intake information into food intake units for the specified period of time, wherein the food intake units are based on relative energy content of one food compared to another without relying on standard caloric values; (b) collect by a device activity information for actual or expected activity by the user over the specified period of time and contemporaneously converting the activity information into activity units for the user for the first period of time; (c) instantaneously derive, via a computing device, a calculated currently determined constant that reflects efficiency, which is a rate at which the user extracts energy from the food units that can be referenced against predicted and actual changes in weight, wherein the constant is a surrogate for intrinsic metabolic rate (d) instantaneously calculate by an algorithm from the calculated currently determined constant in (c) a predicted energy balance for the user, by: (i) calculating a ratio of an amount of activity units expected divided by an amount of activity observed; (ii) calculating a ratio of an amount of food units expected divided by an amount of food units observed; (iii) weighting the ratio in (a) against the ratio in (b) according to goals of the user; and (iv) modifying the weighted ratio in (iii) by a rate at which the user performs the activity/work; (e) instantaneously predict a change in weight from the predicted energy; and (f) determine fitness level of the user based on the efficiency of energy consumption.

BRIEF DESCRIPTION OF THE DRAWINGS

For a more complete understanding of the disclosed subject matter, reference can be made to the following detailed description of an exemplary embodiment considered in conjunction with the accompanying drawings, in which.

DETAILED DESCRIPTION OF EXEMPLARY EMBODIMENTS

Figure 1:
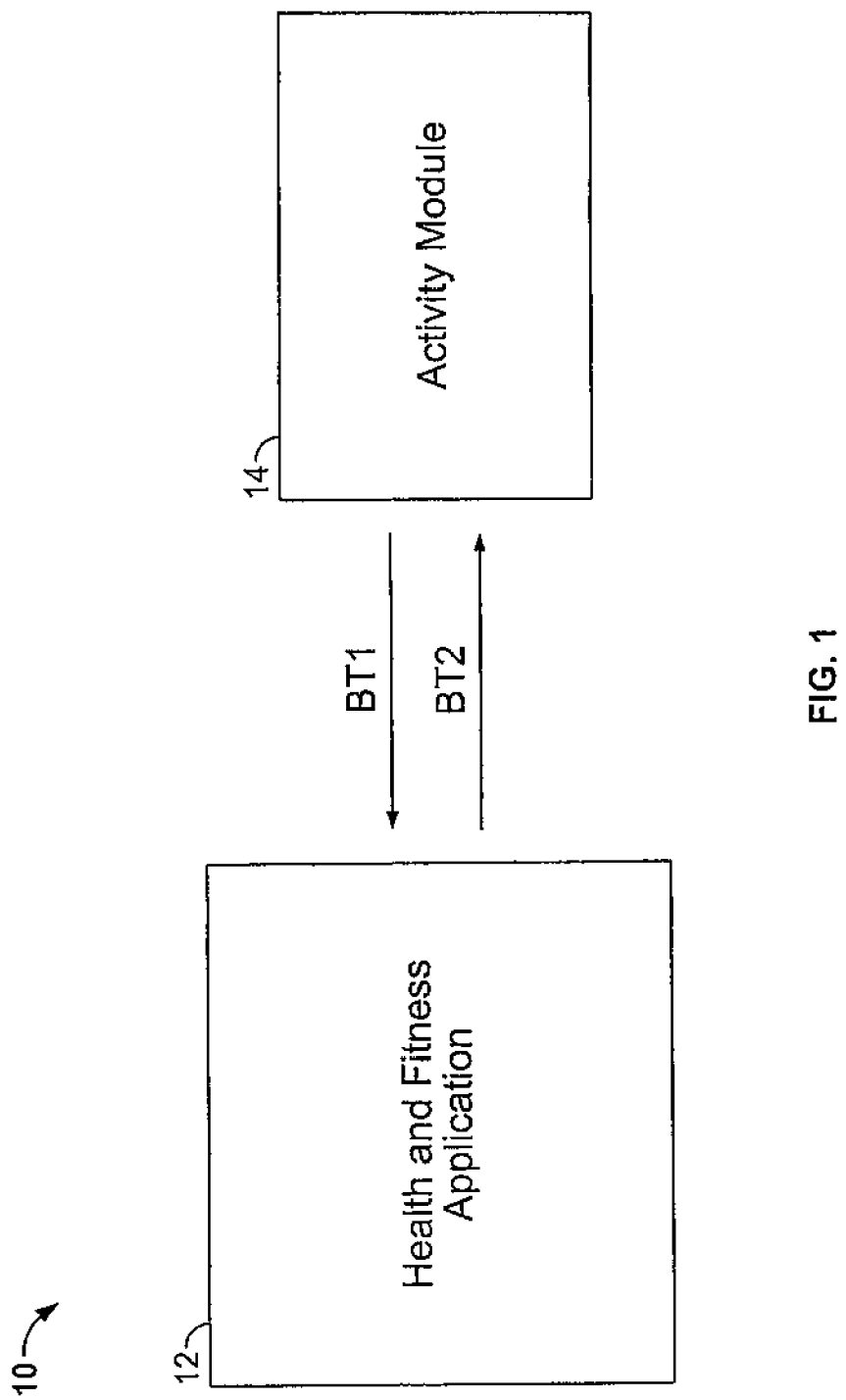
FIG. 1 is a schematic diagram in block diagram form of a health and fitness management system constructed in accordance with an exemplary embodiment of the disclosed subject matter, the system having a health and fitness application operating, e.g., on a smart phone, that can wirelessly communicate with an activity module.

The described invention can be better understood from the following description of exemplary embodiments, taken in conjunction with the accompanying figures and drawings. It should be apparent to those skilled in the art that the described embodiments of the described invention provided herein are merely exemplary and illustrative and not limiting.

DEFINITIONS

Various terms used throughout this specification shall have the definitions set out herein.

The phrase "count minimum" as used herein refers to the number of deflections a motion sensor, e.g., an accelerometer, must sequentially count before the motion sensor, e.g., accelerometer, begins to record deflections. For example, for a count minimum of 20, if an accelerometer counts 15 deflections followed by a silent period of no motion, the accelerometer will not record the 15 deflections.

The phrase "detection time" as used herein refers to the number of events the motion sensor, e.g., accelerometer, is permitted to record per unit time. The range of the detection time may be, for example, in fractions of seconds.

The phrases "engineered magnetic environment" or "engineered environment" as used interchangeably herein refer to a pre-specified position/orientation of the activity module/ motion sensor (i.e., the accelerometer) within a magnetic field.

The phrase "health quotient" as used herein refers to the value assigned to an individual user that represents a measure of health and fitness based on the algorithm of the described invention. The algorithm incorporates, among others, activity amount, types of activity, direction of change in the amounts and types of activity, food amount, types of food, changes in the types of food consumed, the distribution of food intake throughout a day, the number of sleep deflections and the direction in the number of sleep deflections per night, weight and the speed of change in weight, the amount of salt consumed, the number and percentage of vitamins consumed and the amount of fiber consumed. Once a user selects a fitness goal, a health quotient algorithm is calculated for the user. The user is placed on a continuum of the health quotient bar (e.g., fit, healthy, unhealthy, at risk) which changes over time based on the algorithm.

The term "multiplier" as used herein refers to the number by which the recorded motion sensor (e.g., accelerometer) count is multiplied at the processor before being assigned to the algorithm in the activity circle of the activity module application.

The phrase "release time" as used herein refers to the amount of time between two sequential motion sensor (e.g., accelerometer) deflections that is allowed to elapse before the second deflection is considered a new or separate event and thus not part of the same sequence.

The term "sensitivity" as used herein refers to the speed of acceleration required for the motion sensor (e.g., accelerometer) to detect movement.

The disclosed subject matter provides a health management system that includes an application that employs readily identifiable icons to facilitate the input of food consumption information, a motion sensor to autonomously facilitate the input of physical activity information, and the direct input of weight information into the application. The application utilizes the food consumption, physical activity, and weight input information to formulate and periodically adjust a resting or intrinsic metabolism for the user. The system provides instantaneous feedback on the relationship of food items and exercise to one's fitness level, including one's weight. The system does not require the user to count calories, either on the intake or expenditure side of the weight management paradigm. Rather, the system employs icons and graphic displays, without units, to provide a user-friendly interface. The health management system can also integrate weight, food intake and physical activity and can learn the individual's unique response to each element to predict the direction of weight gain or loss.

In an embodiment, the system includes a digital device such as a smart cell phone or tablet device which, for example, may employ an Android operating system. The device runs a software application including algorithm code adapted to i) receive an input corresponding to the calories consumed by the user via a graphical representation of the food portion that can be graphically adjusted by the user, ii) receive an input corresponding to physical activity of the user via wireless transmissions by a motion sensor worn by the user, and iii) receive an input corresponding to weight of the user via direct input by the user. The application predicts the user's fitness level and intrinsic metabolism based on the input corresponding to calories consumed and the calculation of calories burned due to activity, and adjusts the user's fitness level prediction based on historic measurements of the calories consumed, the calories burned, and the weight of the user. The application also uses the data to predict what can happen to the user's weight based upon the real time assessment of caloric needs. The application provides graphics which can be updated at predetermined intervals, such as every ten minutes, to reveal fitness parameters including the user's daily overall energy balance.

There can be, by way of example, four components or parameters that can be used by an algorithm in the system. Briefly, the components can be calories consumed, calories burned through activity (e.g., exercise), weight, and the calories necessary to maintain basic physiologic function or intrinsic metabolism. If three of these parameters can be known, then the fourth can be derived via an energy balance calculation. Therefore, formulating the intrinsic metabolism requires registering the calories consumed, and monitoring and assigning caloric value to physical activities. The energy balance calculation is disclosed in greater detail hereinafter.

FIG. 1 illustrates a health management system 10 ("the system") which can be constructed in accordance with an exemplary embodiment of the disclosed subject matter. The system 10 can include a health and fitness application 12 ("the application") and an activity module 14. The application 12 can communicate wirelessly with the activity module 14, e.g., via Bluetooth™ or other ad hoc local wireless node transmission, e.g., over channels BT1 and BT2. The activity module 14 can be worn by the user, for instance when he/she exercises, to measure and wirelessly transmit activity units accumulated during exercise, to the application 12. The application 12 can, by way of example, convert the activity units into calories burned during exercise (i.e., in addition to the calories burned by intrinsic metabolism).

Figure 2:
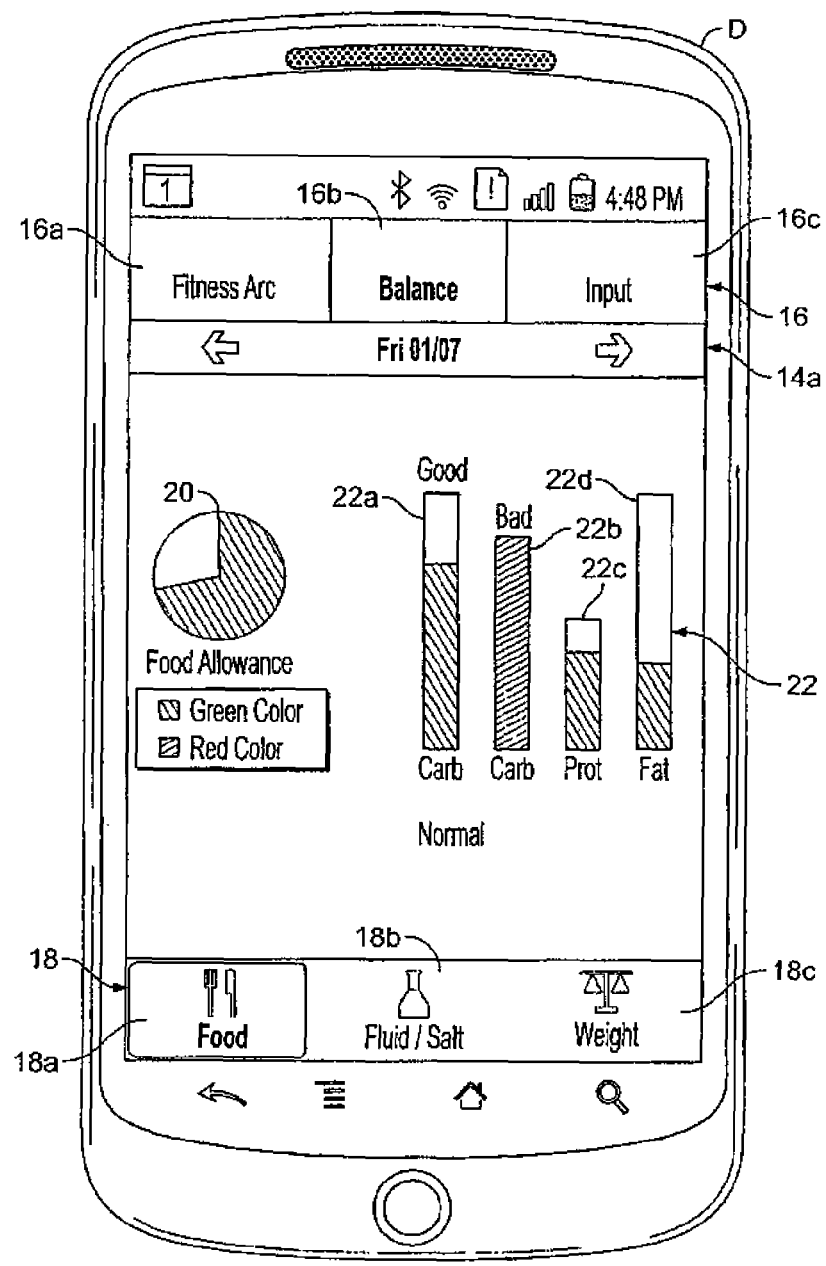
FIG. 2 is an illustration of a food circle information screen on the smart phone that can be provided by the application.

Referring to FIG. 2, the application 12 can be adapted to run on a digital device D such as a smart phone, tablet computer, or conventional personal computer, such as a desktop or laptop computer. In an embodiment, the digital device D may run a Smartphone based operating system. Alternatively, the application 12 may be employed on a stand-alone device such as a wrist-watch like device or other digital device (not shown) that can be specifically adapted to provide the functionality described in the present patent application.

The application 12 can include a plurality of software algorithm codes for displaying data, calculating data, receiving data and the like. When the software can be run on the digital device D, buttons such as primary input buttons 16, 16a-16c and secondary input buttons 18, 18a-18c may be displayed. The buttons 16, 16a-16c and secondary input buttons 18, 18a-18c may be touch pad input buttons when the digital device D includes a touch screen. In another embodiment, a graphical user interface, such as a mouse with a selection button(s) (not shown), e.g., the right or left key selection button on the mouse, may be used to navigate an icon about the screen of the digital device D and the selection button may be used to select one or more buttons 16, 16a-16c and secondary input buttons 18, 18a-18c, e.g., by clicking on such button representations of the screen or icons or the like.

Selected buttons 16b, 18a may be highlighted on the screen. In this case, the primary input button 16b for "balance" and the secondary input button 18a for "food" may be selected. In an embodiment, the button 16b for balance provides the following three secondary button options which can then be icons or button representations, e.g., positioned at the bottom of the screen as illustrated in FIG. 2. The options are briefly described below followed by more detailed disclosures in the present patent application.

The Food Tab/Button:

As depicted on the screen of the digital device D as shown in FIG. 2 a food circle 20 can be used to represent an allowed daily amount of food, e.g., that can be necessary to maintain a current weight of the user. It can be color coded, e.g., filled with green color which can turn red, e.g., as the user adds more food than allowed. It can be understood that colors described herein can be depicted as fill-patterns in the figures. Although the color code for the fill-pattern can be shown on FIG. 2, the code can remain the same for all figures in the present application. It can also be understood that any graphical element (e.g., food circle 20) that fills with the color red will also be accompanied by a message that will be displayed (not shown) which will described the impact of that color change on the relevant physiologic function. The amount of food required to fill the food circle 20 can be specific to each individual and can also vary with certain factors, such as the amount of activity the user performs. For example, if the food circle (pie chart) 20 can be red or partly red, the user should be gaining weight for that day and in proportion to the amount of the food circle 20 that can be showing red as opposed to green. The user can change color back to green, e.g., by doing more physical activity.

Figure 3:
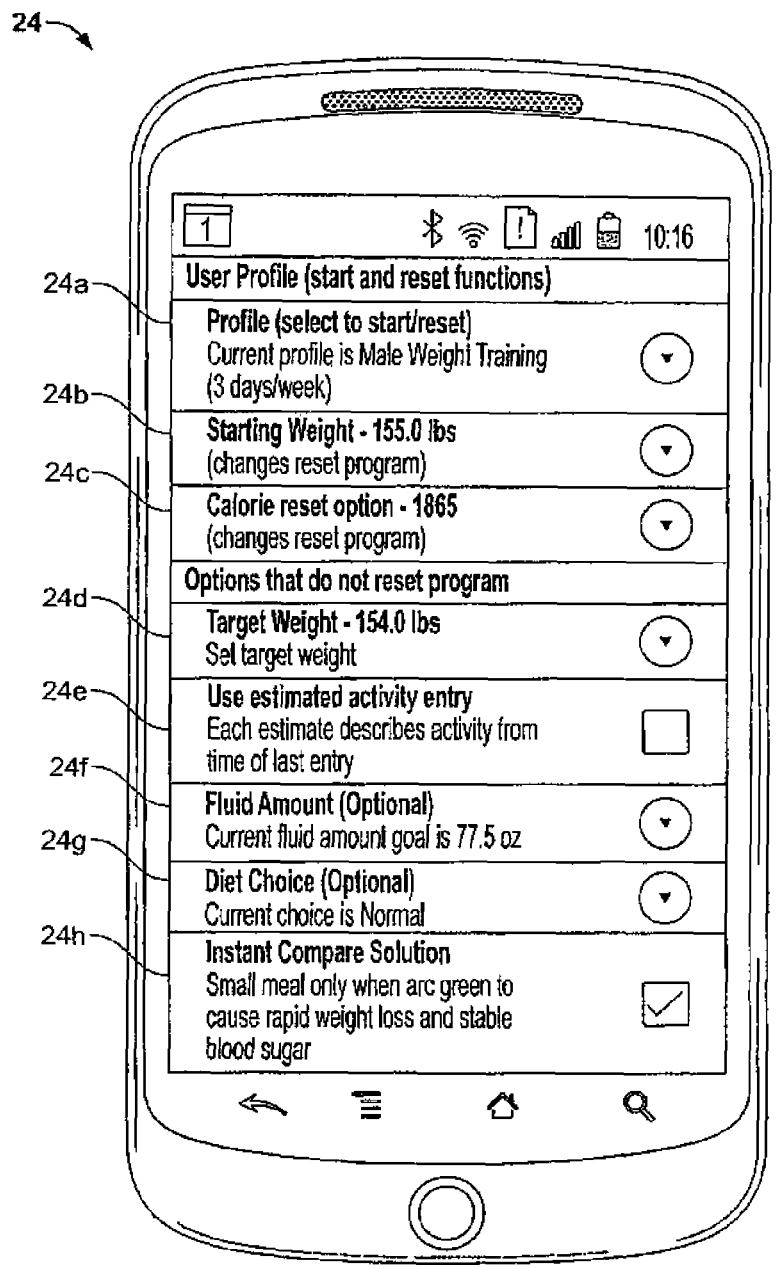
FIG. 3 is an illustration of a user profile input screen on the smart phone.
Figure 4:
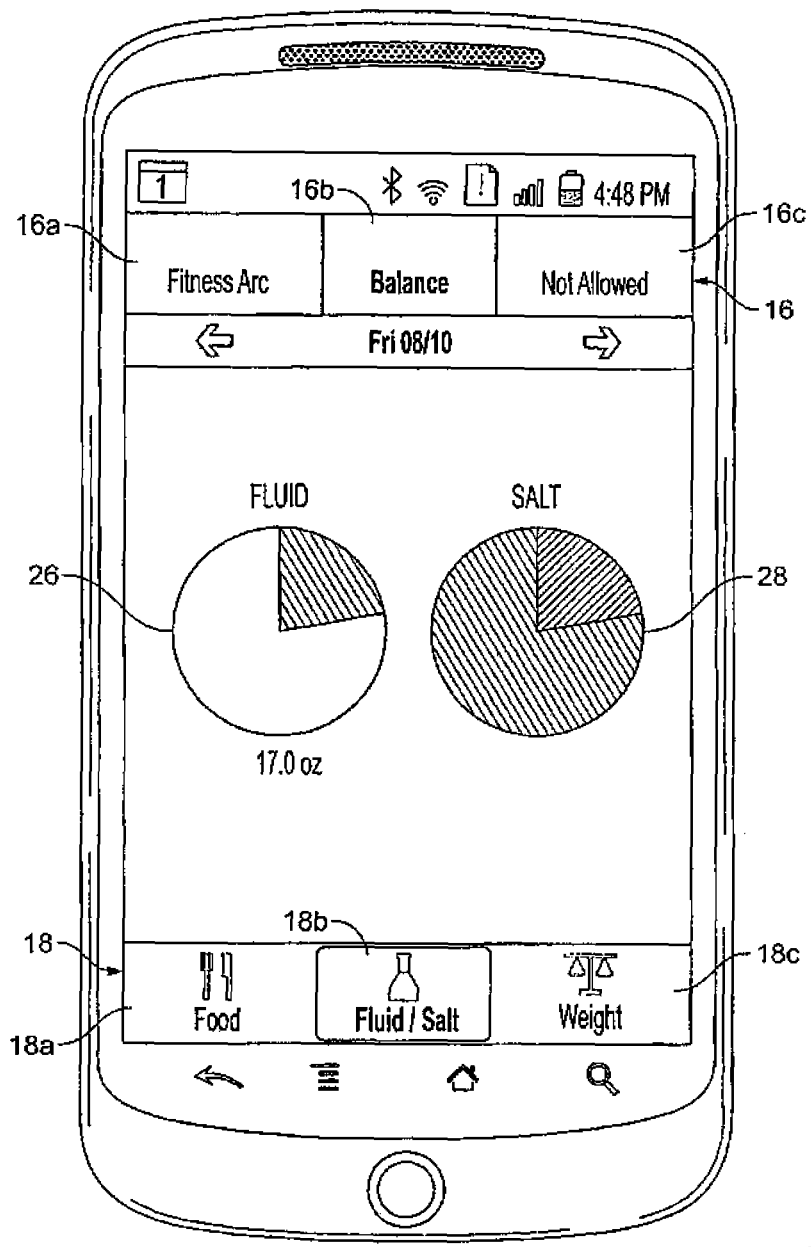
FIG. 4 is an illustration of a fluid and salt circle information screen on the smart phone.

Fluid/Salt Tab or Button 18b:

As depicted on the screen of the digital device D as shown in FIG. 4 fluid and salt circles 26, 28, respectively can be used to indicate a daily 26 allotment amount in circle 26, which may be determined from an estimated daily fluid consumption goal, which may be input by the user on field 24f, e.g., as depicted on a profile page 24 depicted in FIG. 3, discussed in more detail below. Actual fluid consumption can then be input by the user throughout the day. The salt circle 28 can fill, e.g., as dietary choices can be made throughout the day. Green can then be used to represent that the user can be consuming or has consumed salt in a manner that can be, e.g., consistent with current dietary recommendations. In an embodiment, if the user exceeds recommended salt allowances as the day progresses, the color can progressively change, e.g., to yellow, as indicated by the no cross-hatching for red shown in FIG. 2 and then red as the user inputs his/her food consumed.

Figure 5:
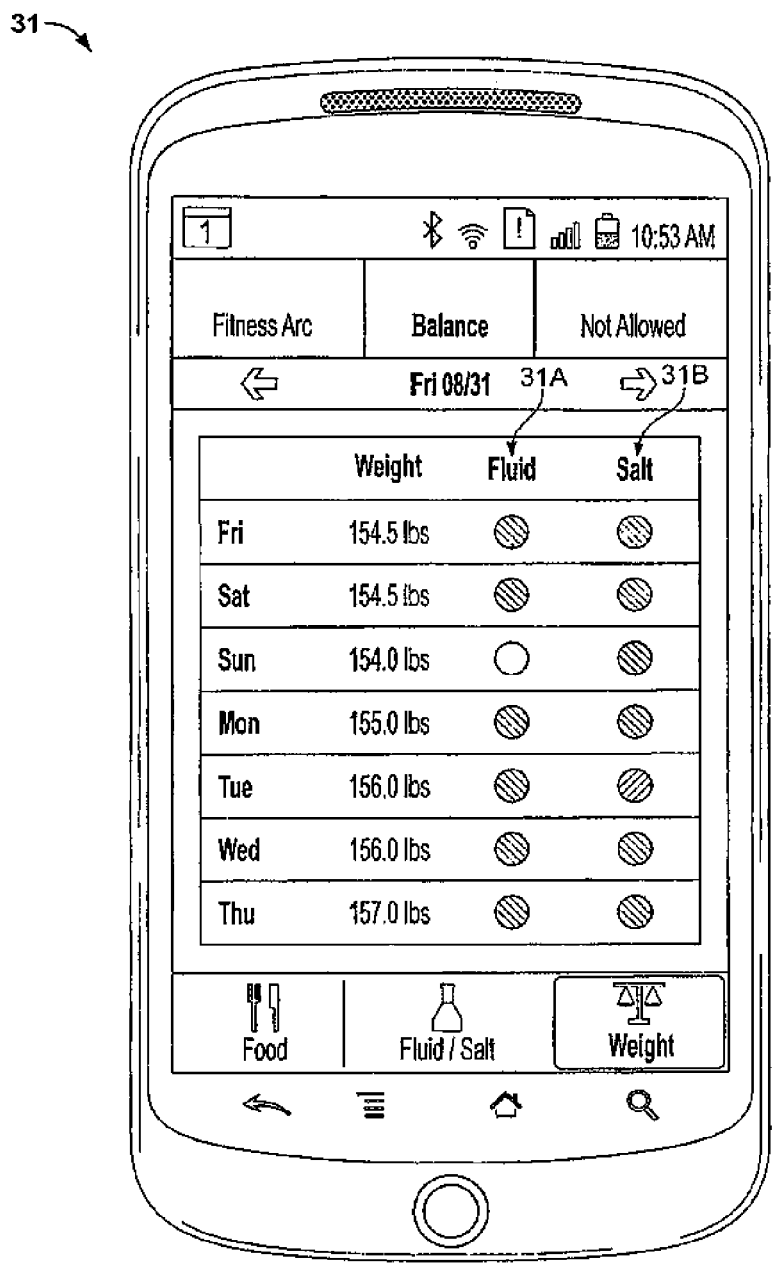
FIG. 5 is an illustration of a weight related to fluid and salt information screen on the smart phone.

Weight Tab/Button 18c:

As depicted on the screen of the digital device D as shown in FIG. 5, the device includes weight information, e.g., on a daily basis, and associated proportional fluid 31A and salt information 31B. Green indicates compliance with health and fitness guidelines, yellow indicates excess, and red indicates overly excessive (e.g., unhealthy) consumption. In an embodiment, previous weeks can be reviewed by tapping the left return arrow 33 on the date bar to move for display on the screen of the prior weeks and the right advance arrow 33 to move forward in time back to the current week.

As disclosed in more detail below, the application 12 can convert iconic food items input by the user into a numeric figure which, as an example, over time may be learned by the system, e.g., by derivation from an analysis of previous food selections and their impact on weight when also, e.g., compared with the user's actual and historic activity level and when referenced against the calculation of intrinsic metabolism by the system 10. The intrinsic metabolism may, by way of example, be held as a constant until it can be determined by the system 10 that this value for intrinsic metabolism no longer correctly predicts the direction/amount of weight gain or loss. At such time the system 10 may recalculate the value for intrinsic metabolism and retain it as the present constant, e.g., so that the instantaneous energy balance of the user can be calculated and displayed on a user friendly and readily identifiable graphic, as can be shown, by way of example in a fitness arc 34 in FIG. 6.

Referring back to FIG. 2, in an embodiment, graph 20, as illustrated as a circle graph, can be used to display allowed food intake and actual food intake, respectively, for a given day. For example, circle graph 20 may indicate that the user's total food intake for the given day can be less than the maximum prescribed, e.g. as indicated by the portion of circle graph 20 that can be white (no cross-hatching, e.g., indicating the food intake can be about 30% below recommended), or can be on target, e.g., if the green color increases to fill the entire circle (not shown in FIG. 2,) or can be "excess," e.g., by the portion that can be in red, that is not shown on the circle graph 20, but can be imagined as the white portion becoming green. This would then indicate, as an example, that the food intake was about 30% in excess.

As noted above, the circle graph 20 can be, e.g., a proportional representation of the way in which the user's daily food consumption has been distributed between the major food groups, and this can be calculated by the application 12. The circle graph 20 may show one color for food caloric intake (for example, a white background changing to green as calories are consumed), the background color also showing the food units remaining, which if consumed to the allowed amount can result in the user reaching the pre-selected weight goal (the white color remaining), and another color, e.g., red when caloric intake exceeds the allotted calories for the given time period. The graphic allowance for food intake can be adjusted to the user's activity level each day, so that, if the activity level increases above the expected, an adjustment can be made which can, e.g., allow more food to be entered before the food circle 20 can be completely filled.

In an embodiment, the bar graphs 22 may be utilized to further break down various food intake categories into separate graphs. For example, carbohydrates (carbs) may be broken down into bar graphs on good and bad carbs 22a, 22b, respectively, and protein and fat may be displayed on graphs 22c, 22d, respectively. Allotments (i.e. how much room there can be to fill the graphs for each food type) depend on the diet which can be input by the user in field 24g of the profile page 24 depicted, by way of example, in FIG. 3. If the user changes his/her diet, the bar heights for each of the food groups can also change. The graphs 22a-22d may be useful for persons on a low fat or a low carb diet. The graphs 22 may be color coded, as noted above as an example. For example, the good carb 22a, the protein 22c and fat 22d graphs may be partly green on a white background, to show that the daily allotment has not yet been consumed, but the bad carb 22b graph may be changed to completely red, showing that the daily allotment has been exceeded, or as noted above with the circle graph of FIG. 2, may change to red on the green background when and to the degree that excess bad carbohydrate intake is increased above the recommended level. The percentages of food type can be assigned by the application 12 so that the user only selects the iconic representation of the food item (i.e., during food consumption estimation inputs, as discussed in more detail below), and the application 12 can then determine the percentages of each elemental food type (i.e., protein, fat, carbohydrate, as well as salt content) that can be contained therein.

The actual allowed amount of food type which can be permitted before the graphs 22a-22d can completely fill in over the initial background color and change color can be determined by the allowed food amount, which can be determined, e.g., by the application 12 and the diet type selected by the user or health advisor, e.g., as input on a user profile screen 24 shown in FIG. 3. More particularly, with reference to FIG. 3, in an embodiment, the user profile input screen 24 can be employed to initially set up, as well as change, parameters such as Profile 24a (user sex, type and frequency of exercise training, etc.), Starting Weight 24b, Calories 24c (daily consumption objective), Target Weight 24d, User Estimated Activity 24e (estimate of number of user activity units, as described below), Fluid Amount 24f (amount of fluid desired to be consumed daily, in ounces). The fluid amount may be determined, e.g., by the user's weight, but the targeted amount of fluid to be consumed can be adjusted, by way of example, at the user's/health advisor's discretion. The color coding for fluid, in an example, may not attempt to target a minimum or maximum allowance, but may simply allow the user to track the volume of fluid consumed. The target for salt consumption may, e.g., track standard daily sodium content recommendations. In some cases, this may not be open to adjustment by the user. The user profile input screen 24 can also include parameters such as Diet Choice 24g, and an Instant Compare Option 24h (which can allow instant input of activity units in the application 12, as opposed to an input in the application 12 that attempts to replicate normal metabolic changes, e.g., every three hours, thus permitting the user to gain instant access to the impact of his/her activity units).

In an embodiment, the system 10 normally can be employed using some or all of the features described in the present application in connection with the application 12, e.g., while operating in conjunction with the activity module 14 (i.e., operating in a "combined mode"), or in a mode in which all the features described herein in connection with the application 12 can be operating without inputs from the activity module 14 (i.e., "the estimated mode"). The application 12 can be switched back and forth between the estimated mode and the combined mode on the user profile input screen 24 by checking or unchecking ESTIMATED (not shown in FIG. 3). For example, the user may elect i) to not wear the activity module 14 at all during a particular day, ii) or to just wear it for exercise only on a particular day, in which instance the estimated activity can be entered just before beginning the exercise. The activity accumulated by the activity module 14 can be downloaded after the exercise.

Figure 24:
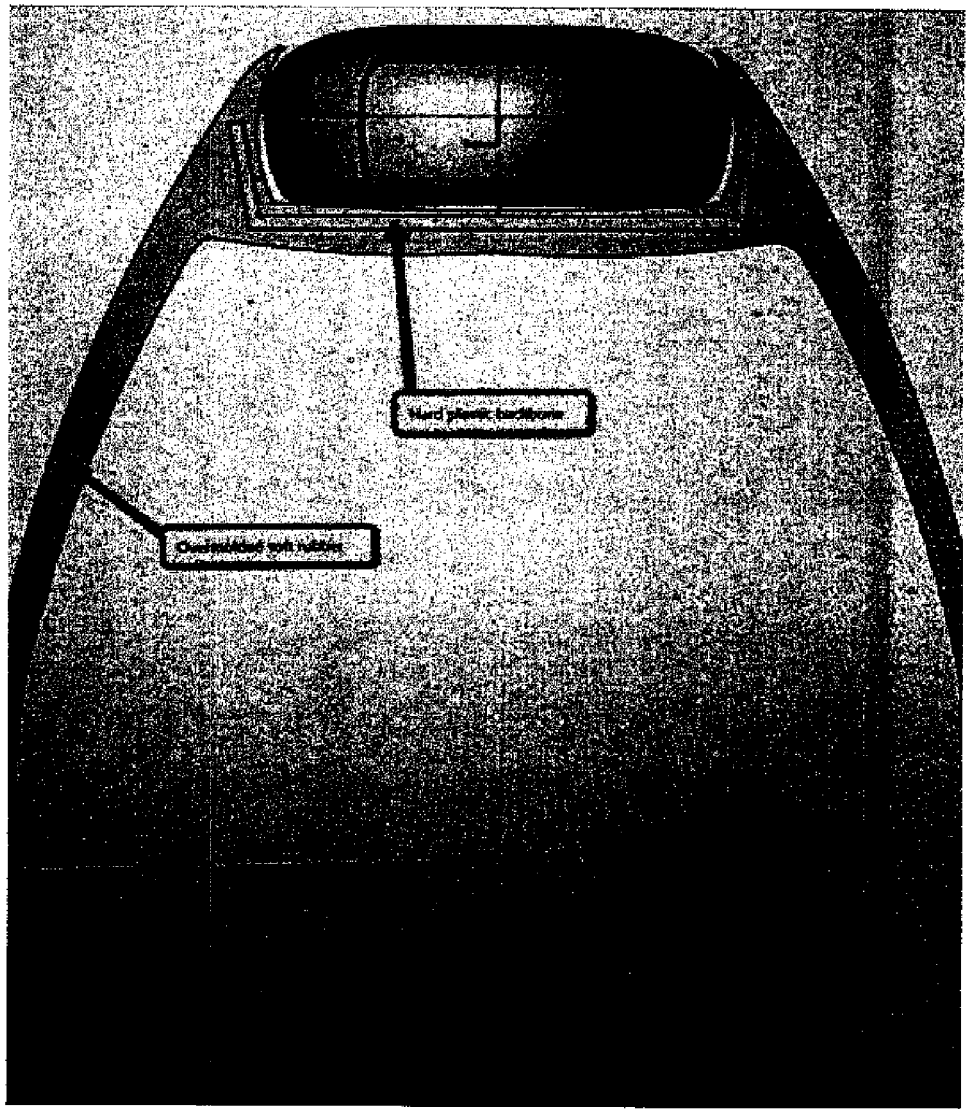
FIG. 24 is a side view illustration of a band for the activity module which has a strap with a receptacle holding the activity module.
Figure 25A:
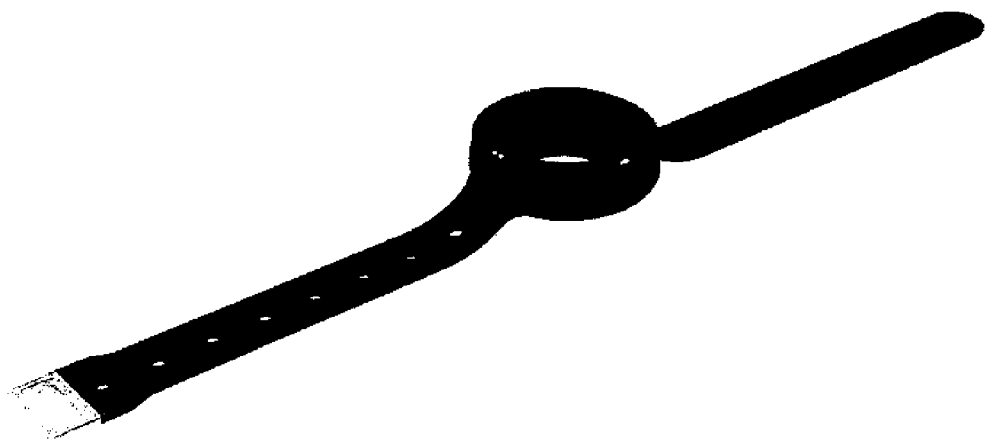
FIG. 25A is a picture of a top view of a band for the activity module which has a strap with a receptacle.
Figure 25B:
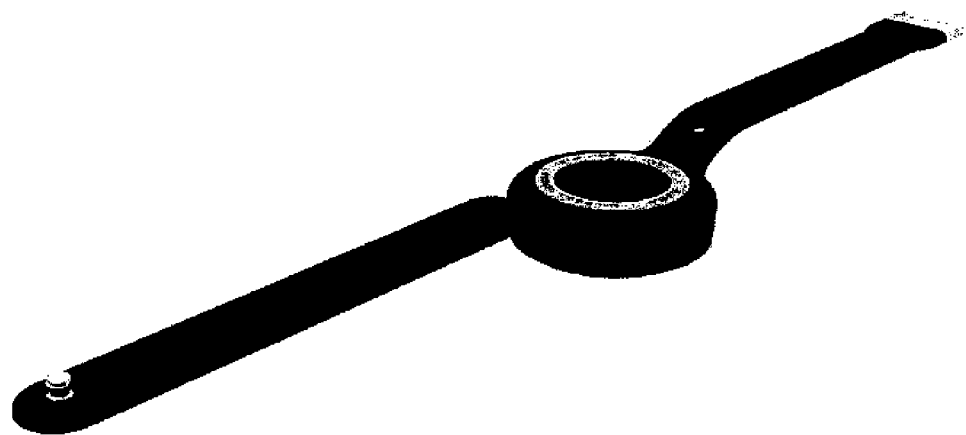
FIG. 25B is a picture of a bottom view of a band for the activity module which has a strap with a receptacle.
Figure 26A:
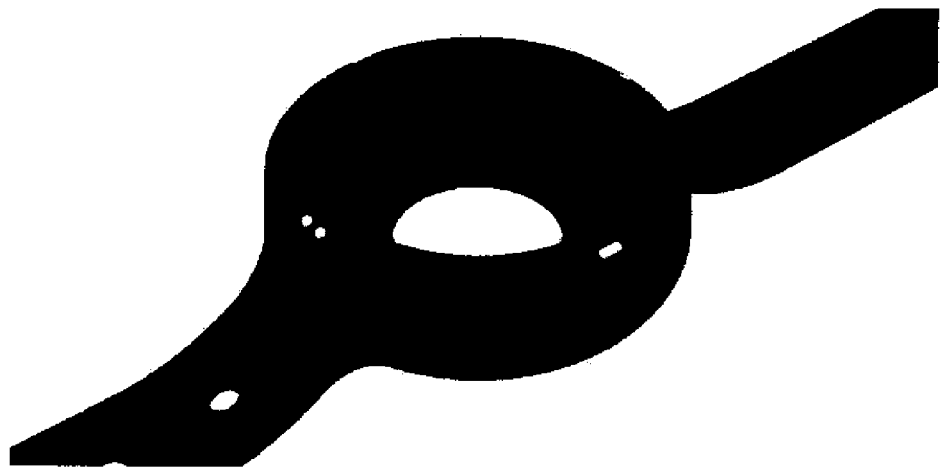
FIG. 26A is a picture of a top view of a receptacle.
Figure 26B:
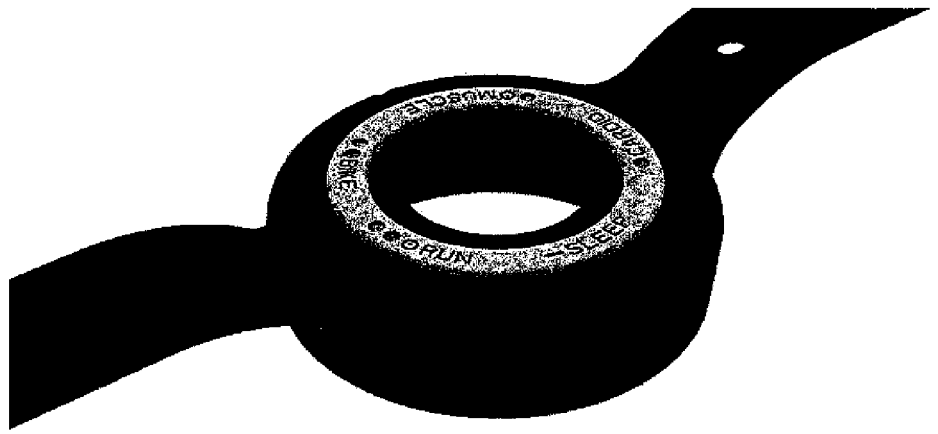
FIG. 26B is a picture of a bottom view of a receptacle.
Figure 27:
FIG. 27 is a picture of a top view of a band which has a strap with a receptacle holding an activity module.
Figure 28:
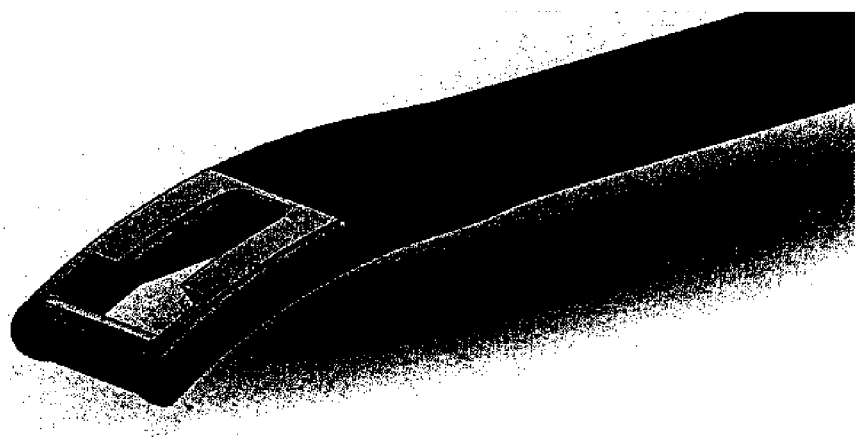
FIG. 28 is an illustration of a fastening mechanism of a band.
Figure 29:
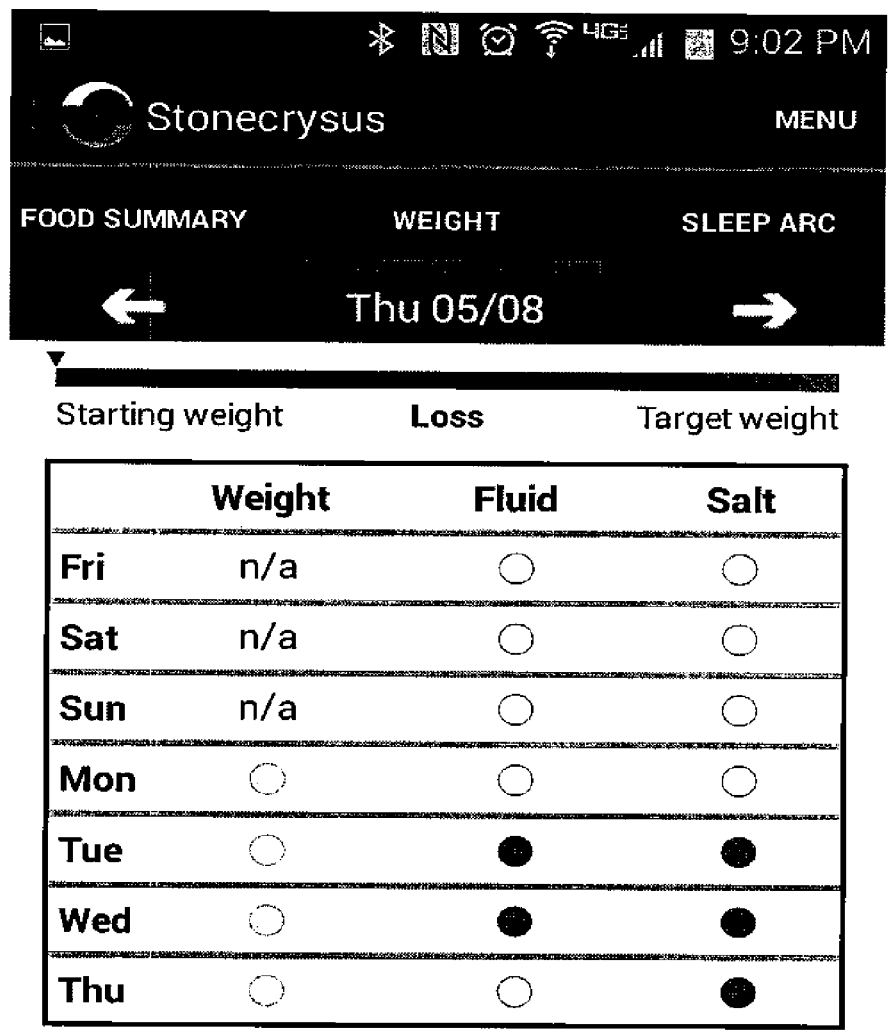
FIG. 29 is a screen showing weightless fitness management program results.
Figure 30:
FIG. 30 is a screen showing results of the activity monitoring mode for sleep.
Figure 31:
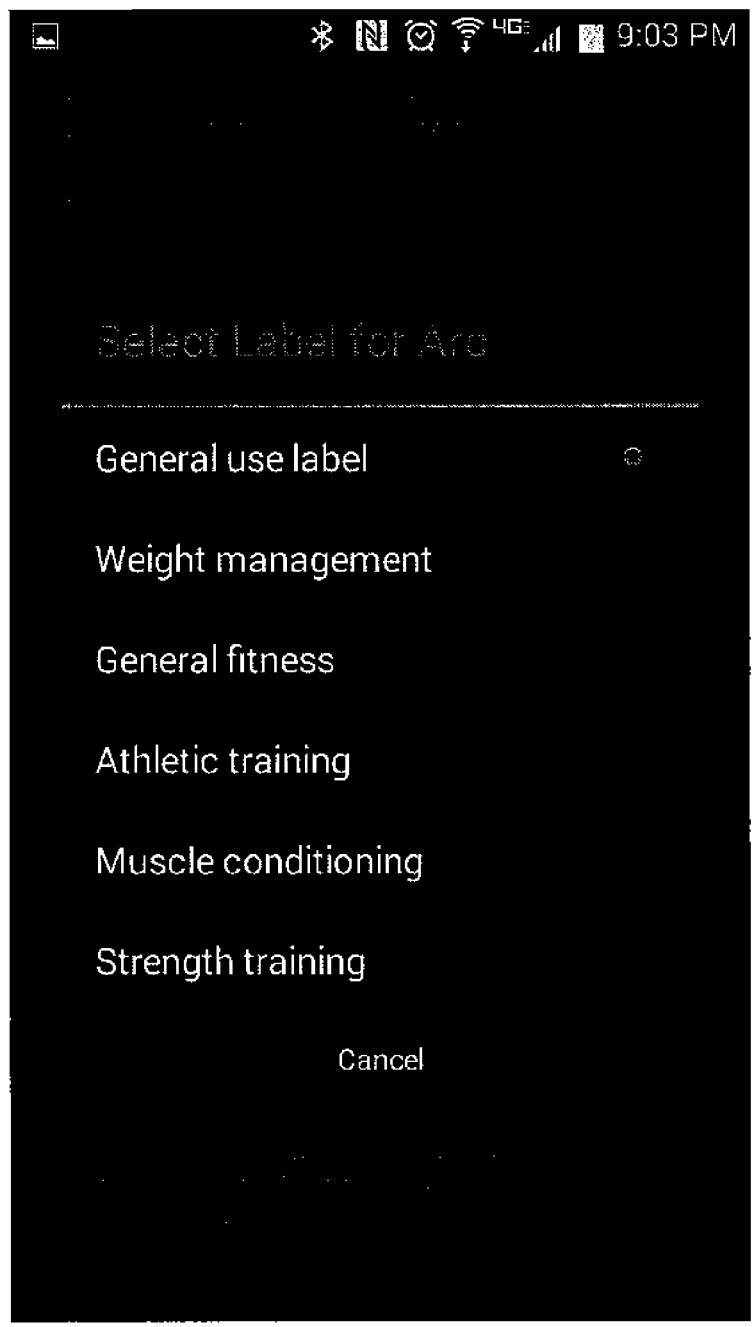
FIG. 31 is a user profile screen showing selection of an "Arc label"
Figure 32:
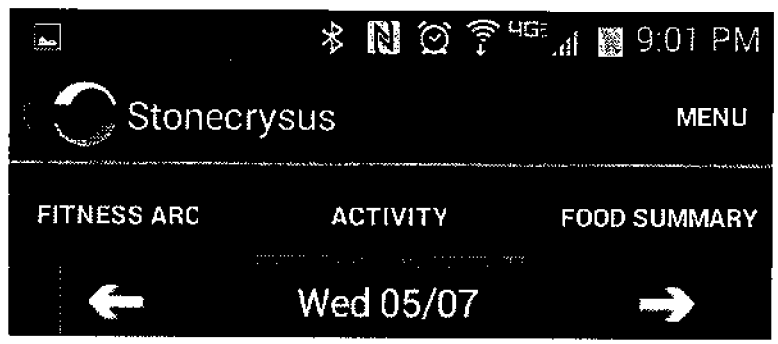
FIG. 32 is a screen showing training circles for muscle training (top) and cardio (bottom)
Figure 32:
Figure 33:
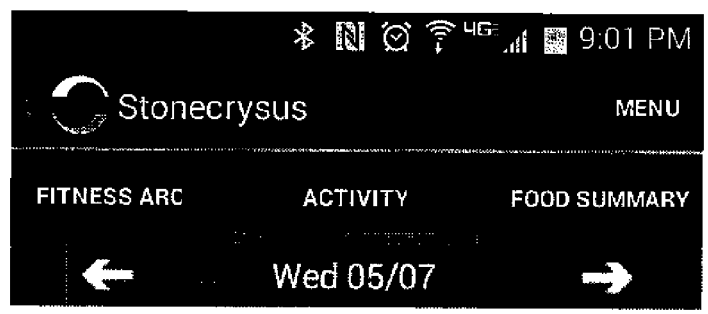
FIG. 33 is a screen showing an "Activity" circle displaying a user's total activity goal for the day and an "Activity Contribution" bar displaying the relative amounts of aerobic (60%) and muscle training (40%) performed to fill the activity circle.
Figure 33:
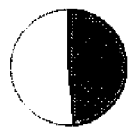
Figure 33:
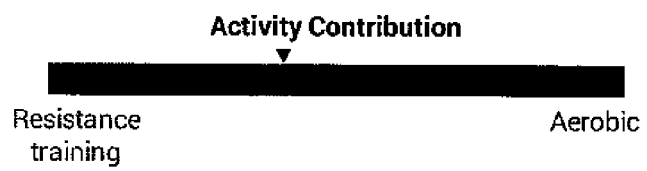
Figure 33:

Referring to FIG. 4, in an embodiment, when secondary input button 18b "fluid/salt" can be selected, the user can observe during the day his or her progress with fluid and salt intake, as it relates to the objectives established in the user profile input (i.e., see FIGS. 3, 24f and 24g). In an embodiment, the progress may be shown on fluid and salt circles 26, 28, respectively. The fluid and salt circles 26, 28 may be color coded to help reveal desired intake, current intake amount remaining or in excess of recommendation. The circle graphs 26, 28 may also be helpful, for example, in monitoring salt intake for users on a salt-restrictive diet. In addition, fluid/salt progress indicators can be associated with weight on a weight summary screen 31 which can be described below.

FIG. 5 illustrates a weight summary screen 31 listing the daily weight history and associated fluid and salt color coded indicator circles 31A and 31B, respectively, for the current week. Each food item can be assigned a salt value and serve to fill the salt circle 28 as a percentage of food units calculated by the application 12, such that the higher the percentage of the high salt foods, the fewer food units can be needed to be consumed to fill the salt circle 28. The fluid circle 26 depicted on FIG. 4 fills as liquids can be selected. The fluid and salt circles 26, 28 or representations of them can populate the listing 31 to help the user analyze the effect of fluid and salt on weight.

Figure 6:
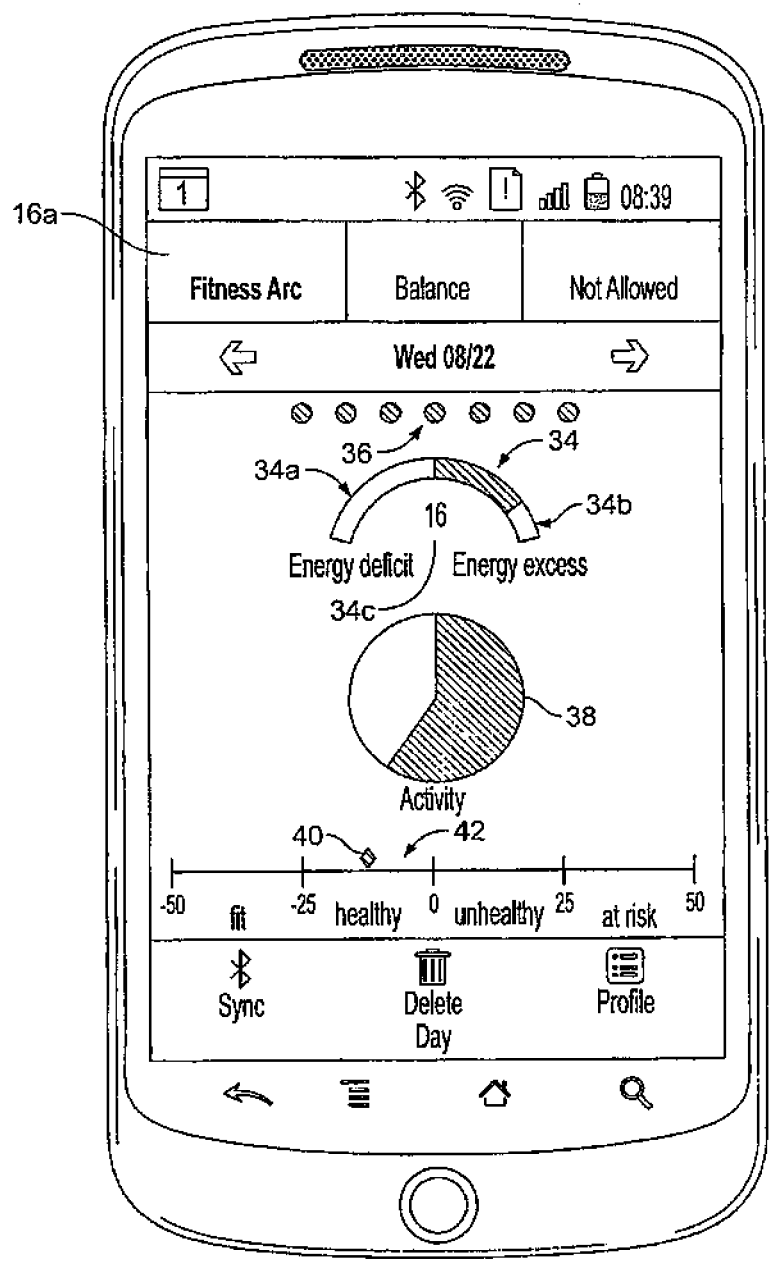
FIG. 6 is an illustration of a fitness arc information screen on the smart phone.

Referring to FIG. 6, the results of the energy balance calculation can be presented graphically on the digital device D screen, e.g., as a graphical fitness arc 34. The fitness arc 34 can be utilized to depict a measurement of daily energy balance and provide a daily indicator of fitness and health. In an embodiment, the accuracy of the fitness arc 34 can be enhanced by the application 12. More particularly, the application 12 can, e.g., periodically recalculate the user's intrinsic metabolism to provide an energy balance correction. Every person has a unique and changing metabolism such that consumption of similar quantities of food and similar amounts of activity can have different effects on the weight of the user, which weight can be utilized as a fitness indicator. Thus, there can be a different amount of remaining energy units available every day for storage as fat and therefore different consequences to weight in different individuals. This discrepancy can occur even if activity and food consumption can be identical. This constitutes the meaning of intrinsic metabolism according to the presently disclosed subject matter. These parameters can be continuously varying, i.e., they can be constantly changing with resultant different effects on weight for any individual user. The application 12, by monitoring its ability to predict weight based upon the activity units and food intake input, can constantly vary the allowed food intake should the application fail to accurately predict the change in the weight of the user. Thus, the continuous variable of intrinsic metabolism can, as an example, constantly be adjusted to correct for changes in the rate of energy consumption as fitness levels change or as food consumption and activity patterns change. By adjusting the metabolism calculation the application 12 can, e.g., determine modified food allowance(s) to match changes in activity.

The application 12 by way of example, can work without a requirement that the food input from the user be accurately reflective of the actual calorie content of food consumed. The application 12 only requires that the user have a reasonably similar pattern of icon use to describe food intake. For example, a sandwich eaten on one day may be bigger or smaller than the same eaten the day before, but the system does not require the user to actually reflect the absolute caloric content consumed. The algorithm can, by way of example, learn the way the user describes food and then assign a food unit value to each food component, e.g., contained within the sandwich, based upon an algorithm utilized by the application 12. In this manner, any habitual over/under food portion estimation(s) by the user can be detected and compensated for, thereby facilitating the application 12 in maintaining or reaching a user's target weight goal as specified in the user's profile (see FIG. 3, 24d).

Continuing to refer to FIG. 6, when primary input button 16a, "fitness arc" can be selected, a color coded energy deficiency/energy excess fitness arc 34 can be displayed on the display screen of the digital device D. In an embodiment, the fitness arc 34 can be formed in a semi-circular shape, where one side of the semi-circle can be an energy deficit portion 34a (i.e., indicative of weight loss) and the other side of the semi-circle can be an energy excess portion 34b (i.e., indicative of weight gain). In an embodiment, a red color may show when the energy deficit 34a can be present for that particular moment of the day (e.g., within periodic updates, such as, 10 minute updates), and a green color may show when the energy excess 34b can be present for that day. The portions 34a, 34b of the fitness arc 34 can change throughout the day, depending on the user's indicated physical activity and indicated food consumption. In an embodiment, coincident with the update of the fitness arc 34, a fitness arc value 34c can also be displayed. This value can represent the delta or change in fitness arc 34 units with each periodic, e.g., 10 minute interval, e.g., plus for an increase in energy excess (the body can be consuming energy through activity at a higher rate than necessary based on indicated food intake and the current intrinsic metabolism of the user) and negative for an increase in energy deficit (the body can be consuming energy through activity at a lower rate than necessary based on the indicated food intake and the current intrinsic metabolism of the user). At the conclusion of each day, the fitness arc 34c final value can be displayed. It can also be understood that the value for the fitness arc can be normalized and the color coded indication on the arc 34 used to indicate the positive or negative state of the energy consumption.

The fitness arc 34, therefore, can be used to visually inform the user as to the effect of the real time food consumption of the user referenced against the real time analysis of the actual physical activities of the user. At any given point in the day, the actual activity units and their impact on the fitness arc 34 can then be referenced against expected or historic levels of activity for that same time of the day. The fitness arc 34 displays can be adjusted based upon what can be expected and what has occurred. Activity units can be measured and assigned a value based upon the currently determined value for the calculated intrinsic metabolism of the user. The activity unit's value can be then used to calculate the energy balance that also can then be used to predict weight gain or loss, even before the food consumption or activity can be carried out.

Thus, given the inherent variation between each individual's rate of intrinsic metabolism and the manner in which he/she describes the food with the available icons, and/or activity input, each user can have different food unit values assigned to the same indication for a food item(s). The effect of activity on the balance of energy can be calculated, not directly against the food unit intake but it can be first processed, by the application 12, through a separate algorithm, e.g., imbedded in the calculation of the intrinsic metabolism. Thus neither food nor activity directly affects the energy balance or fitness arc 34, but can be instead analyzed based upon their historic and/or learned impact on intrinsic metabolism. The application 12 thus can create an ongoing user profile of intrinsic metabolism, activity, and food choice/amount that can be unique to each user. In an embodiment, the various components of application 12 may be calculated periodically, e.g., at 10 minute intervals, although other intervals can be also applicable. In an embodiment, it may take the application 12 about two weeks to define and calculate the user's metabolic profile and assign the values to his/her activity units and food intake units. It can be understood that such analysis can be further refined and adjusted by the selection of a target weight by the user. The algorithms, programs, or calculations underlying the behavior of the fitness arc 34 are described in greater detail below.

As disclosed above, the four components or parameters used by the algorithms in the application 12 can be indicated food intake (and, thus, apparent calories consumed), indicated type and amount of activity, i.e., exercise (and thus, apparent calories burned through activity), weight, and finally the calories necessary to maintain basic physiologic function, i.e., intrinsic metabolism. The application 12, therefore, can begin a monitoring process by assigning a value to each of the four parameters and running a series of daily calculations to determine the accuracy of the assigned values in relation to one another. The accuracy can be determined, by way of example, on the ability for one set of assigned numbers to accurately predict the others. Based on a weighted numerical coefficient of each data point which can, e.g., vary at specified times of the day and week, the algorithm can, e.g., choose three of the four definable parameters and then calculate the fourth variable, e.g., for one, some or all of the variables.

If the algorithm fails to predict the fourth value accurately, where accuracy can be defined in such a manner that, e.g., if the calculated variable can be reinserted into the application 12, the application 12 accurately predicts the parameters that can be measured at that time, which can be seen as confirming the accuracy of the calculated variable, then new values may be assigned, e.g., to the other variables, and the calculation redone until each variable accurately predicts the others when inserted into the algorithm of the application 12. The variables chosen for analysis may also be seen and learned to vary at different times of the day or week and the application 12 suitably varied to specify that the value can have the greatest accuracy relative to the other values according to the learned/determined variability. This recalculation may also include actual weight which can be directly measured.

The most complicated of the calculations may often be determined to be that of the intrinsic metabolism for a given user. In this case, there may be no direct measurement and thus the value can be, of necessity, a derived value, which may also vary from user to user and for a given user over time and in many cases according to one or more variables, e.g., daily, weekly, monthly, seasonally, time of day, exercise schedule and the like. This changing variable for intrinsic metabolism can be, e.g., derived from the dynamic interplay of the measured/indicated variables, which can be, e.g., first referenced against, e.g., the predicted value and/or actual value of each parameter. As data about the individual user can be collected, the learned allowed variance between measured variables can be narrowed. The intrinsic metabolism can be calculated and held as a constant.

However, the intrinsic metabolism may be, e.g., held as a constant only for a prescribed period and recalculated as metabolism for the user changes. In other words, if three of the variables can be measured and a rate of change in weight calculated, a constant can be calculated for the intrinsic metabolism. The constant for intrinsic metabolism currently calculated can then be used to predict weight given the indicated activity and indicated food intake. Should the algorithm fail to accurately predict weight given the indicated activity and food intake for the user, then the constant for intrinsic metabolism can be changed. When the constant for intrinsic metabolism can be found to perform adequately in the algorithm of the application 12, the algorithm can maintain the use of the constant and predict, e.g., using changes in either indicated activity or indicated food intake to predict a cumulative impact on fitness, e.g., as measured by change or lack thereof in weight. The algorithms of the application 12 can then be used to study the relationship between the two ongoing variables, indicated activity and indicated food intake, and combine the variations simultaneously and contemporaneously to each other so that, as an example, as one varies, the other can be determined even without the necessity of direct and absolute measurement for the variable, i.e., in such a way that if the user were to actually consume the entered indicated food intake and/or were to actually perform the indicated/entered number of activity units, then the user's weight would remain unchanged. In other words, the algorithm for the application 12 can adjust to inaccuracies in the indications of the food intake and/or activity level, which, if consistently entered by the user and/or determined by the system 10 from inputs from the user or inputs from a component in the system 10 itself, can still determine a constant for intrinsic metabolism and other metabolic activity of the user so as to accurately predict change in fitness over time, as indicated, e.g., by change in the weight of the user.

The display in the fitness arc 34, by moving in the left or right portions, can be seen to denote how far the user can be from good fitness behavior, e.g., as indicated by weight neutral behavior. The fitness arc 34 scale can be set so that if the combination of indicated food consumption and indicated activity performed produces a full energy excess red arc portion 34b for a given period of time, e.g., for seven days, then the user can have gained a predictable amount of weight, e.g., at least one pound, in that given period of time, e.g., one week. If the combination of indicated food consumed and indicated activity performed produces a full energy deficit green arc portion 34a, again for a given period of time, e.g., for one week, then the user can have lost the predicted at least one pound in that week. In this way fashion, an accurate prediction of weight change can be maintained, e.g., as long as the intrinsic metabolism of the user and the user's pattern of identifying indicated food intake and/or indicated activity type and amount also remain the same or essentially so.

Variations in indicated food intake versus indicated activity, therefore, can then be used to inform the user as to the expected affect on weight as well as on an overall health quotient 42, as discussed in more detail below. With variation in indicated food intake and/or indicated activity, either due to change in behavior by the user or change in the way of inputting the indicated behavior of the user, e.g., vis a vis food intake and/or activity, on a more or less real time basis, the system 10 can advise the user as to how much variation in the one or the other can be needed to achieve a certain weight.

Should the application 12 then show an indication(s) that it cannot make such predictions accurately, e.g., the constant (i.e., intrinsic metabolism) can be recalculated and/or new values can be assigned to an indicated parameter(s) so that they can be weighted in a way that accounts for the observed variability, leading from, e.g., a user's over or under indication of real food intake and/or real activity. By way of example, the greater the variability of the user inputs from the reality of the food intake and/or activity, the greater can be the value for the derived increase or reduction in the weightings assigned to that value in the calculations by the algorithm. In other words, the intrinsic metabolism can be a constant derived from measured values (as a function of user input, e.g., for food intake and activity) which themselves can be defined by tolerance parameters assigned by the application 12 itself, e.g., referenced against actual indicated weight change, and the currently determined constant for the intrinsic metabolic rate of the user.

In an embodiment, the fitness arc 34 can be used to depict the relationship between two power equations. The first power equation, e.g., can measure the rate of energy transfer, and the second power equation, e.g., can measure the movement of a fixed mass over a specified distance per unit time. The relationship expressed in the fitness arc 34 can be, e.g., a percentage change between the expected and observed value of each power equation. The percentage change of each equation can be given a weighted value and then the two can be summated to produce a graphic representation, e.g., of relative change against an absolute weight unit. The first and second power equations are discussed in more detail below.
Power Equation 1

In power equation 1, power P can be defined as the rate at which energy can be transferred or consumed, and food units can be calculated, e.g., to be user specific, as units of energy taken in by the user. Another way to express this can be the familiar "calories in vs. calories out." Once calculated, food units and energy used units can form the basis upon which a metabolism for the user for a given level of indicated activity undergoes an update as to the rate at which the user actually consumes the indicated amount of intake of food units. The food units can be seen as energy equivalents which can have different values for different foods, types of food and even different users. Food unit values can then be assigned, e.g., by the ability of a given indicated value for the food unit(s) to effect weight, and not by an absolute caloric amount. These food units may be, by way of example, assigned an initial value based upon a published caloric content. The algorithm of the application 12, can then reassign a value(s) to some or all indicated food(s) intake(s) periodically, e.g., on a weekly basis, e.g., based on how the food(s) affects the weight of the user.

The application 12 may do this, e.g., by maintaining ratios of initial assigned food values versus learned/established value(s) such that the ability to affect the weight of the user as determined from the current value for the intrinsic metabolism for the user and the indication(s) of food intake by the user can be used to determine a value for a food unit. Thus an extra 3500 calories (i.e., the number of calories required to gain one pound) may be more or less than the food units as used by the application 12 to change and/or predict a change in the weight of the user by a given amount, e.g., by one pound. Once the value of energy can be assigned to a food unit, as an example, a weekly allotment of food(s) can then be used to determine the ratio of the food units (e.g., calories) of the food(s) to the food units used by the application 12, and can be extended to all food analyzed by the application, at least as a starting value, regardless of whether or not that particular food has been consumed and thus previously analyzed by the intrinsic metabolism calculation.

$$\text{Power } P = E_t \qquad \text{Power equation 1:}$$

where $E_t$ is the energy transferred to the user from that stored in food units indicated to be consumed by the user to the energy needed to be used up (indicated to the system 10 to be used up or predicted by the system 10 to be used up, by the user (over some period of time) in order to maintain the total metabolism of the user (including the current constant for intrinsic metabolism of the user) so that there can be no change in weight during a given period of time, e.g., in the course of one week. It can be understood that this may be expressed as a ratio of energy in to energy out (user total metabolism) or the ratio of energy in to the energy consumed by the excess activity of the user over and above the intrinsic metabolic rate of the user.

The rate of energy transfer can be estimated from the rate at which weight can be gained or lost. The unit of energy can be defined, e.g., by the number of food units necessary to maintain a stable body weight, given an indicated level of energy used by the user in the course of activity by the used as indicated by the type and amount of activity input by the user and the activity module, as discussed in more detail below. In an embodiment, the food unit energy value can be established by determining how many food units can be consumed over a period of time, e.g., one or two weeks in which there can be variability in weight. The variability in weight can then be referenced against the variability in food units taken in to determine the number of food units which would result in a change of one pound in weight, also referenced to indicated activity level(s).

As an example, the number of food units minus the number of food units attributable to the addition of one pound can be identified by the term "expected value". It can be understood that the same estimation can be made for a pound of weight that can be measured to be lost. The "expected value" can be the number of food units that, for the specified time of the day, and the actual/predicted activity level(s) the application 12 anticipates the user can consume. If the "expected value" can be consumed in each interval (and the activity units described below can be known/predicted, e.g., held constant), the user can maintain weight neutrality over the course of the given period of time, e.g., one week. The 10 minute processing of the relationship between the expected and the observed can then be displayed in the fitness arc 34. In different time periods, a different number of food units may be expected. The "expected food units" during, e.g., a ten minute time frame can be used as the number of units that would maintain weight neutrality and the observed variance from expected food units could be used to determine the rate at which energy can be being transferred to i) fat which can be stored energy (i.e., weight gain), or ii) removed from energy stores and converted to heat plus kinetic energy (i.e., weight loss).

The food unit increase or decrease from "expected" can be expressed as a (+) or (−) percentage. This percentage can be used in the fitness arc 34. More particularly, a negative percent that shifts the fitness arc 34 to the left can indicate an expected weight gain, and a positive percentage that shifts the fitness arc 34 to the right an expected weight loss. The units in the fitness arc 34 can be based upon relative value units or units of percent change. The affects of the power equation 1 on the fitness arc 34, as noted, can be modified by the power equation 2, discussed in more detail below.
Power Equation 2

In power equation 2, power P' can be defined as the rate at which work can be performed. More particularly:

$$\text{Power } P' = \text{Force} * \text{Displacement/time.} \qquad \text{Power equation 2:}$$

Where force can be the energy needed to move a pre-specified mass a pre-specified distance per unit time.

Force can thus be defined as the ability to move the weight of the individual user (i.e., mass) a pre-specified distance in a pre-specified time. The pre-specified distance can be that which the individual can be able to move in an allotted time. The allotted time, as is disclosed in greater detail below, can be that time allowed by the programming of a motion sensor (e.g., an accelerometer) located in the activity module 14 worn by the user, which can, e.g., be used to count each deflection of the motion sensor (e.g., accelerometer) in a specified general direction as a separate event. This time, may be, e.g., measured in fractions of a second. The distance traveled can be seen to depend upon the ability of the user to move his/her weight a given distance, which can be fixed by the individual's current unique locomotion characteristics. He/she can only move so far in the time allotted no matter what his/her level of effort because after a brief first number of milliseconds of acceleration, a terminal velocity can be reached and limit the distance traveled. Thus the distance that the user's mass can travel during the period of measurement can be seen to be fixed across a wide range of physical activities, e.g., walking, trotting, jogging, sprinting, etc.

Human physical activity can be episodic and therefore have nonlinear acceleration. Because the time allotment between separate episodes of acceleration can be set in fractions of a second, the activity module 14 can be, e.g., capable of counting sequential and multiple events, even though the events may be occurring in rapid succession. This can have the effect of allowing the activity module 14 to count activity units over a wide range of physical activities, as noted above, or, e.g., swimming, jumping, weight lifting, etc. and doing so in such a way that each count (e.g., a stride, swimming stroke, weight lifting repetition, etc., can be used to represent a user prescribed and constant activity unit, i.e., value for energy use by the user. The pre-specified time allotment can be a specified unit of time over which the motion sensor (e.g., accelerometer) can be used to count each motion as a separate event.

As noted above, each displacement (or each displacement in a preselected general direction, can be utilized to equal the activity count. Time can be extended over a period of exercise or over a longer period of time, such as one week, or separately calculated and summed over the longer period of time. Force can be the ability to move mass (the weight of the individual) a specified distance (measured, for example, in accelerometer counts) in the time specified. The time between acceleration events of the accelerometer can be calculated by the application 12 as separate events. Because the application 12 can define force utilized by the user as a constant and displacement can be measured in activity units as described above, the power variance can be measured as a comparison of the accelerometer deflections per week.

This can be averaged over shorter periods of time, and, e.g., calculated to an average for 10 minute intervals. However, the units of displacement (activity units) of the user mass, walking or swimming, as an example and/or weight being lifted, e.g., can be expected to occur in pre-specified intervals. Therefore expected activity can also be seen as varying according to the time of day. There can be, e.g., an expected number of activity units per unit time and an observed number. This relationship can be represented as a percentage change whereby an increase percentage of activity units can be utilized, e.g., to shift the fitness arc 34 to the left in region 34a, and a deficiency can be seen to shift the fitness arc 34 to the right to the region 34b. In addition, the entry of the activity unit percentage can also have a timed entry into the fitness arc 34 calculation regardless of what segment of the day in which they can be actually performed. This timing reflects the manner in which the total expenditure of energy to perform work W (wherein W=power×time) can be projected, e.g. in a physiologic model, rather than instantaneous in the physiologic model.

Overall, power equations 1 and 2 can each be given a relative weight and then summed to produce a percentage change in observed versus predicted food energy units consumed and activity unit energy expended. The depiction of this percentage change, taken together with the effects noted above as to indicated/predicted food intake, can result in the value shown on the fitness arc 34. The fitness arc 34 can thus represent absolute energy excess versus energy deficit or energy excess versus energy per unit time in specified units. The units can be defined in the power equation calculations, but where the fitness arc 34 can be expressed as a percentage change, the units need not be indicated to the user. Any units for the value shown on the fitness arc also would not provide any additional meaning because the fitness arc can be seen to be defined for each user and have value only in that the fitness arc represents a unit of comparison of energy balance for the particular user.

The application 12 can reference published calorie value(s) of a particular food being consumed by the user, but does not necessarily define the value inside the algorithm, particularly considering that the calculations within the algorithm can be based upon how the user represents the food intake and the impact of the represented food intake along with the represented activity level(s) impacts weight variance for the indicated food intake, when weighted against indicated physical activity, and considering the current value for intrinsic metabolism of the user. The published calorie content of food may be completely coincident with a food unit value, but the calculations of the algorithm used in the application 12 do not require any such equivalence for accuracy of its intended functions.

Calculated food units values can be independent of actual caloric intake used in the application 12 to describe the user's metabolism. The user can be enabled to know his or her metabolism's energy balance expressed as change in a fitness measure, e.g., an absolute and/or percentage change in weight over a given period of time, e.g., the loss or gain of one pound in one week. The display of this relationship on the fitness arc 34, on which, as noted, there can be no units, can be viewed as a degree of colored filling of one or the other of the two portions of the arc of the graph, i.e., 34a, 34b. The energy units can be derived from the power equation 1 which quantifies the rate of energy intake, which, to the extend such exceeds the intrinsic metabolism for the given user, and if not expended, can be transferred into stored energy (fat), which can be expended in the form of energy used in activity by the user, i.e., energy units taken in modified by the power equation 2, (i.e., the movement of the individuals mass over a specified distance per unit time).

Since movement requires that force be delivered over a specified distance in a specified time on a specified mass, an energy unit can be derived which can predictably modify the fitness arc 34 energy transfer representation in a manner which reflects an energy balance (at least a predicted energy balance) for the user, e.g., at 10 minute intervals. Therefore, the fitness arc 34 can be used as a representation of energy balance as quantified by the energy transformation of food into fat or food into physical activity per unit time, such as, the relative movement of the mass of the individual user over distance per unit time.

It should be understood that the calculation for weight gain can be mathematically the same as the weight loss calculation. The calculations can be weight neutral algorithms. For instance, in the weight gain algorithm, one pound can be added to the neutral or per unit time, e.g., weekly, base weight. In this way the application 12 can allow the user to gain one pound each week by eating calories in excess of the number needed for weight neutrality. The intra-week calculations can be utilized, e.g., to allow for appropriate calorie (food unit) intake to limit weight gain to the desired one pound per week, taking into account, as noted above, the energy expended or to be expended by the user in the week. More specifically, in the weight gain algorithm the user can be instructed to push the fitness arc 34 into the red or energy excess portion 34b of the fitness arc 34. If at the end of the given week, the user weight of the user can be more than the desired weight gain, the food unit allowance can then be readjusted downward, to provide less extra calories for achieving the desired weight gain of one pound in the next week.

Continuing to refer to FIG. 6, in an embodiment, located above the fitness arc 34 can be a series seven color coded dots 36. At the end of each day the fitness arc 34 can be used by the application 12 to assign a color to one or more (?) dots 36 representative of a given day of the week. The current date can be located in the bar above the dots 36, and the dot 36 corresponding to the current date can be indicated, e.g., by being underlined (not shown in FIG. 6). There can be one dot 36 for each day of the week. The series of seven color coded dots 36 can be utilized, e.g., to summarize the fitness arc 32 results for each of the seven days. The dots 36 may be green to indicate positive fitness gain for a given day, black for neutral, or red for weight gain. For a given day, the dot 36 can be green if the fitness arc 34 can be fully green, red if fitness arc 34 can be fully red, and black if the fitness arc 34 is not a full color. The accumulation of 7 green dots 36 can indicate that the expected one pound of weight loss should have occurred, and a mixture of color dots 36 can be seen to indicate a variable effect on weight and fitness. The occurrence of a red dot 36 can be seen to indicate a slower progress with the weight loss process. The energy intake excess, e.g., as indicated by the red dot 36 can indicate the undesirable effect of resetting the body of the user to a natural state which can be to store fat rather than break it down. Day to day variations, particularly of more than ½ of a pound, can be most likely fluid gain or loss. These variations can be difficult to interpret in isolation. The system 10 over time can calculate actual changes in body mass that, e.g., are not the result of water weight fluctuations.

Continuing to refer to FIG. 6, in an embodiment, a circular shaped activity circle 38 can be utilized to indicate the amount of physical activity (e.g., exercise or motion) achieved for a given day, or, alternatively, cumulatively over the given longer time period. The activity circle 38 can be filled using data provided from the activity module 14, e.g., wirelessly. The activity module 14, as noted above, can recognize different types of activity, such as aerobic, intense aerobic, weight training and intense weight training, as disclosed above and in further detail herein below.

The activity circle 38 can represent the expected activity of a user, e.g., based upon the history of the amount and type of activity performed by the user. If the behavior of the user changes, the amount of activity needed to fill the activity circle 38 can be changed. No individual has the same level of activity from day to day. The application 12 can adjust the user's food allowance throughout the day based upon what activity can be expected and what has actually occurred. The activity circle 38 can fill up at different rates, for the same number of activity units, for different users. In other words, the rate for filling the activity circle 38 for any given exercise can be variable for each user and also can be partly or fully based on a learned activity pattern learned by the application 12, based upon the prior behavior of the user. In an embodiment, should the user conduct more activity than the application 12 historically expects, the activity circle 38 can display progressive series of colors indicating the amount of activity increase. Changes in the activity circle 38 can have an immediate impact on the fitness arc 34.

Any prediction made in determining the fitness arc 34 (i.e., the calculation of an energy deficit/energy excess) may be confirmed through the input of the user's daily (or other periodic entry) actual weight. If the prediction by the system 10 is incorrect, the system 10 can adapt to the user's circumstances. For example, if the user underestimates the indicated food intake portions, the user may gain weight, even though the fitness arc 34 indicates an amount on the energy deficit side 34a of the fitness arc 34. As disclosed above, the application 12 can recognize this and make adjustments that enhance the accuracy of the fitness arc 34 accordingly. Similarly, if the user does not burn calories as rapidly as initially predicted (and therefore an initial prediction by in the energy deficit portion 34a may result in an actual energy excess), the application 12 can recognize this and adjust the fitness arc 32 accordingly.

The units which describe activity and food choice can be specific to each user, and can be learned for each individual and adjusted daily. For example, they can be different from the conventional food caloric units, which can be used as measurement of physical activity, or the unit of energy liberated in heat generation from a specific food. The food calorie units can be entered into the application 12 initially, but the units change as they can be measured against other variables, and they can be assigned a unique user specific number within the algorithm. There can be constants assigned to the user, e.g., which represent intrinsic metabolism, but this number can be recalculated as food icon selections, activity and fitness affect the user's actual and changing level of intrinsic metabolism.

The application 12 can consider metabolism as the efficiency with which the user utilizes stored and consumed calories and therefore represents an element of the energy balance. Thus calories assigned to food or activity for example, can be different from those assigned from existing data bases, but instead can be defined by the way in which the user inputs data and the way the data as input interacts to establish the metabolic constant calculated by the application 12. The values assigned can be recalculated based upon their ability to accurately predict weight gain or loss. The fitness arc 34 can represent a real time presentation of the system 10 assessment of the energy balance. In an embodiment, the fitness arc 34 periodically updates (e.g., every 10 minutes) and displays the energy balance relationship between food, activity and metabolism. As described hereinabove, at the end of each day, the fitness arc 34 data can be assigned a final value which then can be represented by the green, red, or black dot 36. The ratio or proportion of the color coded dots 36 over, for example 7 days, can visually inform the user as to whether there can be an expected weight loss or gain during a particular week. The algorithm thus creates an ongoing user profile of intrinsic metabolism, activity, food choice and food amount that can be unique to each user.

Continuing to refer to FIG. 6, a colored diamond-shaped pointer 40 can be movable along a line that represents a range of a health quotient 42. The health quotient 42 can be derived from the running average of the fitness arc value 34c for each day of a month modified by the food type consumed and the user's weight. The health quotient 42 can include the user's present weight and desired or targeted weight (i.e., via direct input), the quantity and type of food consumed (i.e., based on the user's selection of food types and quantities). The health quotient 42 also can include the aerobic activity of the user (such as running) and anaerobic activity (such as resistance training for muscle enhancement) which can be automatically input into the application 12 by the activity module 14 as disclosed in more detail below.

In an embodiment, the health quotient 42 can be a graphic representation of a single point on a horizontal scale of the health and fitness of the user as referenced against his/her goals and profile. The health quotient 42 can be contrasted to the fitness arc 34, which can be a measure of daily energy balance, because it places the user on a scale of fitness and health based on data accumulated over longer periods, e.g., one month. The determination of health can be not culled or determined from a demographic reference point, but instead determined for each user based upon parameters defined in the application 12 (i.e., target weight, calculated intrinsic metabolism, food type and quantity consumed, the rate of change in weight gain or loss of the user, exercise and activity units level, etc.). The health quotient 42 calculation can incorporate the directionality of measured values and inputs for the user to establish health status. The health quotient 42 also can be given limitations as to its positioning on the scale based upon indicated weight goals. Specifically, the overweight individual (defined in the user profile input screen 24 by a targeted weight goal less than actual weight) could be restricted from a pointer 40 position on the fit zone of the health quotient 42 horizontal scale. The location of the pointer 40 on the horizontal scale can also be determined by historic data from the user as well as daily updates which, when formatted by application 12, define the health quotient 42. The horizontal scale can be a range of units for all users allowing for standardization and comparison among individuals and groups, but the data and profile for each user defines the degree of movement on the scale conferred by the various parameters of the algorithm(s) used in the application 12. In other words, the scale can be constant across all users, but the amount of change or movement on the scale per calculated value(s) of the application 12 parameters can be different for each user. Thus the user can set individual goals, but where the pointer 40 can be positioned on the health quotient 42 scale can be based upon the application 12 algorithms' calculation of the user's specific metabolic profile.

As disclosed above, the starting weight 24b and target weight 24d can be input on the user profile input screen 24 (see FIG. 3). Based on these inputs, one of two conditions can be possible: i) the user can be over weight (i.e., the starting weight can be greater than the target weight), or ii) the user can be at or under the target weight. These two possibilities can be used to govern the health quotient 42. More particularly, in an embodiment, when the health quotient 42 is calculated at the end of each day, the pointer 40 can be positioned in a manner described below.

The health quotient 42 horizontal scale can range, e.g., from −50 units at the left end to +50 units at the right end, although the numerical values for the units are not shown on the scale on FIG. 6. Each month, a running average of available health quotient 42 daily results can be compiled and displayed. When moving from one month to the next, the first day of each month can be equivalent to the final figure from the previous month, and it can be weighted as only one day of that month. As shown in FIG. 6, the horizontal scale can be divided into four portions moving left to right. The first portion extends from −50 to −25 and can be labeled "fit", the second portion extends from −25 to 0 and can be labeled "healthy", the third portion extends from 0 to +25 and can be labeled "unhealthy"; and the forth portion extends from +25 to +50 and can be labeled "health risk". In an embodiment, each portion may have color coding varying from "fit" to "health risk" such as dark green, green, yellow, and red, respectively. The position of the pointer 40 on the horizontal scale can be used to represent, at the end of each day, that month's average of health quotient 42 values over the available days in the month. Furthermore, the health quotient 42 units can be the fitness arc values 34c of the fitness arc 34 at the end of each day, e.g., as modified in a manner described below.

In an embodiment, the health quotient 42 may also account of the distribution of the calories consumed thought the day. More particularly, the waking hours are divided into four quadrants. If 20 percent of the total food consumption is consumed in each of the four quadrants, then the pointer 40 will shift to the left by three units, and if not, it will shift to the right by three units. The remaining 20 percent can be consumed in any of the four quadrants without effecting the health quotient 42.

In the circumstance where the user is over weight (i.e., the starting weight can be greater than the target weight), the pointer 40 can point to a point to the left of −24. The user could thus be in the "healthy" range but not in the "fit" range. Food selection can also modify the final number. Each food item can be assigned a color: for example red for poor quality, yellow for neutral quality, and green for high quality food. Further, when consumption of 51% of food is good quality or poor quality then the following modifiers can be activated, and if consumption of either the good or poor quality food does not reach 51%, then these modifiers may not be activated. The modifiers and their triggers can be:

If 51 percent of food consumption is "good quality" and the user is overweight then the final fitness arc 34 can have negative, e.g., 12 units added to fitness arc value 34c and the pointer 40 can be shifted to the left. If 51% of food consumption is poor quality, then the pointer 40 can be shifted to the right, e.g., by 12 units.

If the user is at or under target weight and 51% percent of food consumption is "good quality" then the pointer 40 can be shift, e.g., (50+12) or 62 points to the left. If 51% of food consumption is "poor quality", then, as described above, the pointer 40 can be shifted, e.g., to the right by 12 units.

The system 10 can also reference food intake with change in the user's weight and fitness activity to develop the user's intrinsic metabolism. As described above, the system 10 may adjust the prediction of changes in the health of the user on a daily basis based on input values from the user regarding weight, food intake and fitness activity.

In an embodiment, a summary of each month's health quotient 42 may be displayed (not shown). For example, the display may provide a listing such as: i) January—fit, ii) February—unhealthy, etc.

Figure 7A:
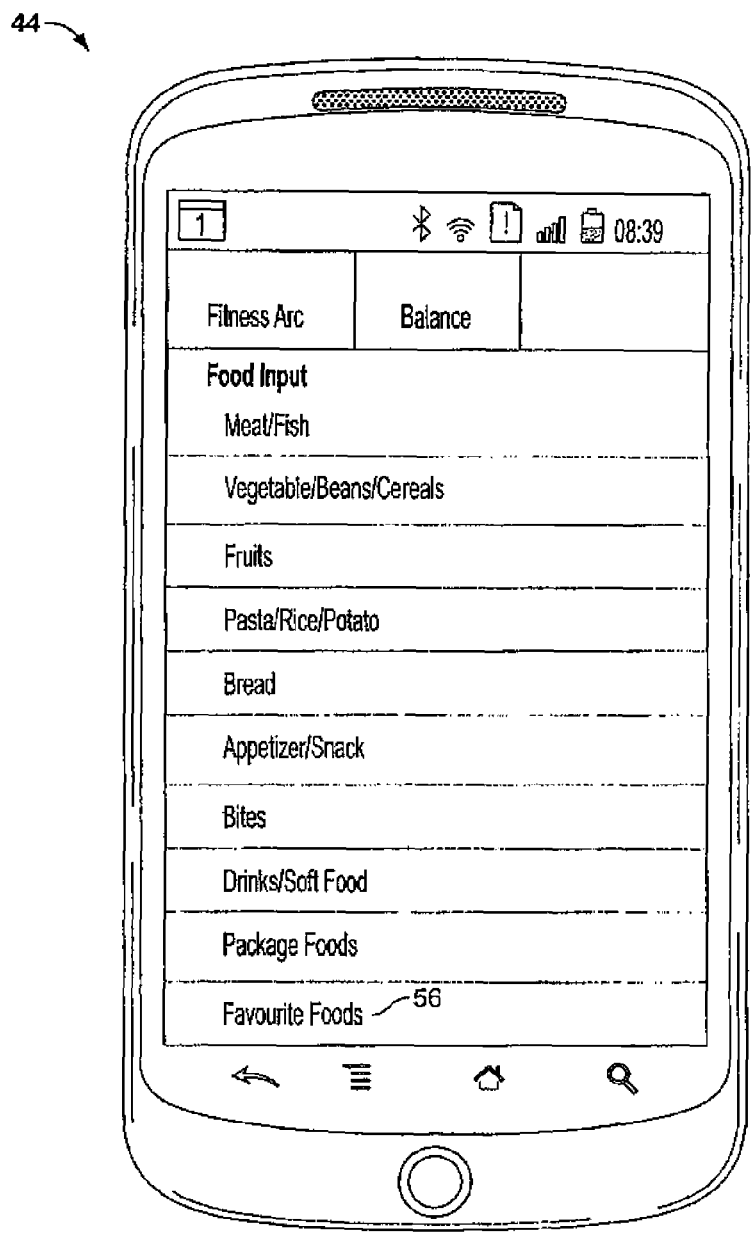
FIG. 7A shows a user food choice input screen.
Figure 7B:
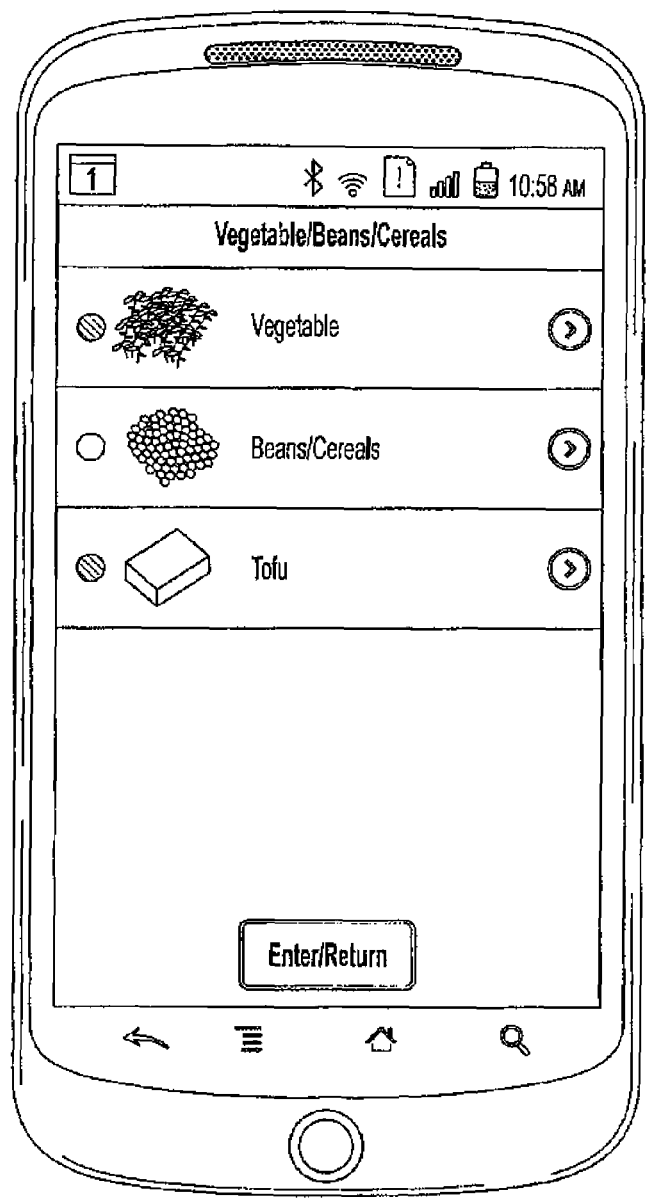
FIG. 7B shows an another user food choice input screen.
Figure 7C:
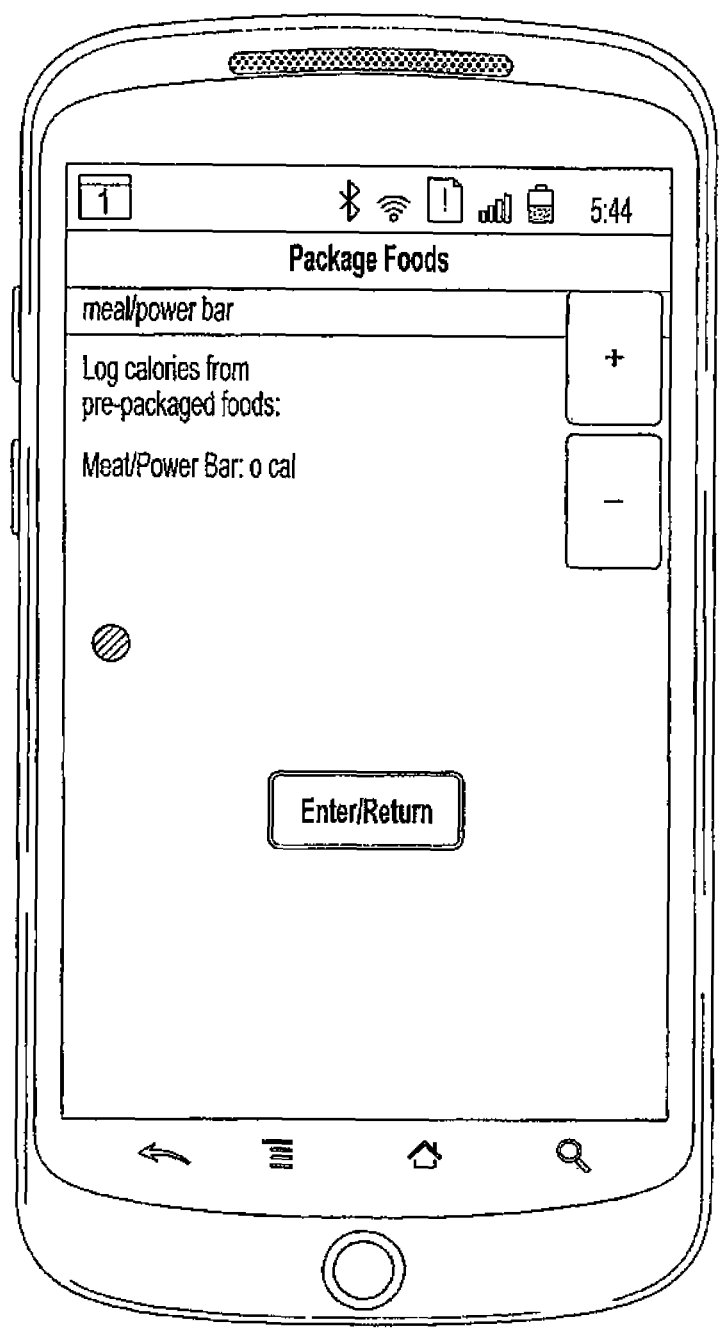
FIG. 7C shows an another user food choice input screen.

Referring now to FIGS. 7A-7C, as described above, when a user consumes foods, it may not be necessary for the user to directly input the number of calories. Instead, the user may select the type of food consumed from a listing 44 as shown in FIG. 7A and further defined in the listing shown on the screen as indicated by way of example in FIG. 7B. In an embodiment, the application 12 may learn the user's most frequently chosen or consumed food choices, and compile the same under a tab on the listing 44 (see FIG. 7A "favorite foods" tab 56). A dietician can review the listing 44 and repopulate it. When the user can read calories off a food package, the item may be entered directly on the screen depicted in FIG. 7C. In such instances, the food percentage of protein, fat, etc. components may be provided by the application 12 for such items, based on the normal distribution of these components for such items. In an embodiment, the listing 44 may include items such as deserts and junk food (not shown).

Figure 8:
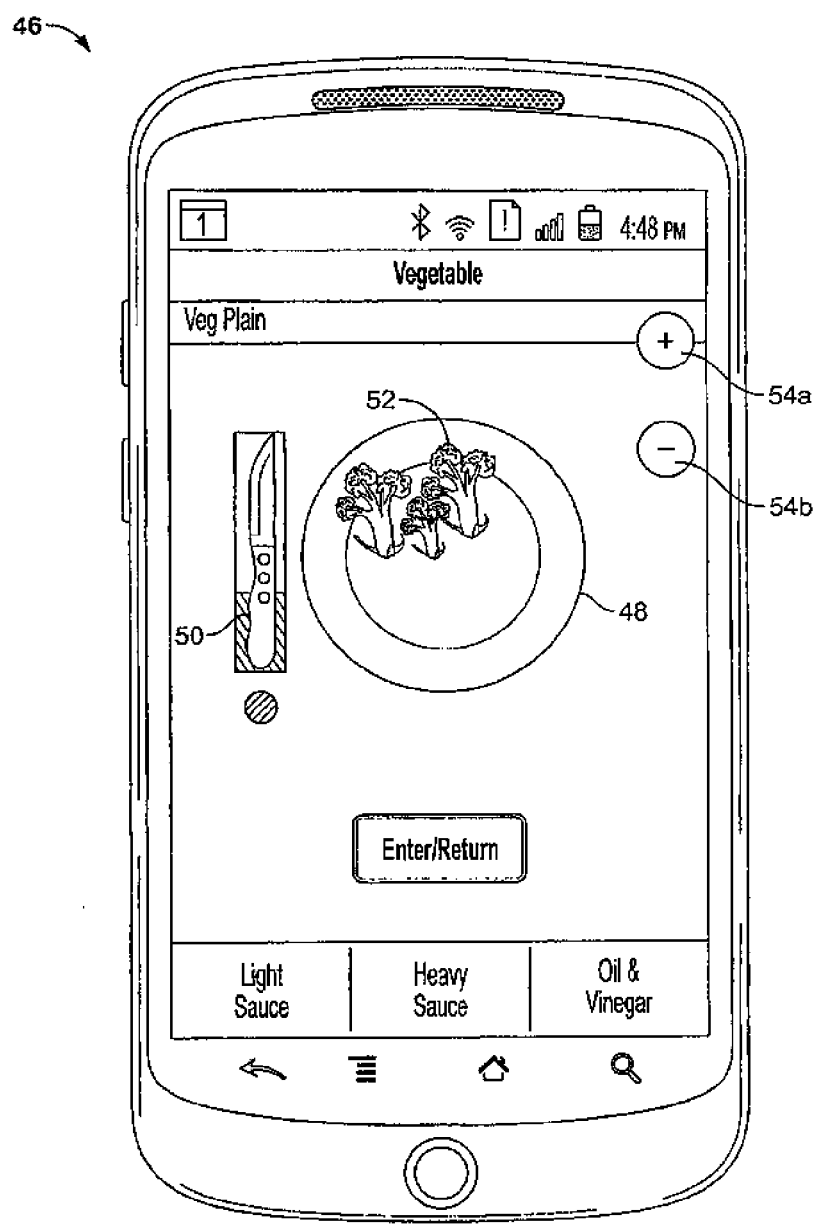
FIG. 8 is a user food portion input screen.

Referring to FIG. 8, in an embodiment, once a type of food is selected, a portion screen 46, including a plate 48, can be displayed. FIG. 8 also depicts a knife 50, or some other utensil for a size reference. The user may place more or less food 52 on the plate 48, e.g., with portion control buttons 54a, 54b. In an embodiment, the knife 50 can fill with a color scheme which depends on the portion size of the food 52, where the degree of coloring of the knife 50 equates with the degree of filling of the food circle 20 (FIG. 2) allowance. This can allow the user to visually input the type and portion of food, without the need of measuring, weighing or knowing the caloric content of the food. In an embodiment, the listing 44 may include an option for the user to input (e.g., download) a new food item(s) on the listing 44. The user may also manually directly input a caloric intake item.

In an embodiment, the user may enter a "proposed" meal to determine the meal's effect on the user's fitness goals. The user may then edit the proposed meal or change the proposed meal into an actual meal, e.g., after the meal is consumed. In an embodiment, the impact of the proposed meal on the user's food and caloric balance can be demonstrated by the knife 50 progressively filling with a color scheme which matches the color scheme and the degree of filling of the plate 48. Thus before the user enters the content of the meal into the application 12, the effect of the proposed meal can be seen by reviewing how much color the knife 50 has filed in. Reducing a food portion size can decrease the percentage of the knife 50 coloring. A fully colored knife 50 can be used to correspond to a fully colored food circle 20.

Figure 9:
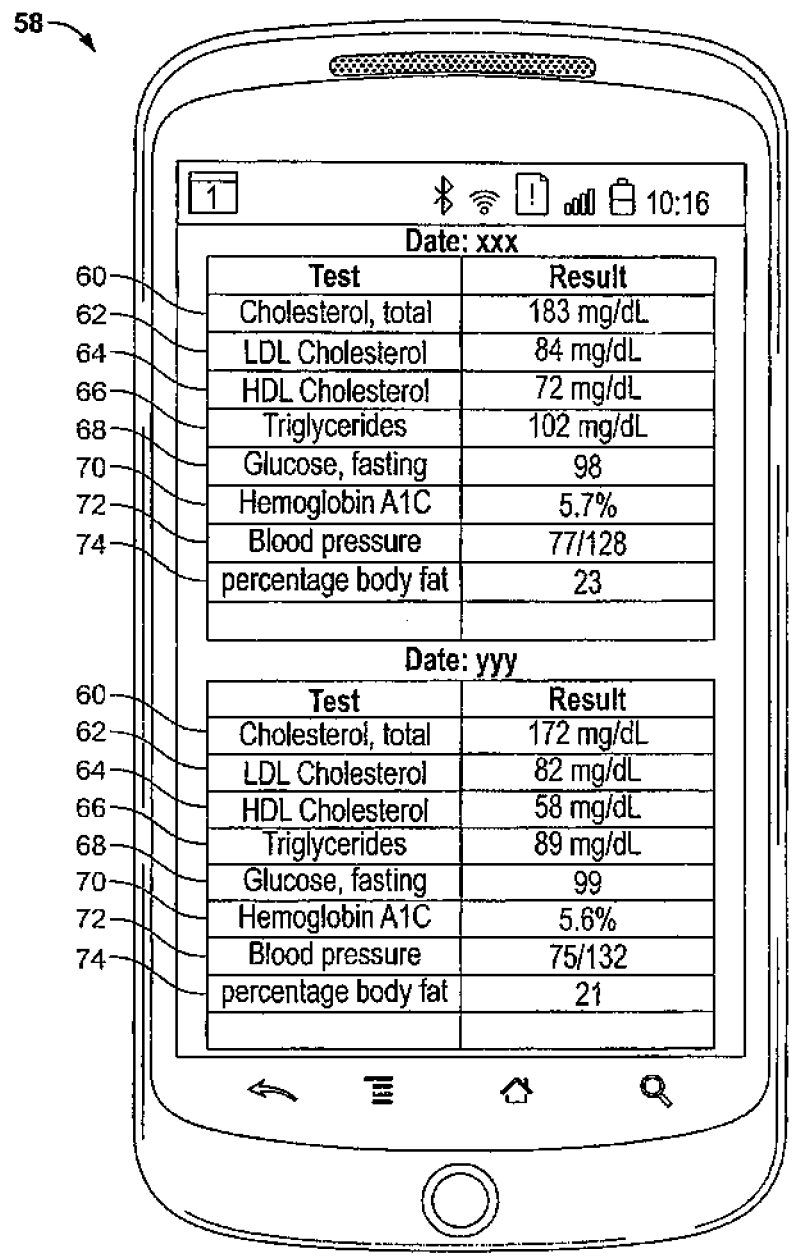
FIG. 9 is a user test results input screen.
Figure 10:
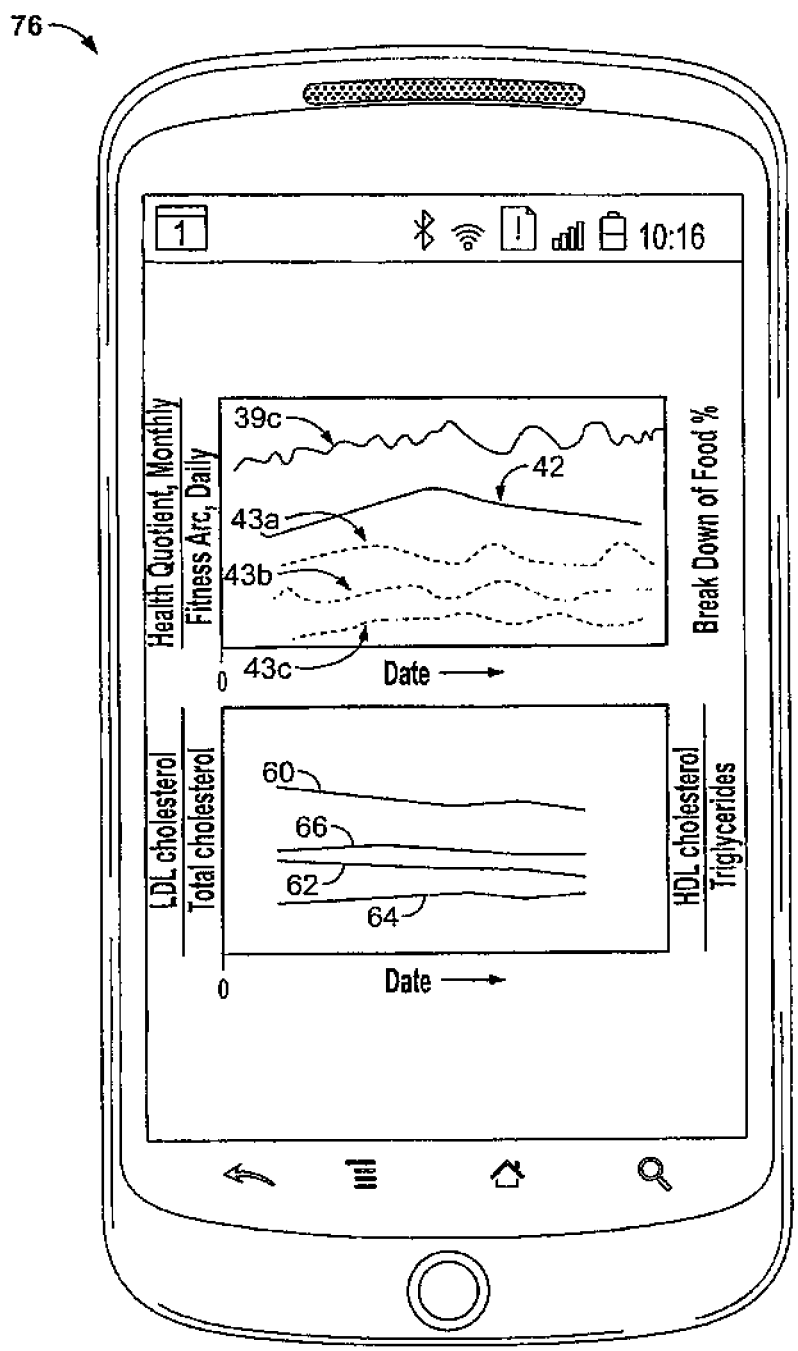
FIG. 10 is a screen showing a graph of user test results over time.

In an embodiment, in addition to accumulating and displaying fitness and health related data generated by the application 12, the system 10 can facilitate accumulating and displaying externally generated fitness and health related test results, thereby serving as a focal point for accumulating, storing and displaying all fitness and health data related to the user, not just the data provided by system 10. For example, test results may be periodically input in the application 12 by the user on a test results record screen 58 shown in FIG. 9. In an embodiment, FIG. 9 includes data on total cholesterol 60, LDL cholesterol 62, HDL cholesterol 64, triglycerides 66, fasting glucose, 68, hemoglobin A1C 70, blood pressure 72, and percentage body fat 74. It can be understood that other test results data may also be included in the test results records 58. The application 12 can then utilize the test results record screen 58 data to form historical graphs or histograms. For example, FIG. 10 depicts a graph or histogram 76, which shows total cholesterol 60, LDL cholesterol 62, HDL cholesterol 64, and triglycerides 66 blood test results for the user taken at various dates. Further, since energy excesses 34*b* may raise cholesterol levels, energy excesses 34*b* may be calculated and displayed (not shown) on the histogram page 76.

Figure 11:
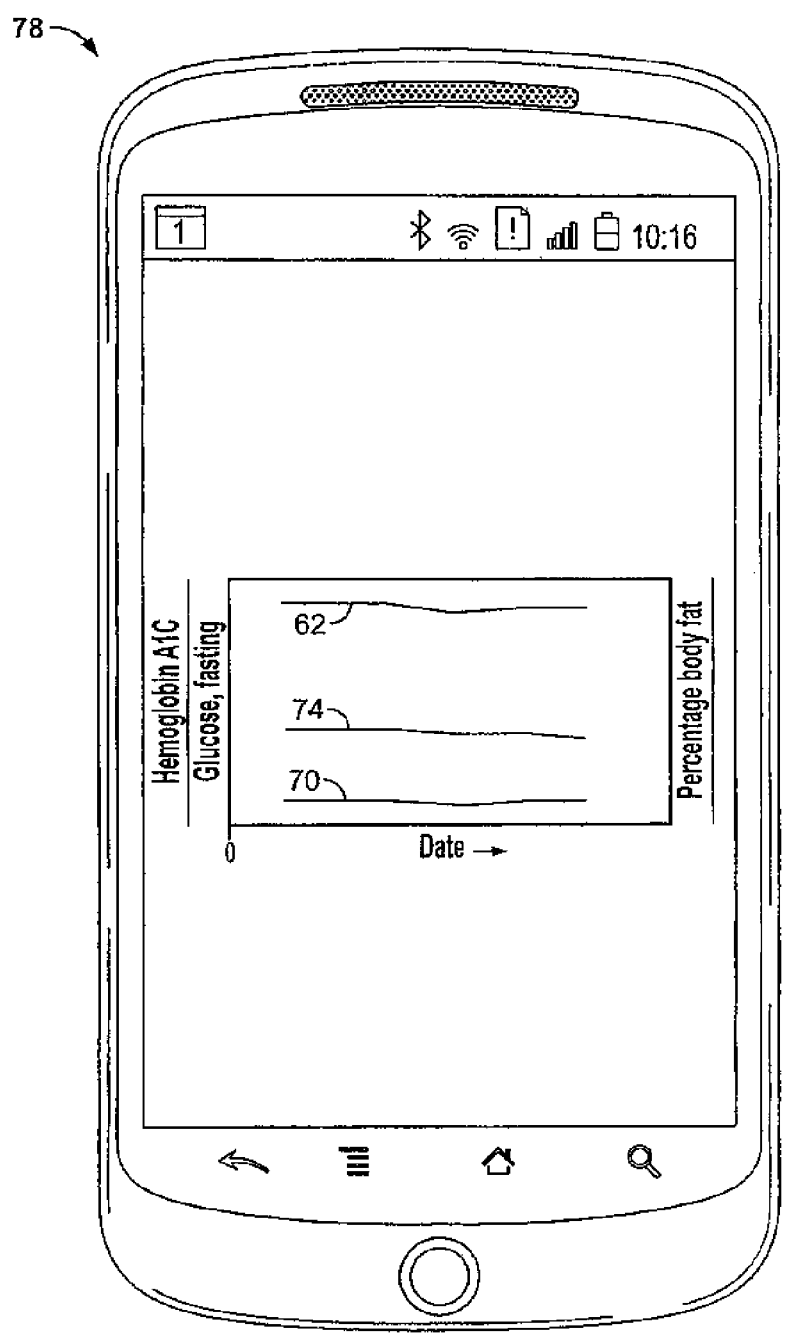
FIG. 11 is a screen showing another graph of user test results over time.

Referring to FIG. 10, in an embodiment, the system 10 can generate parameters such as the fitness arc value 34*c*, the health quotient 42, and the breakdown of food percentage 43*a*, 43*b*, 43*c*, etc., which may also be displayed in the histogram 76, to show correlations between the system 10 derived parameters and the externally derived test results (e.g., total cholesterol 60, LDL cholesterol 62, HDL cholesterol 64, and triglycerides 66). In an embodiment, FIG. 11 there is illustrated, by way of example, a histogram 78 for displaying test result measurements such as fasting glucose 68, hemoglobin A1C 70, and percentage body fat 74 over time. The system 10 may also generate other histograms (not shown) for displaying, e.g., the percentages of protein, fat, and carbohydrates, so that the food choice percentages utilized by the user and their trends over time can be also readily apparent to the user.

In an embodiment, the system 10 can facilitate accumulating and displaying data that can be related to health conditions that are being medically treated by the user. For example, Coumadin is a blood thinner prescribed to patients with a propensity to form blood clots in the vascular space. Such patients must monitor their intake of vitamin K (Vit K), which diminishes the effectiveness of the blood thinner. Vit K is known to occur in certain foods such as vegetables. The diet for patients on Coumadin therapy may be not focused on Vit K avoidance, but rather it can be based on the consumption of the same amount of Vit K each day.

Figure 12:
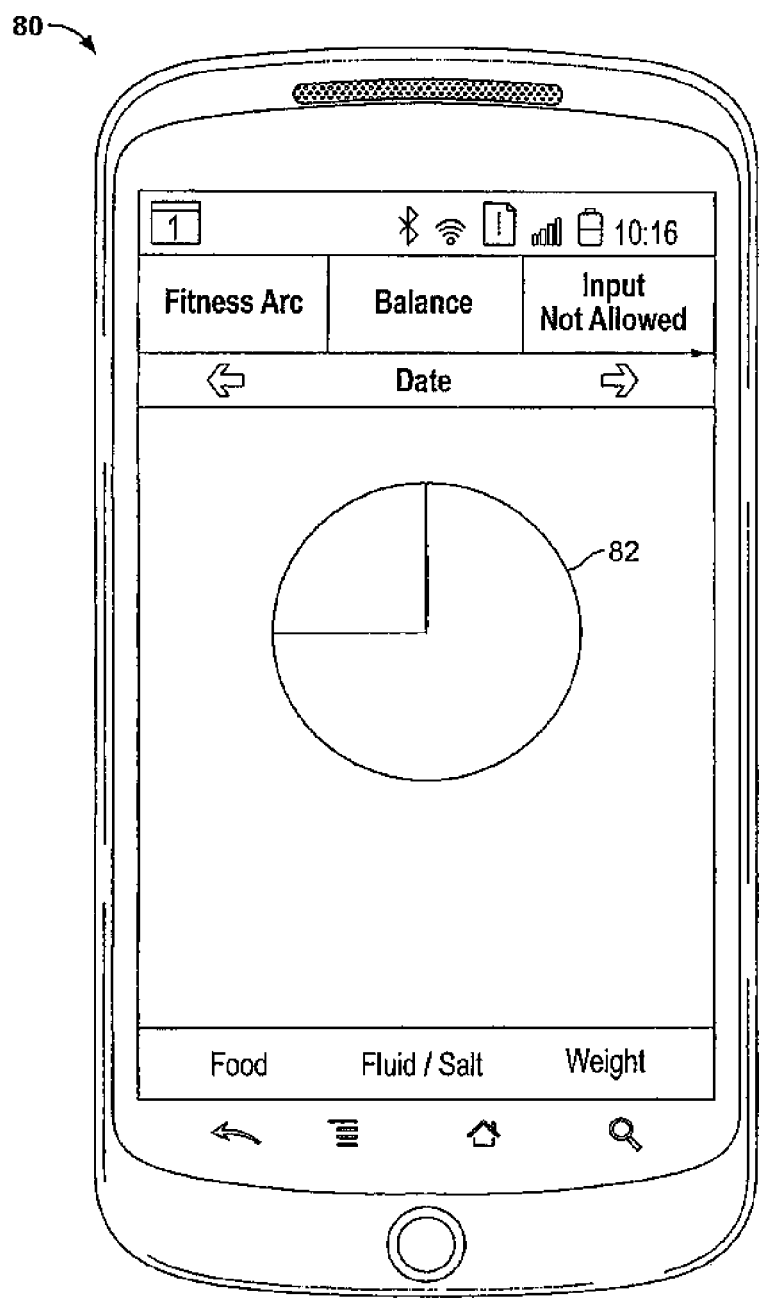
FIG. 12 is a screen showing a graphical circle that indicates the proportion of Vitamin K daily allotment consumed by the user during the day.

Referring to FIG. 12, Vitamin K chart 80 includes a Vit K circle 82 which can provide a graphical representation of the user's daily consumption of Vit K. If the diet of the user fills the Vit K circle 82 the same amount each day, then the effectiveness of the Coumadin therapy can be maintained. The Vit K circle 82 functions in much the same manner as the activity circle 38, and it can be learned for each user. The application 12 can learn and then stores a weekly average value of Vit K units which serves as a record of the user's Vit K units consumption behavior. The Vit K circle 82 may fill with green color as the units are accumulated toward the weekly average. More particularly, a numerical value of 1, 2, or 3 Vit K units can be assigned to each vegetable in order to describe its Vitamin K level. For example, if the user ate 100 calories of food assigned the numerical value of 1 Vit K unit, the application 12 could register 100 Vit K units on Vit K circle 82. If the user consumed 100 calories of food assigned the numerical value of 2 Vit K units, then 200 Vit K units could be registered on the Vit K circle 82.

The user can choose, on the profile input screen 24, whether to display a circle depicting whether the food consumed includes the total daily vitamin requirement or Vit K alone. The Vit K circle 82 may also fill with a green color (denoting a full daily allotment of Vit K has been reached), a yellow color (denoting a full daily allotment of Vit K I is being approached), or a red color (denoting a full daily allotment of Vit K I has been exceeded). In an embodiment, the Vit K circle 82 may alternately be displayed adjacent to the fluid and salt circles 26, 28 on FIG. 4 (not shown in FIG. 4).

Figure 13:
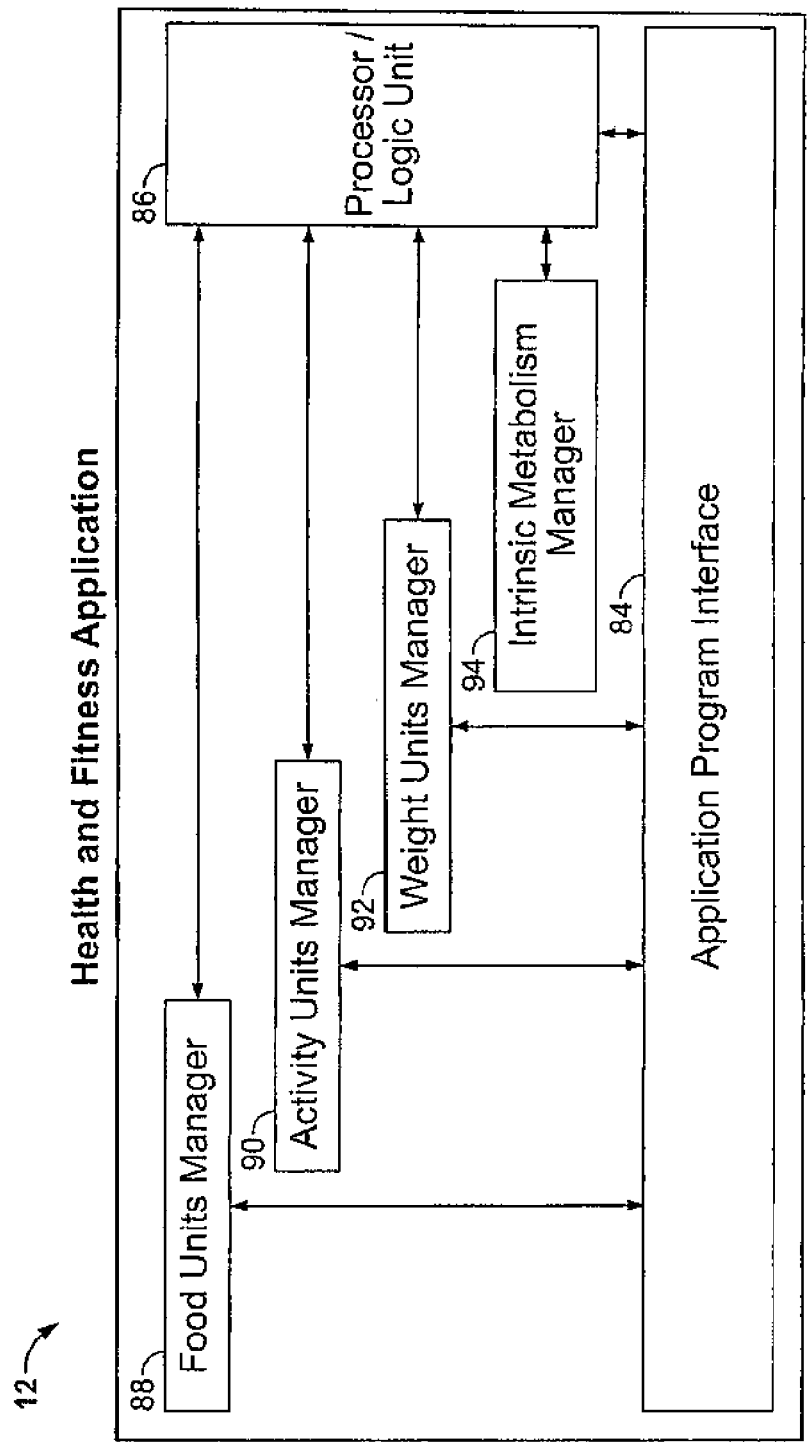
FIG. 13 is a schematic diagram of the health and fitness application.

Referring now to FIG. 13, as described above, the application 12 can include software algorithm codes for displaying data, calculating data, receiving data etc. In an embodiment, the application 12 can include an application algorithm interface 84 which can facilitate the interactions between the digital device D and the application 12 in a predetermined (e.g., standardized) manner. For example, the application algorithm interface 84 can enable the application 12 to utilize the conventional services and functions of the digital device D, such as i) the central processing unit, ii) the input/output interfaces (e.g., touch screen, keyboard, mouse, etc.), and iii) the Bluetooth™ transceiver. In this way, the software algorithm codes of the application 12 may employ these services to receive data, display data, and calculate using the data, etc. In an embodiment, the application 12 can be functionally organized around a processor/logic unit (computing device) 86 that can be connected to a food units manager 88, an activity units manager 90, a weight units manager 92, an intrinsic metabolism manager 94, and the application algorithm interface 84.

In an embodiment, the food units manager 88 and the weight units manager 92 can be interacted with the user via the user interface of the digital device D, and the activity units manager 90 can interact, e.g., wirelessly, with the activity module 14, e.g., via the Bluetooth™ channels BT1 and BT2. The results of the food units manager 88, the activity units manager 90, and the weight units manager 92 interactions can be input to the processor/logic unit 86 wherein the application 12 can periodically run the energy balance calculation and formulate the intrinsic metabolism and provides the same to the intrinsic metabolism manager 94. In the manner described above, the intrinsic metabolism manager 94 can assess the accuracy of the processor/logic unit 86 formulated predicted weight to that of the inputted actual weight of the user. Should the formulated/predicted weight be significantly different than the actual weight of the user, the intrinsic metabolism manager 94 can, e.g., direct the processor/logic unit 86 to formulate an adjustment, e.g., to coefficients provided to the food units manager 90 for adjusting the food unit values or to the activity units manager 90 for adjusting activity units as is further discussed below.

Figure 14A:
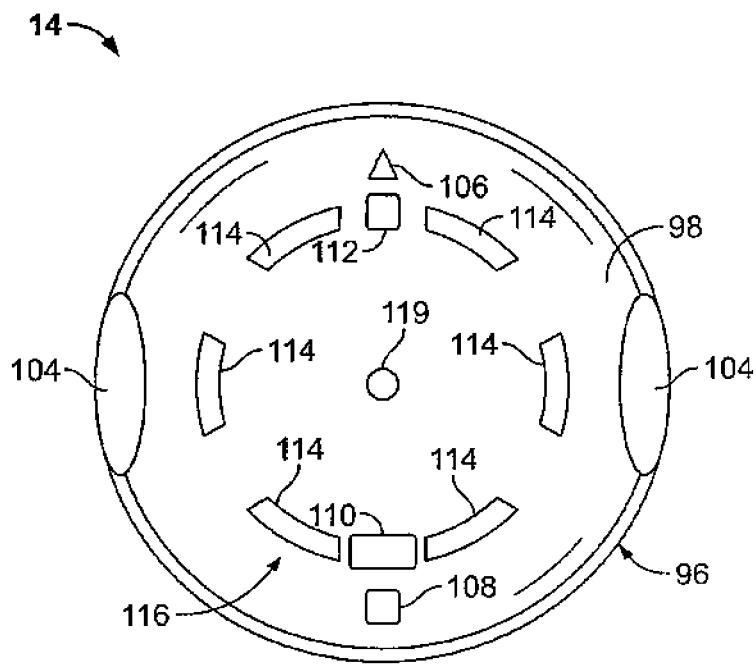
FIG. 14A is a plane view of the activity module.
Figure 14B:
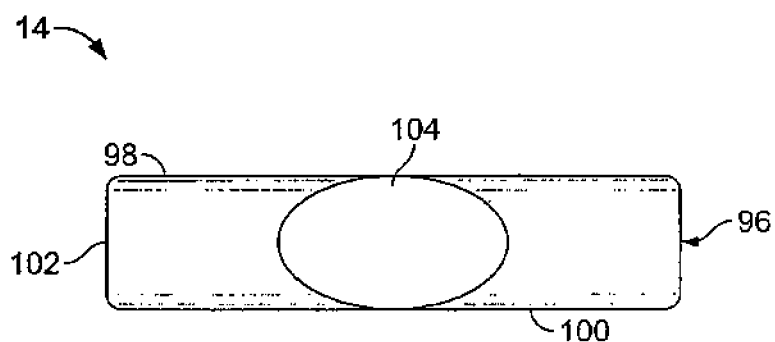
FIG. 14B is an side view of the activity module.

FIGS. 14A and 14B depict the activity module 14 which, when it can be worn by the user, can produce and stores activity units that can be conveyed, e.g., wirelessly, to the application 12. More particularly, the activity module 14 can be contained in a disc-shape housing 96 which can have a face 98, a bottom 100 which can be positioned opposite the face 98, and a cylindrical-shaped side 102 which extends between the face 98 and the bottom 100. In an embodiment, the bottom 100 may be releasably attached to the side 102 (e.g., threaded or clipped thereto) to facilitate the fabrication of the module 14 as well as, e.g., the replacement or recharging of batteries. The housing 96 may be made of plastic or other suitable material such as stainless steel. The activity module 14 may have a Bluetooth™ connection to application 12 of the system 10.

In an embodiment, the housing 96 can a plurality of indicators and buttons. More particularly, two buttons 104 can be positioned opposite each other on the side 102 of the housing 96. The user may turn the activity module on and off, e.g., by simultaneously pressing the buttons 104 with the thumb and forefinger and briefly shaking the activity module 14. The activity module 14 can shut down when it comes to rest for a selected period of time and can turn on when it senses motion. In an embodiment, both buttons 104 must be pressed simultaneously for all operations that require input from the buttons 104. An arrow-shaped pointer 106 can be located on the face 98 of the housing 96, for purposes disclosed below.

In an embodiment, the activity module 14 has magnets 108, 112 and an indicator light 110 that can be illuminated to indicate a low battery charge. The arrow shaped pointer 106 may also signal that the activity module 14 has the proper orientation in an exercise band 118 (FIGS. 15A, 15B), e.g., to record an aerobic exercise monitoring mode or a weight training exercise monitoring mode, which can be disclosed below.

In an embodiment, the activity module 14 can have a plurality of activity lights 114 which can be positioned on the face 98 of the housing 96, e.g., in a circular pattern to form an activity circle 116. The activity lights 114 e.g., can be progressively lit up during the day to indicate the user's progress in achieving his/her daily goal for activity units. A blinking activity light 114 can indicate that the activity units goal attributed to that particular activity light 114 has not yet been achieved, and a steadily illuminated activity light 114 can indicate that the activity units goal associated with the activity light 114 has been achieved. The activity circle 116 goal can be the number of activity units that can be required to be achieved by the user in the day to maintain his/her weight, or to be exceeded to lose weight, or to be under-achieved to gain weight and each of the activity unlit lights 114 in the activity circle can represent a percentage, e.g., 25% of this amount. In other words, the activity circle 116 activity units' goal can be also equal to the sum of each of the activity light's 114 activity units goal.

Assuming that the food intake is in a specified range, should the activity unit exceed expected levels, the daily food allowance can be increased as represented in the food circle 20 (FIG. 2). The object for the user can be to light up all the activity lights 114 during the day. The activity units circle 116 goal can be the same as that which can be applied to the activity circle 38 depicted in FIG. 6. The activity circle 116 goal, which can be calculated by the application 12, can be transmitted to the activity module 14 from the digital device D via the channel BT2. The number of activity units accomplished by the user at any given time in the day may be transmitted from the activity module 14 to the digital device D via the channel BT1. The activity module 14 can update its activity circle 116 independently from the application 12, once the activity module 14 has been informed by the digital device D how many units are required to illuminate all of the activity lights 114 of the activity circle 116. The transfer of activity units' data can be accomplished during a synchronization process which is discussed below.

In an embodiment, the user can synchronize the activity module 14 with the application 12, e.g., by pressing and holding the buttons 104 and double shaking the activity module 14. The activity module 14 can be then positioned within five feet of the digital device D, and the Sync tab located below the fitness arc 34 (see FIG. 6) can be then pressed. During the synchronization process, i) the activity units goal that has been calculated by the application 12 can be transmitted to the activity module 14 from the digital device D via channel BT2, and ii) the activity circle 38 of the application 12 can fill with accumulated activity units that can be transmitted to the digital device D by the activity module 14 via channel BT1. The user may synchronize the activity module 14 with the application 12 as many times as desired throughout the day, but preferably at least once a day.

In an embodiment, the activity module of the described invention can include a processor, a motion sensor, a timer and a rechargeable battery. In another embodiment, the motion sensor is an accelerometer. In another embodiment, the accelerometer is a triaxial accelerometer.

In an embodiment, the activity module can be programmed to alter the performance of the processor and the accelerometer to track different examples of motion. Such examples of motion include, but are not limited to, movements associated with sleep, walking, jogging, running, weight lifting, biking, yoga, Pilates, circuit training, resistance training, elliptical training, tennis, basketball, soccer and the like.

In an embodiment, the environment of the motion sensor, e.g., accelerometer, can be engineered (i.e., placed) in different orientations within a magnetic field to change the performance of the motion sensor, e.g., accelerometer, for the specific category of motion being performed. This engineered magnetic environment can exclude certain movements of the motion sensor, e.g., accelerometer, not associated with a particular activity. Activities include, but are not limited to, sleep, walking, jogging, running, weight lifting, biking, yoga, Pilates, circuit training, resistance training, elliptical training, tennis, basketball, soccer and the like. The engineered magnetic environment can allow for the segregation of various types of activity into analyzable units.

In an embodiment, the described invention provides a system in which a user can place the activity module into pre-specified positions inside a magnetic field. The magnetic field is created, for example, by magnets contained within a receptacle (e.g., a pouch, a pocket, etc.) connected to a means for attaching the activity module to the user (e.g., a band, a strap, etc.). The performance characteristics of the activity module can be programmed to detect a specific type of motion while excluding movement which characterizes other forms of activity. The activity module can be programmed, for example, by operating buttons located on the activity module, by a command transmitted via Bluetooth™ from a device, which includes but is not limited to, a communication device, a network device, a personal digital assistant, a mobile communication device, whether or not able to download and run applications from the communication network, such as the Internet, e.g., an I-Phone®, Blackberry®, Droid™ or the like, a manufacturing tool, or any other device including a computing device, comprising one or more data processors, etc., or by orienting the activity module in various positions inside the magnetic field.

In an embodiment, the described invention provides a combination of a user activated switch and magnetic field to institute programming changes to alter the functional status of a motion sensor, e.g., an accelerometer, into different activity monitoring modes. Activity monitoring modes include, but are not limited to, a standard mode ("S") selected for routine daily activity, a running/jogging mode ("A+"), a bicycle riding mode ("A"), a weight lifting/resistance training/yoga mode ("W+"), an aerobic-based gym equipment (e.g., elliptical) mode ("W") and a sleep activity mode. By programming the motion sensor, e.g., accelerometer, into an activity monitoring mode, the motion sensor, e.g., accelerometer, can distinguish and record the types of movement associated with a particular activity and exclude the types of movement not associate with a particular activity.

In an embodiment, the deflections recorded by the motion sensor, e.g., accelerometer, do not need to be interpreted at an application interface to determine what type of activity or what type of motion produced a specific deflection. In another embodiment, motion algorithms are not needed to determine what type of activity or what type of motion produced a specific deflection. Instead, the movement that characterizes the activity is itself characterized in terms of, for example, timing, direction, acceleration and a multiplier.

Positioning the activity module inside the magnetic field can enable the activity module to distinguish activities (e.g., walking, weight lifting, jogging, running, yoga, and bicycle riding) from one another. By way of example, movement which characterizes weight lifting is different in timing, direction and acceleration from walking or bicycle riding. Orienting the activity module in various positions inside the magnetic field can allow for the recordation of motion associated with one type of activity, while excluding movement which characterizes other forms of activity.

In an embodiment, movement in a particular magnetic field that is recognized by the activity module is assigned a multiplier. The multiplier can allow for the movements associated with one activity to be assigned a weighted value that is different in magnitude from other types of activity. By way of example, the multiplier assigned to movements associated with bicycle riding is different than the multiplier assigned to movements associated with walking, which is different than the multiplier assigned to movements associated weight lifting, which is different than the multiplier assigned to movements associated with sleep.

Deflections (also known as counts or clicks) recorded by the motion sensor, e.g., accelerometer, for each type of movement are saved and segregated by activity type in the activity module processor. The information saved and segregated by the processor is used by the activity module software to determine, for example, the amount of relative energy expended by the user during a given time period in each of the modes of activity. For example, the activity module can determine how much relative energy was expended weight lifting versus walking versus running, etc. This information can be transferred, for example, via Bluetooth™ to a device such as a smart phone that contains software for further processing. After such processing is complete, the activity module can receive further programming instructions which in turn can further update the activity module's displays.

In an embodiment, the activity module can be sent commands via Bluetooth™ in order to change performance of the activity module independent of the magnetic field. Commands include, but are limited to, turning the activity module on/off, changing the sensitivity of the activity module, changing the mode of activity and the like.

In an embodiment, the activity module includes at least one magnetic field detector component. In another embodiment, the magnetic field detector component is a Hall effect sensor. In another embodiment, the Hall effect sensor can be connected to a processor. In another embodiment, the Hall effect sensor transmits a signal to the processor when a magnetic field is detected. The signal transmitted by the Hall effect sensor to the processor, for example, can cause the processor to change the way it interprets signals transmitted from a motion sensor, e.g., an accelerometer, and can cause the processor to adjust the way the motion sensor, e.g., accelerometer, captures movement.

In an embodiment, magnetic field orientation is recognized by a processor which transmits a signal to a motion sensor, e.g., an accelerometer, via firmware (also known as software). The signal changes the parameters under which the motion sensor, e.g., accelerometer, reads, collects and reports data. A combination of orientation of the activity module within a magnetic field and the presence or absence of switch activation on the activity module results in the reprogramming of the activity module by the processor to a set of pre-specified values stored in the processor. These pre-specified values aid in defining the intensity of work associated with each motion sensor, e.g., accelerometer, deflection for any given activity.

In an embodiment, the activity module includes a processor. The processor of the described invention can separately store deflections recorded during each of the programmed modes of activity. The activity module can communicate these stored deflections via Bluetooth™, for example, to an application residing on a device (e.g., mobile phone) for display either individually or in groups selected by the application to represent various forms of activity. The display can include, but is not limited to, what percentage of activity results from weight resistance training (i.e., to aid in muscle growth), what percentage of activity results from aerobic training (i.e., to improve athletic performance or lose weight), etc. The display can allow the user to regulate certain activities in order to select an optimal approach to obtain his/her fitness goals.

In an embodiment, the processor includes firmware (also known as software). The firmware of the described invention can be used to govern the relationship between the processor and the motion sensor, e.g., accelerometer. For example, the firmware can be used to change the parameters of function of the motion sensor, e.g., accelerometer, including, but not limited to, sensitivity, scale, detection time, count minimum and release time. The firmware also can be used to change the multiplier used by the processor.

In an embodiment, the firmware of the described invention can be used to determine the amount of effort expended in achieving a motion sensor, e.g., an accelerometer, deflection. For example, it is known that an accelerometer measures acceleration or the rate of change in speed over time but cannot measure effort or the speed at which any particular movement takes place. That is, the effort needed to change the acceleration of the activity module of the described invention cannot be measured by the accelerometer. It also is known that a smaller mass will accelerate faster with lower effort than a larger mass and that an accelerometer cannot measure this difference in effort. As such, a constant (i.e., multiplier) cannot be applied. However, when the activity module of the described invention is placed in an engineered magnetic environment in which the kind of acceleration to be recorded is pre-specified, then a value which is reflective of relative levels of effort can be assigned from one activity to the next. Various types of activity (e.g., running versus biking) generate a different pattern of acceleration cycles as the accelerometer moves through space. The accelerometer records the number of acceleration vectors it is programmed to detect. According to the described invention, the accelerometer data will not be rational if the user rides a bike with the activity module in the weight lifting position because the activity module would not count the rotation of the pedals with any regularity and for those it did count it would assign an inappropriate multiplier. An analysis of the accelerometer vectors as the activity module moves through space is not possible once the accelerometer deflection or count is generated. Thus, variance in accelerometer deflections or counts cannot distinguish the type of activity performed after it has occurred. In addition, the computational power needed to analyze the pattern of vector changes as they occurred would far outstrip the capacity of a device such as a mobile phone. Therefore, the described invention instead takes the approach that by pre-specifying movements, the deflections detected by the accelerometer are indicative of a specific activity. A multiplier can then be assigned at the level of the processor to indicate greater or lesser levels of effort (i.e. work); not because the accelerometer recognized the effort, but because the accelerometer was only allowed to record certain movements that typify certain types of activity. The movement between one activity and another may not be sufficiently dissimilar to allow the assignment of a multiplier reflective of the assumed effort. Activities with a similar pattern of movement are therefore grouped and the user is instructed to wear the activity module in the magnetic field (e.g., a strap or band comprising magnets). The magnetic field is detected by a Hall effect sensor, which in turn informs the processor that the movement recorded is a low or high effort activity. High effort activities can either be assigned a multiplier and/or the accelerometer can be programmed to register a greater number of accelerometer deflections or counts per unit time. When a triaxial accelerometer is used, data can be collected in a three dimensional manner as the accelerometer changes its vector angles when moving through space. For example, the accelerometer attached to the wrist when walking can have a similar pattern of motion through space as when jogging. Therefore, when walking, the accelerometer can be programmed to record fewer accelerometer deflections or counts for each stride forward than when running. The reason for such a change in programming is that it requires more effort to jog than to walk the same distance. The accelerometer deflections or counts without the methodology of the described invention would actually be less for jogging because it takes fewer strides to cover a distance traveled jogging compared to the same distance traveled walking. The firmware of the described invention can be used to assign more accelerometer deflections or counts to certain activities. The assignment of more accelerometer deflections or counts can be considered a proxy for effort. The activity module position in the magnetic field, or mobile phone selected activities when connected via Bluetooth™, reprograms the activity module and determines what motion is to be recorded during any particular activity. When weight lifting, for example, it is advantageous to eliminate most of the movement of the user's arm that might occur when walking. The activity module can be programmed not to detect the movement associated with walking around the gym, but to detect the movement associated with lifting weights. It is understood that in weight lifting, the arm motion is largely linear, whereas in walking, the vector direction of arm motion is constantly changing through an arc. There is very little acceleration of arm motion in walking that takes place in a single vector. The firmware of the described invention can be used to program the activity module to recognize these differences in arm movement.

In another embodiment, the amount of effort expended can be determined by the use of a timer in the motion sensor, e.g., accelerometer. The timer can be used to record the number of deflections per unit time. The timer can be keyed to start and stop with the beginning and conclusion of a particular exercise. The number of deflections recorded per unit time can be translated into a refinement of the calculation of the effort expenditure different than simply recording the total number of deflections performed. Without being bound by theory, it is believed that there is a limit to the velocity with which that individual can transport himself/herself through space with each deflection. The described invention assumes this to be a constant value when performing calculations and thus there is no need to measure it. By way of example, if a user is running or pedalling a bike, the revolution of the pedal and the individual stride covers roughly the same distance no matter how fast the user is traveling. The only variable is the number of revolutions of the pedal or the number of strides per unit time. Because velocity is calculated as distance/time, and because for any given individual a distance travelled per deflection for any given activity can be assigned, only time is needed to calculate the velocity. A timer in the motion sensor, e.g., accelerometer, can be activated with each separate sequence of movements to determine how much time passes while these deflections are being collected. The beginning and end of a sequence of deflections can be defined which allows the described invention to pre-specify how much time can elapse before the sequence of deflections is ended and a new sequence of deflections begins. The timer initiates with each sequence of deflections and is thus constantly cycling on and off in any given activity. As described, the engineered environment interprets this data, thereby providing meaning to the velocity calculation. Because the velocity of an object traveling through a distance is linearly related to energy expenditure, additional multipliers can be assigned to each deflection, depending upon how quickly the deflections are recorded and what type of activity is being performed. The basic energy calculation is that of moving a known mass (i.e., weight of the user) through a specified distance (i.e., stride of the user, considered a constant distance multiplied by the number of deflections to reflect the total distance travelled) and a calculated velocity (i.e., the number of deflections equating to a distance travelled per unit time as measured by the activity module's internal clock which equals distance/time or velocity). This analysis can be performed both for cardio activities and weight lifting, however velocity calculations for effort are in the opposite direction for weight lifting. For example, in weight lifting mode, the speed with which the weight moves is inversely proportional to the weight being lifted. A set of heavy weights generally will have less deflections per unit time. A multiplier can be assigned to the deflections in the weight lifting mode such that the recording of fewer repetitions per unit time will be assigned a higher multiplier per deflection.

Because the activity module of the described invention is a learning algorithm, it only needs to study the variance within the individual user of weight loss or gain, food consumed and activity type to begin to make an accurate assessment of energy expenditure. The timer counts the number of deflections per unit of time and the release time determines the beginning and end of each cycle of repetitions or the initiation and termination of a specific activity. In this way, the user's energy consumption can be characterized from the movement performed during a specific activity.

In an embodiment, the activity module includes an accelerometer. The accelerometer of the described invention can operate within an engineered magnetic environment. The accelerometer can be programmed to measure a specific type of movement. Deflections recorded by the accelerometer can be registered into a processor and recognized by firmware as being from a particular pre-specified activity by the engineered magnetic environment. The accelerometer of the described invention can be programmed to record certain types of motion by the magnetic prescribed for a certain activity. The accelerometer of the described invention can be programmed to record certain motions (i.e., deflections, counts, clicks) but to not record other motions (i.e., deflections, counts, clicks). Based on this differential recordation of motion (i.e., programmed to record certain motions but not to record other motions) by the accelerometer, differential multipliers can be assigned to different activities which reflect the different amount of energy required to perform different types of motion.

In an embodiment, the accelerometer of the described invention includes parameters of function. Such parameters include, but are not limited to, sensitivity, scale, detection time, count minimum and release time.

In an embodiment, the described invention allows a user to select the site (e.g., wrist, pocket, ankle, lanyard, etc.) where the activity module will be worn. It is generally accepted that an accelerometer will count with wide variation for the same activity (e.g., walking) if worn in different locations on the body. By allowing a user to choose the site where the activity module will be worn, the activity module can be programmed to that particular body location so that the accelerometer can count the same number of deflections for an activity (e.g., walking) performed with the activity module, for example, worn in the lanyard position, as for the same activity (e.g., walking) performed with the activity module worn, for example, on the wrist.

According to the Centers for Disease Control and Prevention, an estimated 50-70 million U.S. adults suffer from a sleep or wakefulness disorder (Institute of Medicine. Sleep Disorders and Sleep Deprivation: An Unmet Public Health Problem. Washington, D.C.: The National Academies Press; 2006). Current methods for identifying sleep disorders are costly and inconvenient. A sleep recording or polysomnogram (PSG) is performed overnight at a sleep center or sleep laboratory. Electrodes and other monitors are placed on the scalp, face, chest, limbs and finger. These devices measure brain activity, eye movement, muscle activity, heart rate and rhythm, blood pressure and oxygen levels in the lungs and blood during sleep.

In an embodiment, the described invention provides an activity monitoring mode for sleep. By way of example, a user assigns a time period in which the user is going to bed by activating a "going to bed" command on a device (e.g., mobile phone) containing a sleep algorithm of the described invention. The "going to bed" command can be transmitted to the activity module worn by the user via Bluetooth™. The processor reprograms the standard mode ("S") by changing the parameters designed to capture motion of routine daily activities to parameters designed to capture motion when lying in bed. Restfulness of the sleep period can be determined by tracking the amount of motion that occurs during the assigned time period by the motion sensor, e.g., accelerometer. The user then declares a conclusion to this sleep period by activating a "getting up" command on a device (e.g., mobile phone) containing a sleep algorithm of the described invention. The "getting up" command can be transmitted to the activity module worn by the user via Bluetooth™. The processor reprograms the standard mode ("S") by changing the parameters designed to capture motion when lying in bed to parameters designed to capture motion of routine daily activities. Because the motion associated with sleep is not associated with other forms of activity, the motion sensor, e.g., accelerometer, data can be stored in a separate counter from that used to store accelerometer data from other forms of activity. The motion sensor, e.g., accelerometer, data can be analyzed in comparison to other rest periods in order to create a portfolio of user movement during sleep time hours amortized for comparison into units of motion per unit time in "going to bed" mode. By comparing these movements, the sleep algorithm of the described invention can track and display weighted percentages of movement changes and determine how quiescent (i.e., restful) sleep was during the assigned time period.

In an embodiment, the described invention provides a method for measuring quality of sleep (e.g., restfulness). By way of example, a user assigns a time period in which the user is going to bed by activating a "going to bed" command on a device (e.g., mobile phone) containing a sleep algorithm of the described invention. The "going to bed" command can be transmitted to the activity module worn by the user via Bluetooth™. The processor reprograms the standard mode ("S") by changing the parameters designed to capture motion of routine daily activities to parameters designed to capture motion when lying in bed. Restfulness of the sleep period can be determined by tracking the amount of motion (i.e., deflections, counts, clicks, etc.) that occurs during the assigned time period by the motion sensor, e.g., accelerometer. The user then declares a conclusion to this sleep period by activating a "getting up" command on a device (e.g., mobile phone) containing a sleep algorithm of the described invention. The "getting up" command can be transmitted to the activity module worn by the user via Bluetooth™. The processor reprograms the standard mode ("S") by changing the parameters designed to capture motion when lying in bed to parameters designed to capture motion of routine daily activities. Because the motion associated with sleep is not associated with other forms of activity, the motion sensor, e.g., accelerometer, data can be stored in a separate counter from that used to store accelerometer data from other forms of activity. The motion sensor, e.g., accelerometer, data can be analyzed in comparison to other rest periods in order to create a portfolio of user movement during sleep time hours amortized for comparison into units of motion per unit time in "going to bed" mode. By comparing these movements, the sleep algorithm of the described invention can track and display weighted percentages of movement changes and determine how quiescent (i.e., restful) sleep was during the assigned time period. Without being bound by theory, greater periods of decreased motion may imply a more restful sleep.

In an embodiment, 0-400 accelerometer deflections per night can be indicative of restful sleep. In another embodiment, 50, 100, 150, 200, 250, 300, 350 and 400 accelerometer deflections per night can be indicative of restful sleep.

In an embodiment, 400-600 accelerometer deflections per night can be indicative of less restful sleep. In another embodiment, 450, 500, 550 and 600 accelerometer deflections per night can be indicative of less restful sleep.

In an embodiment, 600-1,000 accelerometer deflections per night can be indicative of a sleep disturbance. In another embodiment, 650, 700, 750, 800, 850, 900, 950 and 1,000 accelerometer deflections per night can be indicative of a sleep disturbance. In another embodiment, sleep disturbances include but are not limited to, sleep apnea.

In an embodiment, the described invention provides a method for determining an increased physiological benefit during sleep.

It is generally accepted that the glymphatic system, a brain-wide paravascular pathway for cerebrospinal fluid (CSF) and interstitial fluid (ISF) exchange, facilitates efficient clearance of solutes, waste and proteins linked to neurodegenerative diseases from the brain (Iliff J. J. et al., The Journal of Clinical Investigation, Vol. 123, No. 3, March 2013, pp. 1299-1309; Iliff J. J., Science Translational Medicine, 4, 147ra111 (2012); Yang L. et al., Journal of Translational Medicine 2013 11:107). Proteins linked to neurodegenerative disease include β-amyloid (Aβ), α-synuclein and tau which are present in the interstitial space surrounding cells of the brain (Id.). Xie et al. (Xie, L. et al., Science 342, 373 (2013)) have shown that natural sleep or anesthesia in mice is associated with a 60% increase in the interstitial space, resulting in an increase in convective exchange of CSF and ISF. In turn, these connective fluxes of the ISF increased the rate of clearance of proteins linked to neurodegenerative disease (e.g., Aβ) during sleep, leading Xie et al. to conclude that the restorative function of sleep may be a consequence of the enhanced removal of potentially neurotoxic waste products that accumulate in the awake central nervous system (Xie, L. et al., Science 342, 373 (2013)).

In an embodiment, the described invention can process sleep deflections into the health quotient. Without being bound by theory, a decrease in sleep deflections may be indicative of improved fitness while an increase in sleep deflections may be indicative of a sleep disturbance.

In an embodiment, the described invention can set goals for the types and amounts of activity to be performed. For example, a user accesses his/her profile page and selects "Arc label" or "fitness program". Once selected, the program can analyze what percentage of activity should be resistance training, cardio training and routine activity for the profile selected. This percentage goal for each type of activity is assigned to training circles. Therefore, the user's goal is to fill the training circle in order to meet the goals as determined on the user's profile page. These training circles are a percentage of activity (i.e., not an absolute number). As the user varies activity (e.g., by performing more exercise) there will be more deflections in the daily activity circle which represents the total number of activity counts for the day. For example, more of any given type of exercise will need to take place to fill the muscle or cardio training circle completely. The percentage will remain constant, but the number of activity counts will go up and down depending on the users overall pattern of activity. The program examines the user's history and number of deflections recorded during the day and then divides those deflections into various forms of activity (e.g., aerobic, routine, etc.) in order to meet the training goals selected on the user's profile page. A different profile will assign different percentages to the training circles. The total number of deflections required to reach the user's selected fitness and weight goals are determined by the program analytics based on changes in weight and muscle mass. The activity count goals are determined after calculation of the patients basic internal requirement needs (BIRN) which is the activity module's equivalent of metabolism. The program accounts for age differences, gender differences, and beginning fitness levels not by assigning values based upon these characteristics, but by individually studying the user's BIRN, exercise and food consumption behavior. In addition, the program has the ability to instantaneously review the percentage of activity that is aerobic versus weight or resistance training. In another embodiment, the percentages in the training circles can be customized. For example, the percentages in the training circles can be changed and recalculated by an athletic trainer working with a user.

Figure 15A:
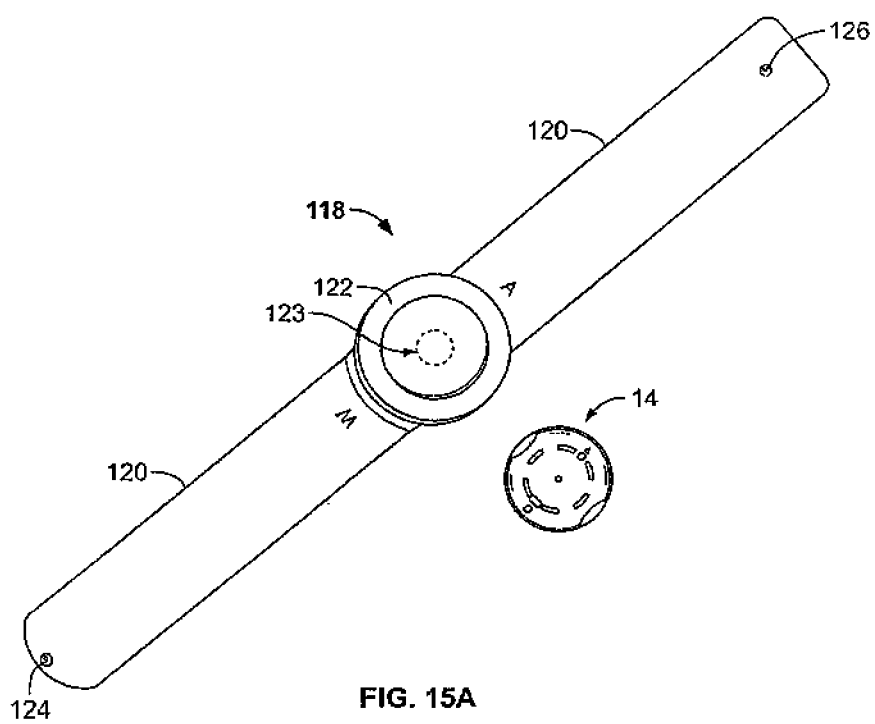
FIG. 15A is a plane view of a band which has a strap with a receptacle position thereon, the band can be shown positioned adjacent to the activity module.

FIG. 15A illustrates a band 118 that is depicted positioned adjacent to the activity module 14. In an embodiment, the band 118 has a strap 120 with a pouch or receptacle 122 that can be centrally positioned thereon. A magnet 123 can be embedded in the center of the receptacle 122, for magnetically retaining the activity module 14 in the receptacle 122. The strap 120 can have connectors 124, 126 that facilitate the releasable fastening of the strap 120 around the wrist or ankle of the user. More particularly, a pin 124 may fasten on one of a plurality of circular-shaped pin-catches 126. Alternatively, the connectors 124, 126 may be hook-and-loop fasteners such as Velcro®. The band 118 can be fabricated from an elastomeric material, such as rubber. Also, the band 118 may be formed as a bracelet, e.g., with a series of metal links that can be fastened about the wrist or ankle of the user.

In an embodiment, the strap 120 can be imprinted with an indicia A that can be located proximate to one side of the receptacle 122. The indicia A can represent a user aerobic exercise mode. The strap 120 can be also imprinted with an indicia W that can be located proximate to the opposite side of the receptacle 122. The indicia W can represent a user weight training exercise mode. Imbedded in the strap 120, located proximate to the indicia A, can be a permanent magnet (not shown) which can have one of its magnetic poles directed toward the receptacle 122. Imbedded in the strap 120, located proximate to the indicia W can be a permanent magnet (not shown) which has an opposite magnetic pole directed toward the receptacle 122. Alternately, the activity module 14 may be worn on a garment clip, in a pocket, on a lanyard, etc.

Figure 15B:
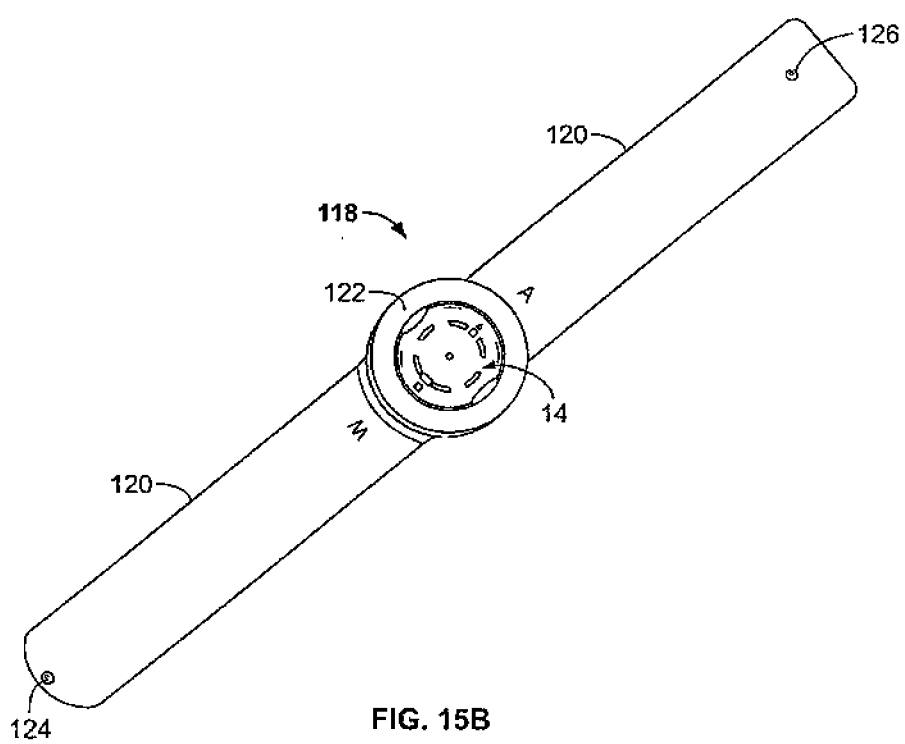
FIG. 15B is a plane view of the band shown in FIG. 15A in which the activity module can be shown installed in the receptacle.

Referring to FIG. 15B, the activity module 14 is shown installed in the receptacle 122. The receptacle 122 can be sized and shaped for removably receiving the activity module 14, and due to the supple nature of the elastomeric material construction of the receptacle 122, the activity module 14 may be installed in the receptacle 122 by way of the user positioning one edge of the activity module 14 in the opening of the receptacle 122 and pressing the opposite edge until it can be fully installed in the receptacle 122. The activity module 14 may be removed from the receptacle 122 by pressing the exterior of the bottom of the receptacle 122, towards the bottom 100 of the activity module 14, until the activity module 14 is pressed out of the receptacle 122. This may serve to hold the activity module 14 within the receptacle 122 even without the magnet 123. In an embodiment, due to the supple nature of the receptacle, the activity unit 14 may remain installed in the receptacle 122 when the user simultaneously presses the buttons 104.

Figure 16:
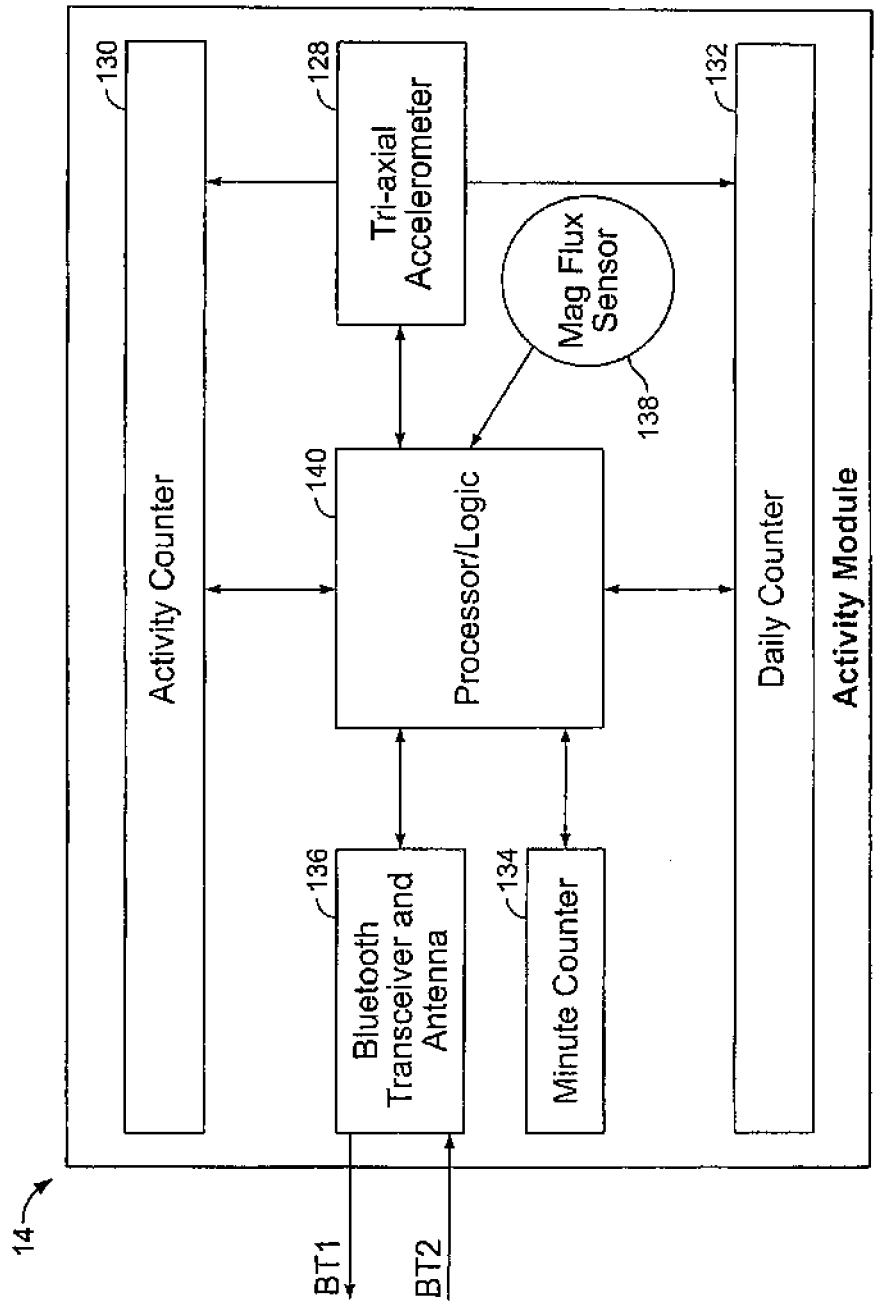
FIG. 16 is a schematic drawing of the activity module.

Referring to FIG. 16, the activity module 14 can include at least one multi-axis accelerometer 128, or alternatively two or three single axis accelerometers, an activity units counter 130, a daily counter 132, a time counter 134, e.g., a minutes counter 134, a Bluetooth™ transceiver 136, a magnetic flux field sensor 138, and a processor/logic (computing device) unit 140. The multi-axis accelerometer 128 can be a tri-axis accelerometer unit 128 that measures, e.g., the deflections of a suspended mass (not illustrated) in three orthogonal directions as a result of movement of the activity module 14. For example, any change in the movement of activity module 14 that is caused by changes in the movement of the user can cause an acceleration of the suspended mass in the X, Y and/or Z axis of the accelerometer 128, resulting in a deflection or "click" of the accelerometer 128 in X, Y or Z axis.

Each such deflection can be used to produce one click, which can be equated to an activity unit or a portion of an activity unit, by the processor/logic unit 140 of the activity module 14, or alternatively, in some modes, two "clicks", one forward and one back, can be equated to an activity unit or a portion of an activity unit, in a manner discussed below. The activity units can be recorded and accumulated in the activity counter 130 and/or the daily counter 132, and can be transmitted (i.e., downloaded) to the application 12, e.g., by the Bluetooth™ transceiver 136, periodically and/or during the synchronization process that is described above. The activity units can be processed by the power equation 2, as described above.

The activity counter 130 can keep a running total of the activity units, e.g., until it receives a command from the digital device D. This data can be maintained for additional analysis, e.g., in the event that the user fails to download activity from the daily counter 132 which, e.g., may be configured to reset to zero every 24 hours, or to separately store daily accumulations for several days. The activity counter 130 can also start to count until it reaches the maximum value allowed by the hardware. At that time, it can be reset to zero. It can be, therefore, possible that the activity counter 130 may keep counting on multiple days. It will be understood that the user may command the application 12 to reset the activity counter 130 to zero by using a "clear activity" command (not shown) during synchronization between the digital device D and the activity module 14.

The daily counter 132 can maintain a running total of activity units for a 24 hours period(s). With each synchronization the application 12 can then calculate the difference between the last and current activity count for a given 24 hour period in order to update calculations and page displays. For example, the application 12 can update the activity circle 38 count and the expected number of activity units on the activity module 14. Therefore, the daily counter 132 can start to count activity units until the end of the day (i.e., when the minute timer 134 reaches a value of 1440 minutes) at which time it can be reset to zero. It will be understood that the application 12 can remember the daily counter's 132 value at the last synchronization so that the application can calculate the difference in the recorded values between synchronizations.

Since it can be possible that the activity unit 14 might not be in sync with the current time (at the minute level) during synchronization, the digital device D can set the minute timer 134 to the current time based on the digital device's D clock. This can assure that the application 12 and the activity module 14 both conclude a 24 hour (i.e., 1440 minute) period at the same time and can allow the user to travel to different time zones and maintain accurate application 12 functionality. At the end of the daily 1440 minute countdown, the activity module 14 can reset and begin a new count which can correspond to the next day.

The user can adjust the activity module 14 to measure an aerobic mode of exercise, or an anaerobic, e.g., weight training, mode of exercise. This can be accomplished by orienting the activity module 14 in the receptacle 122 of the band 118 so that when the arrow-shaped pointer 106 is pointing to the indicia A, the orientation of the magnetic flux field exerted by the strap 120 can be detected by the magnetic flux field sensor 138 and can be communicated to the processor/logic unit 140. The processor/logic unit 140 can then interpret the activity units as being generated by the user who is performing aerobic exercise. When the user orients the activity module 14 in the receptacle 122 so that the arrow-shaped pointer 106 points to the indicia W, the processor/logic unit 140 can interpret the output of the magnetic flux detector 138 as indicating the user activity units are being generated by the user who is performing some form of anaerobic exercise, e.g., weight lifting. When so oriented, the processor/logic unit 86 of the activity module 14 can add a multiplier to the calculations of the activity count. (The multiplier number may be changed via an input to the algorithm through the Bluetooth™ interface). The multiplier can alter the activity counts that can be transmitted to the application 12, so that each individual deflection (or back and forth deflection) may be transmitted to the application 12 as a single count, e.g., in a normal anaerobic training mode, or "standard activity" mode or, for example, multiplied by 2 for intense anaerobic training, or multiplied by 3 for aerobic training, or by 4 for intense aerobic training. It will be understood that other multipliers and/or means of accounting for a single step or single exercise repetition, or the like, may be possible When the user is about to begin high intensity or "turbo" exercise activities, he/she can briefly depress the buttons 104. This can, e.g., place the activity module 14 temporarily in a high intensity or turbo physical exercise monitoring mode in which the activity units that are generated by the activity module 14 can be multiplied by an additional factor so that each deflection has a greater impact on the activity circle 116 than when in ("normal") weight training or aerobic training without the turbo function engaged. An indicator light 119 may be illuminated when the activity module 14 can be placed in the turbo exercise monitoring mode. At the end of the turbo exercise activities the user can again briefly depress the buttons 104 to exit the high intensity exercise mode, or alternately, the activity module 14 can automatically turn off the high intensity exercise monitoring mode when it senses a sustained decrease in the frequency of activity units.

As described above, the activity module 14 can be adapted to measure and record activity units in the following five physical activity modes: i) aerobic, ii) intense or turbo aerobic, iii) weight or muscle training, iv) intense or turbo weight training, and v) standard activity mode. The processor/logic unit 140 can, e.g., interpret one click of the accelerometer in each of the five physical activity modes as follows: i) in the aerobic exercise mode, one click can be equal to (A×1 repetition) activity unit, where A can be a predetermined constant coefficient, ii) in the turbo aerobic mode, one click can be equal to (A+×1 repetition) activity unit, where A+ can be a predetermined coefficient, iii) in the weight training mode, one click can be equal to (W×1 repetition) activity unit, where W can be a predetermined coefficient, iv) in the turbo weight training mode, one click can be equal to (W+×1 repetition) activity unit, where W+ can be a predetermined coefficient, and v) in the standard activity mode, one click can be equal to (R×1 repetition or alternatively time period) activity unit, where R can be a predetermined constant coefficient. These values can be altered, e.g., via the Bluetooth™ algorithm by the user, athletic coach or health professional to create unique exercise programs beyond those provide in the system 10.

It should be appreciated that the disclosed subject matter provides numerous advantages. For instance, in the event that the application 12 is implemented on a digital device D such as a smart phone, the system 10 can be therefore normally close at hand to the user throughout the day. This can encourage the user to accurately input food consumption close to the time it occurs. The method of utilizing food icons for inputting the type and portion size for food consumption, without the need for looking up and computing calories, can further encourage the user to more accurately and conveniently input food consumption and to do so close to the time it is or will be consumed. Likewise, wearing the activity module 14 can further contribute to the user conveniently and autonomously inputting the activity units in the systems 10. The system 10 features concise, powerful and completing graphical indicators on the health and fitness of the user, such as i) the fitness arc 34 which can provide, e.g., an energy balance that can be an indicator of the effectiveness of the user's daily weight and fitness management, ii) the health quotient 42 which can provide, e.g., an indicator of the health of the user for a particular extended time period, iii) the fluid an salt circles 31A and 31B, iv) the activity circle 38, the v) the Vit circle 82, and the like and vi) favorite food indicator(s) 56. Further, the system 10 can compensate(s) for user inaccuracies in food portion size estimates by assessing the user's energy balance including his/her intrinsic metabolism and adjusting the food estimates accordingly or simply automatically increasing or decreasing the food intake units, e.g., daily. The system also has the flexibly of operating on a combined mode, or an estimated mode in which the user does not utilize the activity module 14, and instead estimates his/her activity units.

For example, the estimated algorithm mode of the application 12 can begin with an assigned and fixed number of activity units. The assigned amount can be derived from the learning algorithm that runs when the activity module 14 is actually used to record all activity, or in cases where the activity module 14 has not been used, a value can be assigned based upon the users selected profile.

Figure 17:
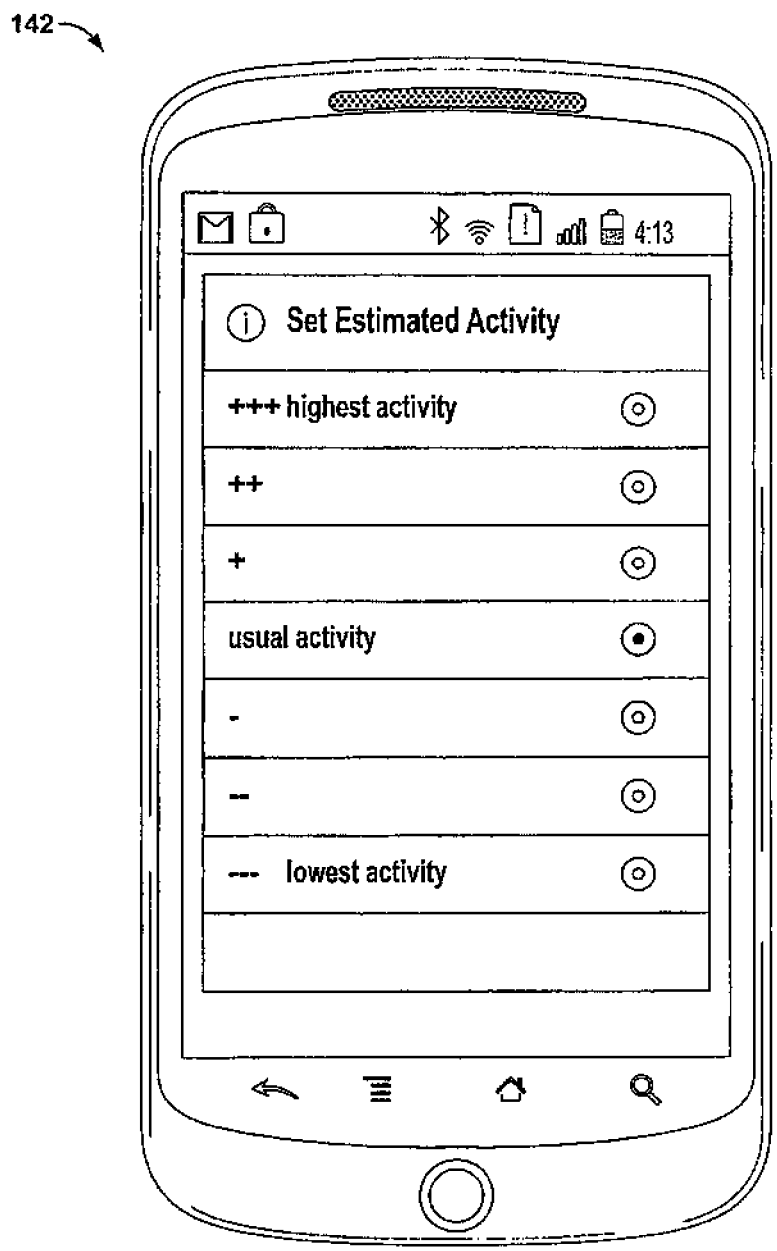
FIG. 17 is a user activity estimation input screen.

Referring to FIG. 17, the user can make a selection from an estimated activity page 142 that describes his/her activity. The entry of the estimated amount of activity can be input as often as the user chooses. If no entries are made, the algorithm can assume that the activity for that day was a usual or forecasted/assigned amount, or the like. Each user estimated activity update can apply to the time period from the last entry/estimation. Thus if 100 activity units were expected at 8 AM and the user selects "usual," then 100 units can be added to activity circle 116. Selection of a plus or minus option can alter the activity units forecasted/assigned for that period of time by plus or minus 10%, 20% or 30%. For example, the activity units entered might be 100, 120 or 80 etc.

The next time the user enters the estimated activity, the application 12 can have expected a certain number of activity units to have been performed since the last entry. Expected activity units can be the number registered to the activity circle if the user selects the "usual" option from the estimated activity page 142. The number of expected units can be determined by the amount of time that has past, since the user last registered activity by a selection from the estimated activity page 142. For example the algorithm might have expected the user to have registered 1000 activity units since the time of last entry, and if "+++" is selected, the algorithm can place 1300 units into the activity circle 116. If at the time of the next entry 2000 units would have been expected (i.e., 2,000 units would have occurred in the time frame since the last entry) and "−−" had been selected, the algorithm can enter 1,600 units into the activity circle 116.

If the estimated activity units are used to describe the majority of daily activity, but the user wishes to use the activity module 14 to quantify exercise, then the application 12 can process those activity units as a percentage of those expected during the time frame during which activity module 14 was in use and apply a 10%, 20%, or 30% increment to the activity count total. For example, if in the time frame between the last entry in the application 12 estimation-algorithm's algorithm the algorithm would expect 1000 units, but the user, instead of making a selection from the estimated activity page chooses to utilize the activity module 14 for entry of actual activity units, the algorithm can perform as follows:

for any number of activity units that the activity module 14 provides which are less than expected plus 20% (1200 activity units in the current example) the application can place the expected plus 10% units into the activity circle 116, (1100 activity units in the current example); between an expected plus 20% and expected plus 30% the application 12 can add expected plus 20% to activity circle 116, (1200 units in the current example); and for any number of activity units above 30% of expected, then the expected plus 30% can be added to activity circle 116, (1300 units in the current example). The maximum allowed activity count can be an expected plus 30%, regardless of the actual number of activity counts (e.g., 1400 activity units would be entered as 1300 units to activity circle 116).

It should be noted that the disclosed subject matter can have numerous modifications and variations. For instance, users sponsored by a business or organization may receive downloads to the system 10. The business or organization may generate a rewards algorithm for the sponsored users by providing benefits such as financial rewards, music, cell phone minutes, video game access, etc.

In some embodiments, the device D may receive signals not only from an activity module 14, but also from other devices. For example, a body weight scale may be adapted to wirelessly transmit weight values to the digital device D, thereby automatically recording the user's actual weight in the system 10. In another embodiment, the body weight scale can be used to confirm calculations relating to the user's weight. For example, the user's actual weight is transmitted to the device D via Bluetooth™. The transmitted actual weight is used to validate calculations relating to the user's weight. The user does not see an actual numeric value on the device or on the body weight scale.

In an embodiment of the method in step (e), the change in weight is displayable either as a numeric weight or via a colored dot display system, the colored dot display system comprising: a red dot representing weight gain other than muscle; a green dot representing muscle growth or weight loss; and a yellow dot representing no change in fat/muscle ratios.

It is generally accepted that weight is not a perfect surrogate for health or fitness. Weight can be altered by total body fluid, body waste accumulation or loss, as well as muscle mass gains and losses. It is understood that these components do not equate to or have the same implications as to health status as does fat or adipose tissue changes. In addition, psychological management benefits are associated with a weightless program. For example, some individuals have a phobia about measured weight and do not wish or cannot step on a scale. The inability to measure weight can be an obstacle in collecting data about an individual's health and the appropriateness of food consumption.

According to the described invention, multiple algorithms can be used to assess whether weight is gained from fat, water or muscle. The algorithms can review and assess types and amounts of food consumed, amount of liquids and salt consumed, as well as exercised performed and the rate of change in weight. By way of example, if a user consumes only ⅔ of his/her usual food allowance and performed 20% more exercise, yet the next day gained ½ pound, the software of the described invention can study these relationships and assign a value to the user's health quotient which reflects a true meaning of the measured weight. For example, foods consumed may have had a very high salt content which added to water retention thus increasing weight. The software of the described invention can determine whether change in weight is meaningful as a health determinant (i.e., from fat, water or muscle mass) and thus assign a color to represent whether a desired, neutral or undesired changed in weight has occurred.

For example, a yellow circle can be assigned to indicate no meaningful fitness or health change to a user's weight. A red circle, for example, can be assigned to indicate that there has been weight gain which falls outside of the users stated health goals. A green circle, for example, can indicate that there has been weight loss in accordance with the user's health goals. Thus, the weightless fitness management program of the described invention provides the use of a color in place of a numerical weight value.

Some users wish to gain weight for health and fitness purposes, but not all weight gain is healthy. The weightless fitness management program of the described invention can perform an assessment of food amount and type, as well as the amount and type of activity performed (e.g., anaerobic weight lifting versus aerobic jogging). This assessment can determine if changes in weight are the result of proper eating and training effort. Once the determination is made, a color as described above is displayed in place of numerical weight. The weightless fitness management program of the described invention can distinguish whether weight gain is muscle or fat based on the types and amount of exercise performed.

In an embodiment, the data used by the weightless fitness management program to determine whether weight gain is muscle or fat can be integrated into the multiple parameters that form the health quotient of the described invention and thus displayed as a single point on a scale ranging from fit to healthy to unhealthy to at risk.

Similarly, when test results items such as blood pressure are recorded, such information may be automatically transmitted to the digital device D. In other embodiments, the digital device D may interface with an electronic patient chart, allowing the user to upload information from the user medical chart directly to the system 10. In an embodiment, the system 10 may provide real time advice with respect to the user's choice of foods and activity to improve the prospect of reaching specific health and fitness goals, and the system 10 may consider factors such as whether the user is a long distance runner, whether the user is pregnant, elderly, and/or whether the user has health related diseases such as hypertension, diabetes, obesity, or anorexia. Having disclosed the apparatus and functions of the system 10, examples of some of the system 10 operational facilities are provided below.

Figure 18:
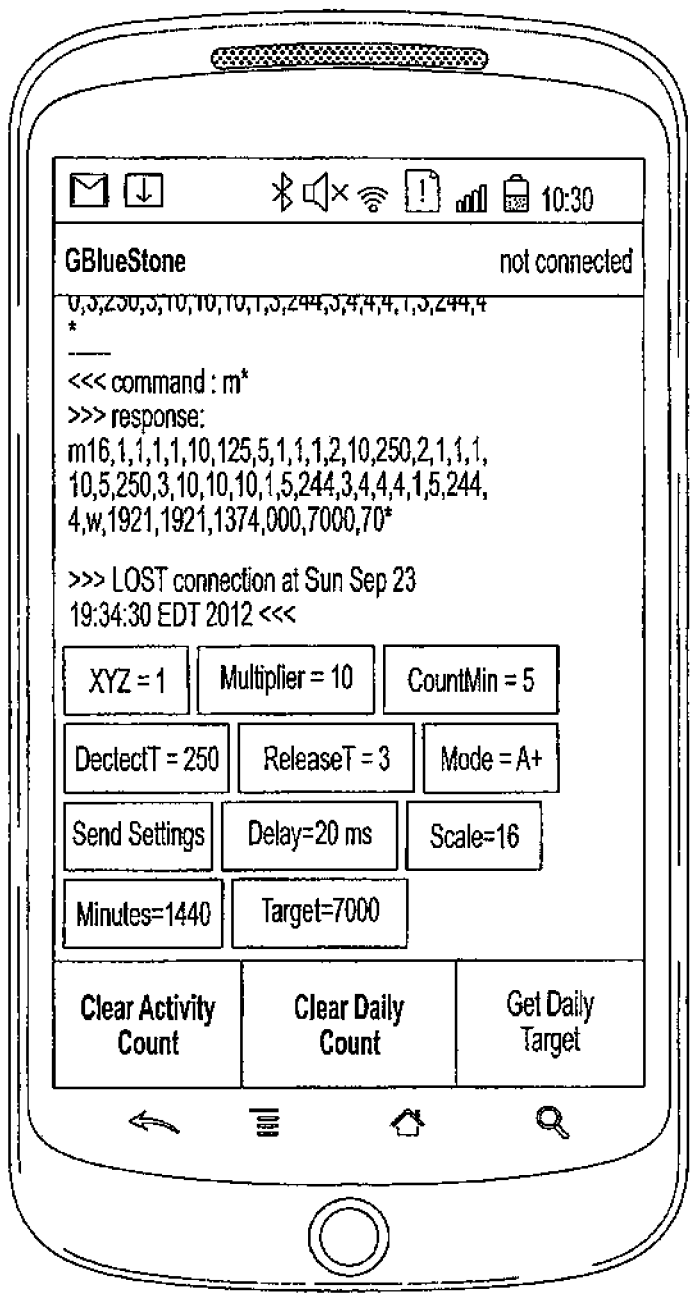
FIG. 18 is a screen showing a command string for controlling the performance of the activity module.
Figure 19A:
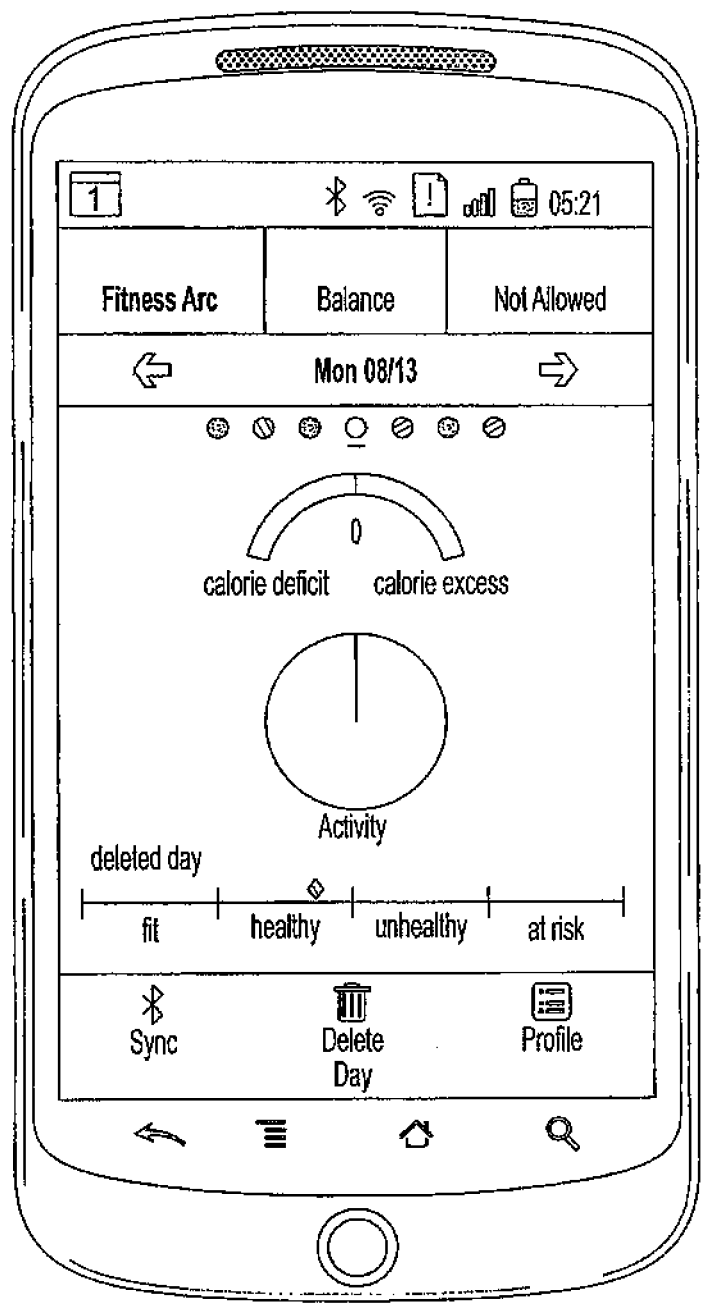
FIG. 19A is a screen showing a "deleted day" message.
Figure 19B:
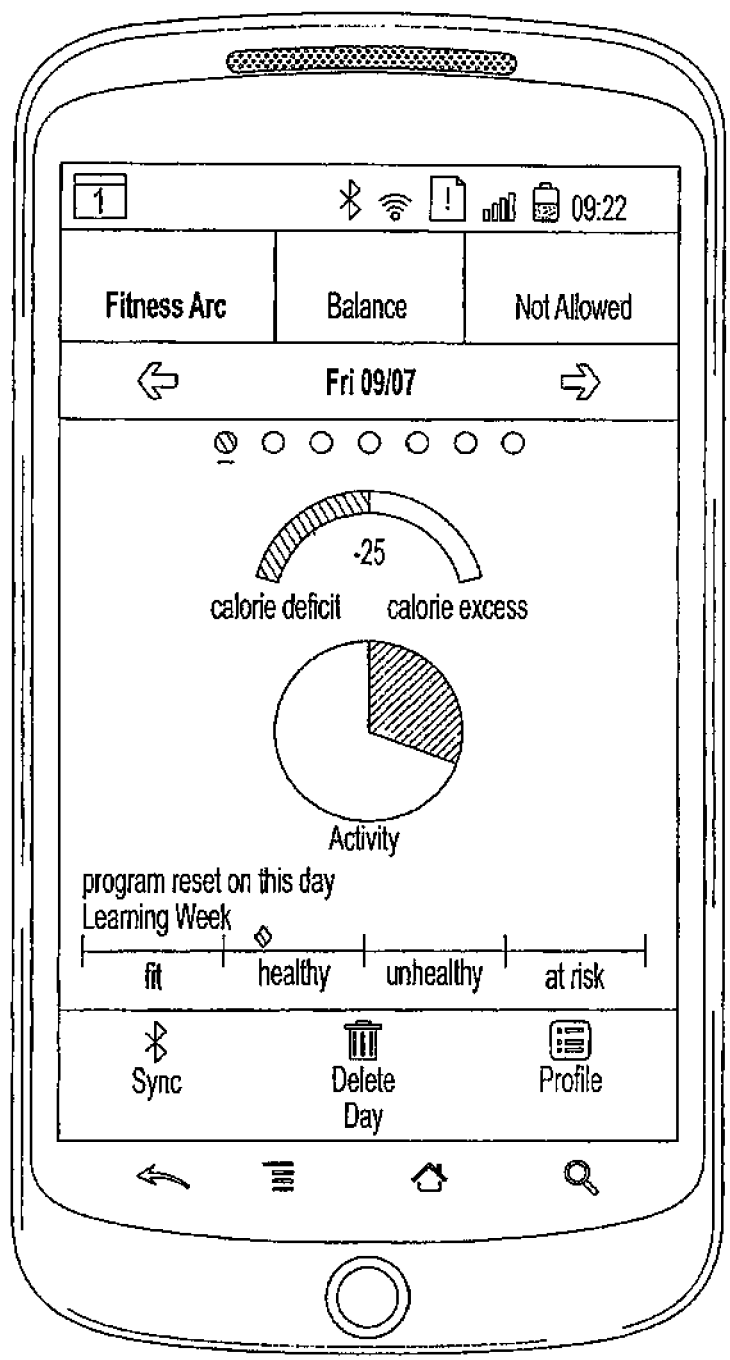
FIG. 19B is a screen showing an "algorithm reset on this day" message.
Figure 20:
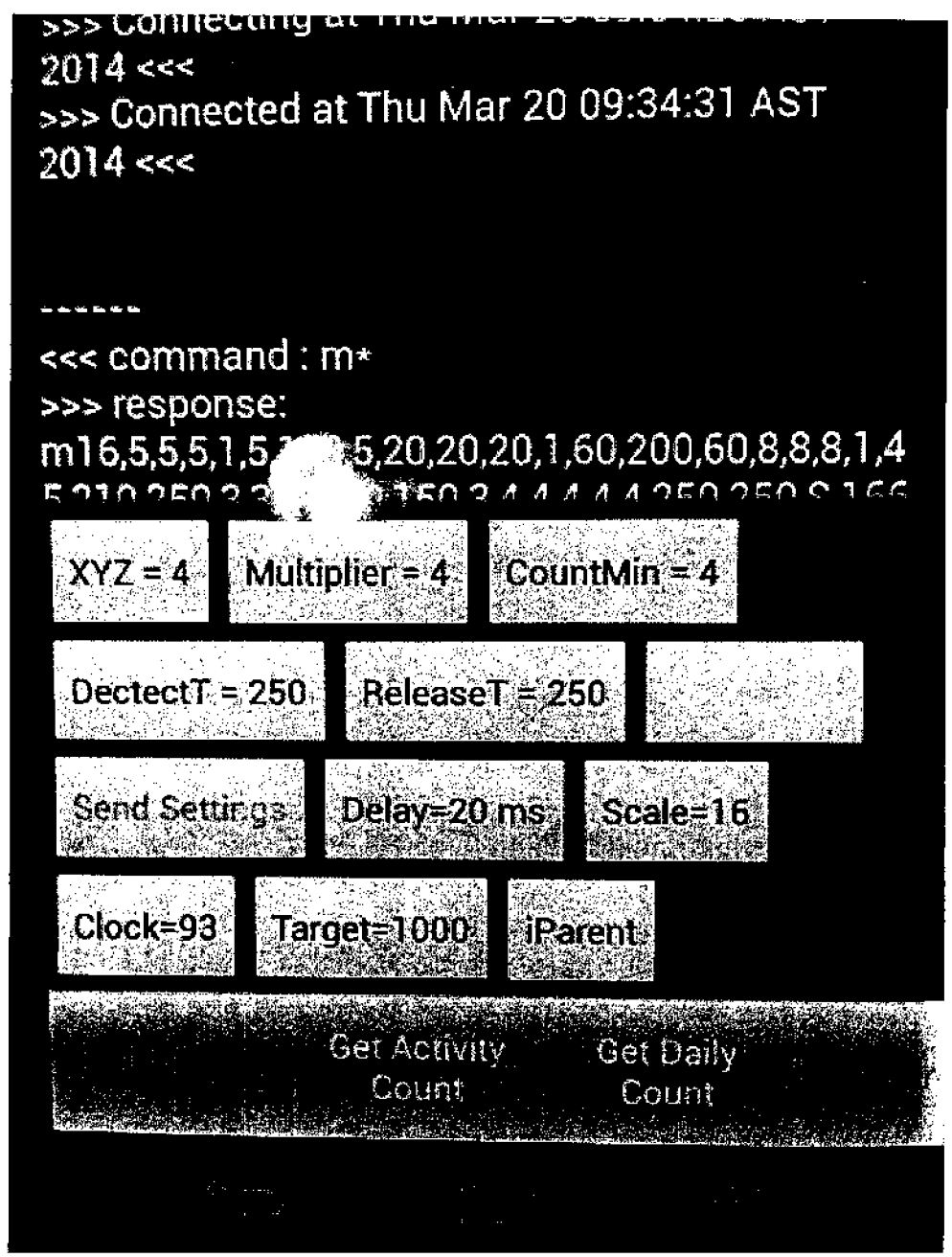
FIG. 20 is a screen showing firmware commands.
Figure 21:
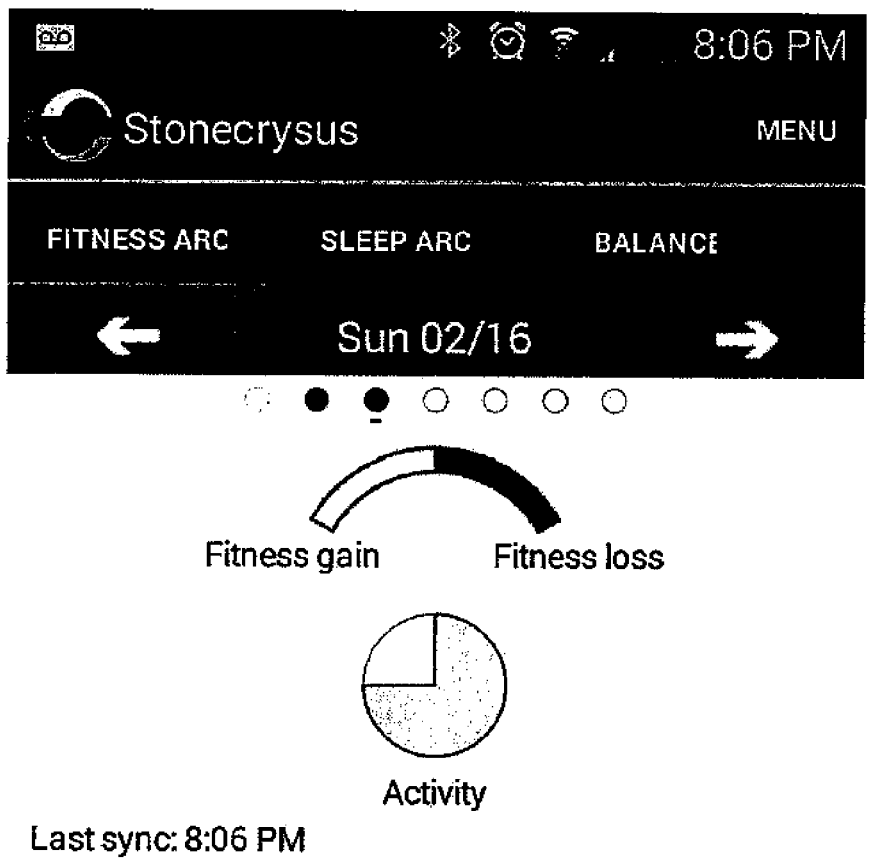
FIG. 21 is a fitness arc information screen showing a fitness loss.
Figure 21:
Figure 22:
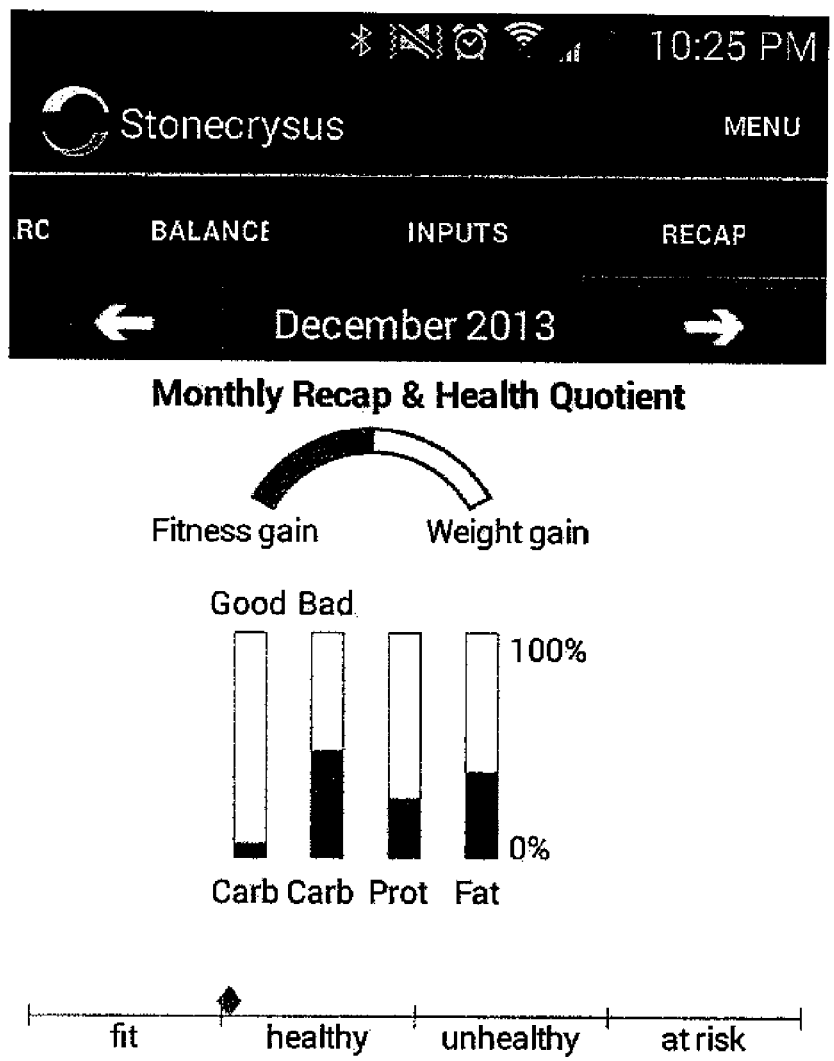
FIG. 22 is a recap information screen showing a fitness arc (top), percentages of good carbs, bad carbs, protein (Prot) and Fat consumed (middle) and health quotient (bottom)
Figure 23:
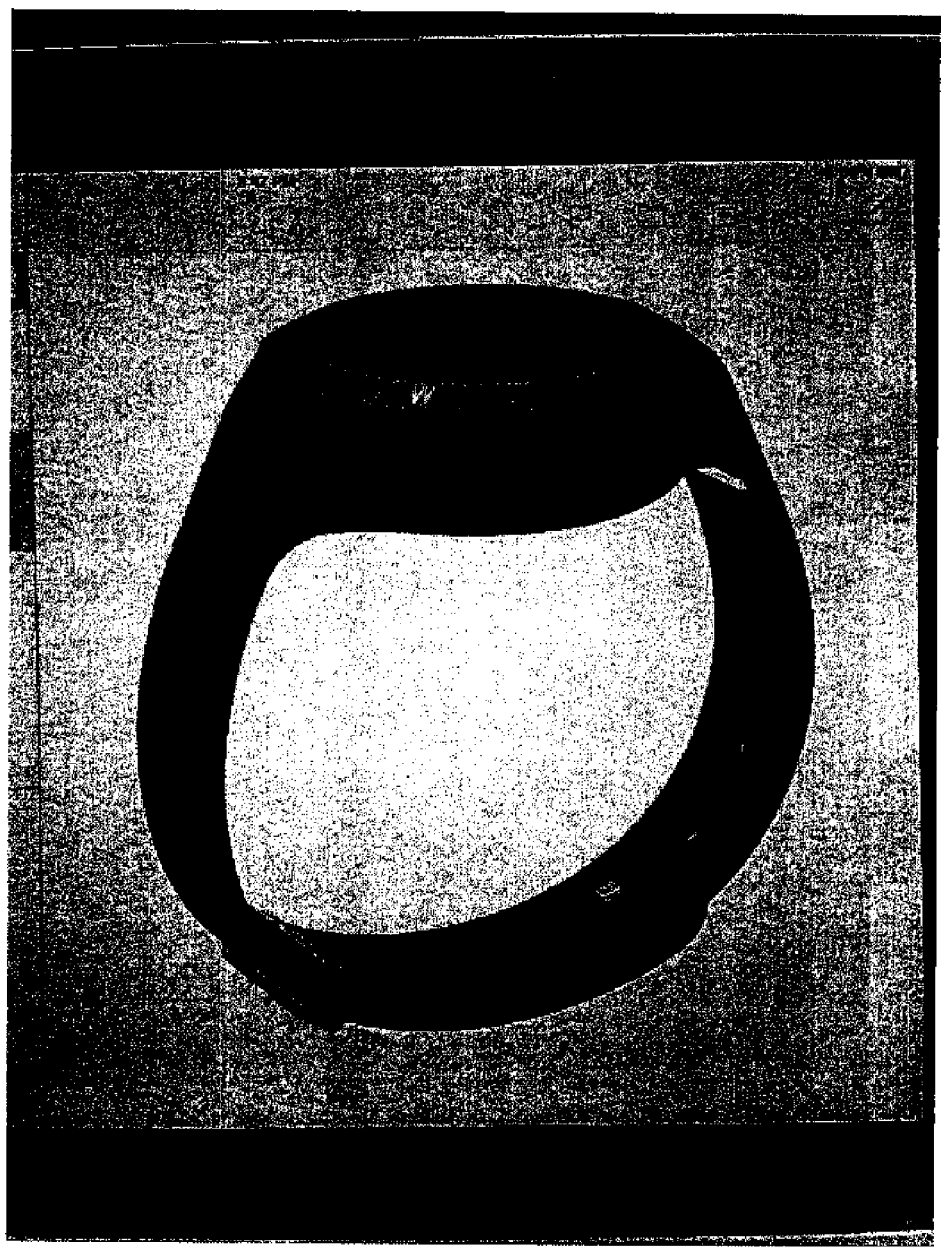
FIG. 23 is a picture of a side view of a band for the activity module which has a strap with a receptacle.

Referring to FIG. 18, the user may reprogram the activity module 14 (e.g., the activity monitoring modes described herein), e.g., via the application 10 and the Bluetooth™ transceiver of the digital device D. Also FIGS. 19A and 19B illustrate a facility to remove a day's input, which may be required should the user believe that data for a particular day are not correct or was not entered accurately.

The following is a disclosure by way of example of a computing device which may be used with the presently disclosed subject matter. The description of the various components of a computing device is not intended to represent any particular architecture or manner of interconnecting the components. Other systems that have fewer or more components may also be used with the disclosed subject matter. A communication device may constitute a form of a computing device and may at least emulate a computing device. The computing device may include an inter-connect (e.g., bus and system core logic), which can interconnect such components of a computing device to a data processing device, such as a processor(s) or microprocessor(s), or other form of partly or completely programmable or pre-programmed device, e.g., hard wired and/or application specific integrated circuit ("ASIC") customized logic circuitry, such as a controller or microcontroller, a digital signal processor, or any other form of device that can fetch instructions, operate on pre-loaded/pre-programmed instructions, and/or follow instructions found in hard-wired or customized circuitry, to carry out logic operations that, together, perform steps of and whole processes and functionalities as described in the present disclosure.

In this description, various functions, functionalities and/or operations may be described as being performed by or caused by software program code to simplify description. However, those skilled in the art will recognize what is meant by such expressions is that the functions resulting from execution of the program code/instructions are performed by a computing device as described above, e.g., including a processor, such as a microprocessor, microcontroller, logic circuit or the like. Alternatively, or in combination, the functions and operations can be implemented using special purpose circuitry, with or without software instructions, such as using Application-Specific Integrated Circuit (ASIC) or Field-Programmable Gate Array (FPGA), which may be programmable, partly programmable or hard wired. The application specific integrated circuit ("ASIC") logic may be such as gate arrays or standard cells, or the like, implementing customized logic by metalization(s) interconnects of the base gate array ASIC architecture or selecting and providing metalization(s) interconnects between standard cell functional blocks included in a manufacturer's library of functional blocks, etc. Embodiments can thus be implemented using hardwired circuitry without program software code/instructions, or in combination with circuitry using programmed software code/instructions.

Thus, the techniques are limited neither to any specific combination of hardware circuitry and software, nor to any particular tangible source for the instructions executed by the data processor(s) within the computing device. While some embodiments can be implemented in fully functioning computers and computer systems, various embodiments are capable of being distributed as a computing device including, e.g., a variety of forms and capable of being applied regardless of the particular type of machine or tangible computer-readable media used to actually effect the performance of the functions and operations and/or the distribution of the performance of the functions, functionalities and/or operations.

The inter-connect may connect the data processing device to define logic circuitry including memory. The interconnect may be internal to the data processing device, such as coupling a microprocessor to on-board cache memory, or external (to the microprocessor) memory such as main memory, or a disk drive, or external to the computing device, such as a remote memory, a disc farm or other mass storage device(s), etc. Commercially available microprocessors, one or more of which could be a computing device or part of a computing device, include a PA-RISC series microprocessor from Hewlett-Packard Company, an 80×86 or Pentium series microprocessor from Intel Corporation, a PowerPC microprocessor from IBM, a Sparc microprocessor from Sun Microsystems, Inc, or a 68xxx series microprocessor from Motorola Corporation as examples.

The inter-connect in addition to interconnecting such as microprocessor(s) and memory may also interconnect such elements to a display controller and display device, and/or to other peripheral devices such as input/output (I/O) devices, e.g., through an input/output controller(s). Typical I/O devices can include a mouse, a keyboard(s), a modem(s), a network interface(s), printers, scanners, video cameras and other devices which are well known in the art. The inter-connect may include one or more buses connected to one another through various bridges, controllers and/or adapters. In one embodiment the I/O controller may include a USB (Universal Serial Bus) adapter for controlling USB peripherals, and/or an IEEE-1394 bus adapter for controlling IEEE-1394 peripherals.

The memory may include any tangible computer-readable media, which may include but are not limited to recordable and non-recordable type media such as volatile and non-volatile memory devices, such as volatile RAM (Random Access Memory), typically implemented as dynamic RAM (DRAM) which requires power continually in order to refresh or maintain the data in the memory, and non-volatile ROM (Read Only Memory), and other types of non-volatile memory, such as a hard drive, flash memory, detachable memory stick, etc. Non-volatile memory typically may include a magnetic hard drive, a magnetic optical drive, or an optical drive (e.g., a DVD ROM, a CD ROM, a DVD or a CD), or other type of memory system which maintains data even after power is removed from the system.

A server could be made up of one or more computing devices. Servers can be utilized, e.g., in a network to host a network database, compute necessary variables and information from information in the database(s), store and recover information from the database(s), track information and variables, provide interfaces for uploading and downloading information and variables, and/or sort or otherwise manipulate information and data from the database(s). In one embodiment a server can be used in conjunction with other computing devices positioned locally or remotely to perform certain calculations and other functions as may be mentioned in the present application.

At least some aspects of the disclosed subject matter can be embodied, at least in part, utilizing programmed software code/instructions. That is, the functions, functionalities and/or operations techniques may be carried out in a computing device or other data processing system in response to its processor, such as a microprocessor, executing sequences of instructions contained in a memory, such as ROM, volatile RAM, non-volatile memory, cache or a remote storage device. In general, the routines executed to implement the embodiments of the disclosed subject matter may be implemented as part of an operating system or a specific application, component, program, object, module or sequence of instructions usually referred to as "computer programs," or "software." The computer programs typically comprise instructions stored at various times in various tangible memory and storage devices in a computing device, such as in cache memory, main memory, internal or external disk drives, and other remote storage devices, such as a disc farm, and when read and executed by a processor(s) in the computing device, cause the computing device to perform a method(s), e.g., process and operation steps to execute an element(s) as part of some aspect(s) of the method(s) of the disclosed subject matter.

A tangible machine readable medium can be used to store software and data that, when executed by a computing device, causes the computing device to perform a method(s) as may be recited in one or more accompanying claims defining the disclosed subject matter. The tangible machine readable medium may include storage of the executable software program code/instructions and data in various tangible locations, including for example ROM, volatile RAM, non-volatile memory and/or cache. Portions of this program software code/instructions and/or data may be stored in any one of these storage devices. Further, the program software code/instructions can be obtained from remote storage, including, e.g., through centralized servers or peer to peer networks and the like. Different portions of the software program code/instructions and data can be obtained at different times and in different communication sessions or in a same communication session.

The software program code/instructions and data can be obtained in their entirety prior to the execution of a respective software application by the computing device. Alternatively, portions of the software program code/instructions and data can be obtained dynamically, e.g., just in time, when needed for execution. Alternatively, some combination of these ways of obtaining the software program code/instructions and data may occur, e.g., for different applications, components, programs, objects, modules, routines or other sequences of instructions or organization of sequences of instructions, by way of example. Thus, it is not required that the data and instructions be on a single machine readable medium in entirety at any particular instant of time.

In general, a tangible machine readable medium includes any tangible mechanism that provides (i.e., stores) information in a form accessible by a machine (i.e., a computing device), which may be included, e.g., in a communication device, a network device, a personal digital assistant, a mobile communication device, whether or not able to download and run applications from the communication network, such as the Internet, e.g., an I-Phone®, Blackberry®, Droid™ or the like, a manufacturing tool, or any other device including a computing device, comprising one or more data processors, etc.

In one embodiment, a user terminal can be a computing device, such as in the form of or included within a PDA, a cellular phone, a notebook computer, a personal desktop computer, etc. Alternatively, the traditional communication client(s) may be used in some embodiments of the disclosed subject matter.

While some embodiments of the disclosed subject matter have been described in the context of fully functioning computing devices and computing systems, those skilled in the art will appreciate that various embodiments of the disclosed subject matter are capable of being distributed, e.g., as a program product in a variety of forms and are capable of being applied regardless of the particular type of computing device machine or computer-readable media used to actually effect the distribution.

The disclosed subject matter may be described with reference to block diagrams and operational illustrations of methods and devices to provide a system and methods according to the disclosed subject matter. It will be understood that each block of a block diagram or other operational illustration (herein collectively, "block diagram"), and combination of blocks in a block diagram, can be implemented by means of analog or digital hardware and computer program instructions. These computing device software program code/instructions can be provided to the computing device such that the instructions, when executed by the computing device, e.g., on a processor within the computing device or other data processing apparatus, the program software code/instructions cause the computing device to perform functions, functionalities and operations of a method(s) according to the disclosed subject matter, as recited in the accompanying claims, with such functions, functionalities and operations specified in the block diagram.

It will be understood that in some possible alternate implementations, the function, functionalities and operations noted in the blocks of a block diagram may occur out of the order noted in the block diagram. For example, the function noted in two blocks shown in succession can in fact be executed substantially concurrently or the functions noted in blocks can sometimes be executed in the reverse order, depending upon the function, functionalities and operations involved. Therefore, the embodiments of methods presented and described as a flowchart(s) in the form of a block diagram in the present application are provided by way of example in order to provide a more complete understanding of the disclosed subject matter. The disclosed flow and concomitantly the method(s) performed as recited in the accompanying claims are not limited to the functions, functionalities and operations illustrated in the block diagram and/or logical flow presented herein. Alternative embodiments are contemplated in which the order of the various functions, functionalities and operations may be altered and in which sub-operations described as being part of a larger operation may be performed independently or performed differently than illustrated or not performed at all.

Although some of the drawings may illustrate a number of operations in a particular order, functions, functionalities and/or operations which are not now known to be order dependent, or become understood to not be order dependent, may be reordered and other operations may be combined or broken out. While some reordering or other groupings may have been specifically mentioned in the present application, others will be or may become apparent to those of ordinary skill in the art and so the disclosed subject matter does not present an exhaustive list of alternatives. It should also be recognized that the aspects of the disclosed subject matter may be implemented in parallel or seriatim in hardware, firmware, software or any combination(s) thereof co-located or remotely located, at least in part, from each other, e.g., in arrays or networks of computing devices, over interconnected networks, including the Internet, and the like.

The disclosed subject matter is described in the present application with reference to one or more specific exemplary embodiments thereof. Such embodiments are provided by way of example only. It will be evident that various modifications may be made to the disclosed subject matter without departing from the broader spirit and scope of the disclosed subject matter as set forth in the appended claims. The specification and drawings are, accordingly, to be regarded in an illustrative sense for explanation of aspects of the disclosed subject matter rather than a restrictive or limiting sense. Numerous variations, changes, and substitutions will now occur to those skilled in the art without departing from the disclosed subject matter. It should be understood that various alternatives to the embodiments of the disclosed subject matter described herein may be employed in practicing the disclosed subject matter. It is intended that the following claims define the scope of the disclosed subject matter and that methods and structures within the scope of these claims and their equivalents be covered thereby.

It will be understood that the disclosed subject matter may comprise a fitness management method and apparatus which may comprise collecting food intake information for actual or expected food intake of a user over a first period of time and converting the food intake information into food intake units for the first period of time; collecting activity information for actual or expected activity by the user over the first period of time and converting the food intake information into food intake units for the user for the first period of time; collecting weight information representing a change in weight of the user over the first period of time; calculating, via a computing device, a calculated intrinsic metabolic rate for the user for the first period of time; collecting food intake information for actual or expected food intake of a user over a second period of time and converting the food intake information into food intake units for the second period of time; collecting activity information for actual or expected activity of a user over the second period of time and converting the activity information into activity units for the second period of time; calculating, via the computing device, a predicted change in weight for the second period of time based upon the calculated intrinsic metabolic rate for the user over the first period of time; collecting weight information representing an actual change in weight of the user over the second period of time; comparing the predicted change in weight for the second period of time to the actual change in weight for the second period of time; determining, via the computing device, an updated calculated intrinsic metabolic rate for the user based at least in part upon the difference between the predicted change in weight for the second period of time and the actual change in weight for the second period of time. The method and apparatus may further comprise collecting food intake information for actual or expected food intake of a user over a third period of time and converting the food intake information into food intake units for the third period of time; collecting activity information for actual or expected activity of a user over the third period of time and converting the activity information into activity units for the third period of time; calculating, via the computing device, a predicted change in weight for the third period of time based upon the updated calculated intrinsic metabolic rate for the user over the first period of time; collecting weight information representing an actual change in weight of the user over the second period of time; further updating, via the computing device, the updated calculated intrinsic metabolic rate for the user based at least in part upon the difference between the predicted change in weight for the third period of time and the actual change in weight for the third period of time. The method and apparatus may further comprise: displaying, via the computing device, at least one of an accumulation of food intake units and an accumulation of activity units over at least one of the first period of time, the second period of time and the third period of time. The apparatus and method may further comprise dividing the first period of time into a selected number of first sub-time periods; collecting food intake information for actual or expected food intake of the user over each of the first sub-time periods during the first period of time and converting the food intake information into food intake units for each of the first sub-time units during the first period of time; collecting activity information for actual or expected activity by the user over each of the first sub-time periods and converting the activity information into activity units for the user for each of the sub-time periods during the first period of time; collecting weight information representing a change in weight of the user over at least a last of the first sub-time periods and a first of the first sub-time periods to determine a change in weight of the user over the first period of time; dividing the second period of time into a selected number of second sub-time periods; collecting food intake information for actual or expected food intake of the user over each of the second sub-time periods during the second period of time and converting the food intake information into food intake units for each of the second sub-time units during the second period of time; collecting activity information for actual or expected activity by the user over each of the second sub-time periods and converting the activity information into activity units for the user for each of the second sub-time periods during the second period of time; collecting weight information representing a change in weight of the user over at least a last of the second sub-time periods to determine a change in weight of the user over the second period of time. The method and apparatus may further comprise dividing the third period of time into a selected number of third sub-time periods; collecting food intake information for actual or expected food intake of the user over each of the third sub-time periods during the third period of time and converting the food intake information into food intake units for each of the third sub-time periods during the third period of time; collecting activity information for actual or expected activity by the user over each of the third sub-time periods and converting the activity information into activity units for the user for each of the third sub-time periods during the third period of time; and collecting weight information representing a change in weight of the user over at least a last of the third sub-time periods to determine a change in weight of the user over the third period of time. The method and apparatus may further comprise determining an updated calculated intrinsic metabolic rate for the user based at least in part upon the difference between the predicted change in weight for the second period of time and the actual change in weight for the second period of time and determining a further updated calculated intrinsic metabolic rate for the user based at least in part upon the difference between the predicted change in weight for the second period of time and the actual change in weight for the second period of time. A machine readable medium storing instructions that, when executed by a computing device cause the computing device to perform a fitness management method is disclosed in which the method may comprising collecting food intake information for actual or expected food intake of a user over a first period of time and converting the food intake information into food intake units for the first period of time; collecting activity information for actual or expected activity by the user over the first period of time and converting the food intake information into food intake units for the user for the first period of time; collecting weight information representing a change in weight of the user over the first period of time; calculating a calculated intrinsic metabolic rate for the user for the first period of time; collecting food intake information for actual or expected food intake of a user over a second period of time and converting the food intake information into food intake units for the second period of time; collecting activity information for actual or expected activity of a user over the second period of time and converting the activity information into activity units for the second period of time; calculating a predicted change in weight for the second period of time based upon the calculated intrinsic metabolic rate for the user over the first period of time; collecting weight information representing an actual change in weight of the user over the second period of time; comparing the predicted change in weight for the second period of time to the actual change in weight for the second period of time; determining an updated calculated intrinsic metabolic rate for the user based at least in part upon the difference between the predicted change in weight for the second period of time and the actual change in weight for the second period of time.

The system and method may comprise a food intake information and weight information input unit; an activity information collection and input unit separate from the food intake information and weight information input unit and adapted to move with a portion a body of the user. At least one of the food intake information and weight information input unit and the activity information collection and input may comprise the computing device. The system and method may comprise the food information and weight information input unit comprising a portable user device having a touch screen display. The system and method may comprise the activity information input unit comprising an accelerometer for detecting activity repetitions. At least one of the food intake information and weight information input unit and the activity input unit the computing device may be configured to assign weighted values to each activity repetition according to one of the type and intensity of the activity and at least one of the repetitions detected. The system and method may comprise the food intake information input and weight information input unit further comprising the computing device configured to display a prediction of fitness performance based at least in part on a current metabolic rate for the user. The current metabolic rate may be computed by the computing device based on a difference between a predicted change in weight for a selected period of time and an actual measured change in weight for the selected period of time. The displayed prediction may comprise a graphical fitness prediction chart including perhaps a graphical fitness prediction chart.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Determination of Quality of Sleep

For the first two weeks of use, the program associated with the sleep activity monitoring mode counts how many movements there are during the "going to bed" period. A plot of the ratio of expected versus observed number of counts is generated, and is displayed as a percentage of expected versus observed on the sleep Arc. The percentages are weighted to exclude variances that could be explained by transient events such that outlier observations are excluded from the calculations of the Arc calculations. The counts are weighted by an algorithm such that more movement does not affect the Arc as much as less movement. This is based upon studies of sleep and non-sleep associated movements and their implications in assessing the restfulness of the "going to bed" period.

During the first two weeks, it is not known what number of counts represent a restful or agitated "going to bed" period for a particular user because reference data, other than that collected by the described invention (i.e., number of counts recorded on average for a particular user) is not known. The program associated with the sleep activity monitoring mode then looks for variance in the number of counts. Without being bound by theory, more counts would be indicative of a less restful "going to bed" period, while fewer counts would be indicative of a more restful "going to bed" period.

When a particular user selects the sleep activity monitoring mode, the directionality in the number of counts is tracked, recorded and compared to the fitness and health score in the Health Quotient. Without being bound by theory, it is believed that as the Health Quotient improves into the healthy zone or the fit zone, the "going to bed" period should become more restful. If the "going to bed" period does not become more restful, it may be indicative of a sleep dysfunction. The program associated with the sleep activity mode will announce to the particular user that there is a possible sleep disturbance. This assessment is derived from an analysis of the particular user's 'going to bed" counts referenced against the user's individual Heath Quotient.

The described invention is also able to determine the effect of the amount and types of exercise, caffeine, alcohol and food choices on the restfulness of a particular user's "going to bed" period. These behaviors are time stamped to further indicate their effects, given their proximity to the user's "going to bed" period. The user can query the program to search for the known triggers of a less restful "going to bed" period.

Without being bound by theory, the number and pattern of counts recorded in the sleep activity mode may be used in the actual diagnosis of a sleep disorder. For example, night terrors may have episodic but a prolonged number of counts with each episode; sleep apnea may be brief but frequent episodes of increased movement distributed equally through the night; restless leg syndrome activity may be of high volume but short durations sporadically through the night.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method for instantaneously and continuously assessing real time energy balance for fitness management comprising, in order:
    (a) collecting food intake information for actual or expected food intake of a user over a specified period of time and contemporaneously converting the food intake information into food intake energy units for the first period of time, wherein the food intake units are based on relative energy content of one food compared to another without relying on standard caloric values;
    (b) collecting by a device activity information for actual or expected activity by the user over the specified period of time and contemporaneously converting the activity information into energy units for the user for the first period of time, wherein the collecting for actual activity is achieved by wireless transmission by a motion sensor and the motion sensor is a programmable accelerometer, the functional status of which is altered by:
        (i) positioning the accelerometer inside an engineered magnetic environment;
        (ii) collecting deflections of the accelerometer during the activity in various positions inside the engineered environment such that it records motion associated with one type of activity while excluding movement characteristic of another form of activity;
        (iii) applying a multiplier to the accelerometer deflections collected in (ii) to assign a weighted value indicative of the level of effort exerted during the activity;
        (iv) saving deflections from each type of movement such that deflection counts are segregated by activity type and determining the amount of relative energy expended by the user during any given time period in the activity type;
        (v) transferring deflection counts and relative energy expended to a device; and
        (vi) processing the deflection counts and relative energy expended for display by the device;
    (c) instantaneously deriving, via a computing device, a calculated currently determined constant that reflects efficiency, which is a rate at which the user extracts energy from the food units that can be referenced against predicted and actual changes in weight, wherein the constant is a surrogate for intrinsic metabolic rate;
    (d) instantaneously calculating by an algorithm from the calculated currently determined constant in (c) a predicted energy balance for the user, by:
        1. calculating a ratio of an amount of activity units expected divided by an amount of activity observed;
        2. calculating a ratio of an amount of food units expected divided by an amount of food units observed;
        3. weighting the ratio in (a) against the ratio in (b) according to goals of the user; and
        4. modifying the weighted ratio in (3) by a rate at which the user performs the activity/work
    (e) instantaneously predicting a change in weight from the predicted energy balance; and
    (f) determining fitness level of the user based on the efficiency of energy consumption.

2. The method according to claim 1, wherein the change in weight is displayable either as a numeric weight or as a colored dot display system.

3. The method according to claim 2, wherein the colored dot display system comprises:
    (a) a red dot representing weight gain other than muscle;
    (b) a green dot representing muscle growth or weight loss; and
    (c) a yellow dot representing no change in fat/muscle ratios.

4. The method according to claim 1, wherein the deflection counts in (d) are segregated by activity type in a processor.

5. The method according to claim 1, wherein positioning the accelerometer inside the engineered magnetic environment initiates a programming change to alter the functional status of the accelerometer into activity monitoring modes.

6. The method according to claim 5, wherein the activity monitoring modes are selected from the group consisting of a standard mode (S), a running/jogging mode (A+), a bicycle mode (A), a weight lifting/resistance training/yoga mode (W+), an aerobic-based gym equipment mode (W) and a sleep activity mode.

7. The method according to claim 6, wherein the standard mode (S) comprises routine daily activity.

8. The method according to claim 1, wherein the type of activity is selected from the group consisting of aerobic and non-aerobic.

9. The method according to claim 8, wherein the aerobic activity is selected from the group consisting of walking, jogging, running, biking, tennis, basketball, soccer circuit training and elliptical training.

10. The method according to claim 8, wherein the non-aerobic activity is selected from the group consisting of weight lifting, yoga, Pilates and resistance training.

11. The method according to claim 1, wherein the accelerometer is a triaxial accelerometer.

12. The method according to claim 1, wherein the engineered magnetic environment is a magnetic field.

13. The method according to claim 12, wherein the magnetic field is created by magnets.

14. The method according to claim 13, wherein the magnets are contained within a receptacle.

15. The method according to claim 14, wherein the receptacle is pouch.

16. The method according to claim 14, wherein the receptacle is a pocket.

17. The method according to claim 14, wherein the receptacle is connected to a means for attaching the accelerometer to a user.

18. The method according to claim 1, wherein when the type of activity is sleep, the method further comprises a method for measuring quality of sleep comprising:
 (i) assigning a time period in which the user is going to bed;
 (ii) collecting deflections of the accelerometer during the assigned time period of (i);
 (iii) transferring the deflection counts collected in (ii) corresponding to sleep activity to a device;
 (iv) ending the time period assigned in (i); and
 (v) processing the deflection counts for display by the device,
wherein an increase in accelerometer deflections recorded compared to an average of accelerometer deflections recorded is indicative of a sleep disorder.

19. The method according to claim 18, wherein the sleep disorder is selected from the group consisting of sleep apnea, insomnia and restless leg syndrome.

20. The method according to claim 19, wherein the sleep disorder is sleep apnea.

21. The method according to claim 2, wherein when the type of activity is sleep, the method further comprises a method for determining an increased physiological benefit during sleep comprising:
 (i) assigning a time period in which the user is going to bed;
 (ii) collecting deflections of the accelerometer during the assigned time period of (i);
 (iii) transferring the deflection counts collected in (ii) corresponding to sleep activity to a device;
 (iv) ending the time period assigned in (i); and
 (v) processing the deflection counts for display by the device,
wherein no change or a decrease in accelerometer deflections recorded compared to an average of accelerometer deflections recorded is indicative of an increased physiological benefit during sleep.

22. The method according to claim 21, wherein the increased physiological benefit is an increase in interstitial space in brain.

23. The method according to claim 21, wherein the increased physiological benefit is an increase in convective exchange of cerebrospinal fluid (CSF) and interstitial fluid (ISF) in brain.

24. The method according to claim 21, wherein the increased physiological benefit is an increased rate of clearance from brain of a protein linked to neurodegenerative disease.

25. The method according to claim 24, wherein the protein is selected from the group consisting of β-amyloid (Aβ), α-synuclein and tau.

26. The method according to claim 1, wherein the information used to determine weight gain other than muscle, muscle growth or weight loss, or no change in fat/muscle ratios, is integrated into multiple parameters that form a health quotient displayed by the device as a single point on a scale ranging from fit to healthy to unhealthy to at risk.

27. A non-transitory machine readable medium storing instructions that, when executed by a computing device, cause the computing device to perform a method for instantaneously and continuously assessing real time energy balance for fitness management, comprising:
 (a) collecting food intake information for actual or expected food intake of a user over a specified period of time and contemporaneously converting the food intake information into food intake energy units for the specified period of time, wherein the food intake units are based on relative energy content of one food compared to another without relying on standard caloric values;
 (b) collecting by a device activity information for actual or expected activity by the user over the specified period of time and contemporaneously converting the activity information into activity energy units for the user for the specified period of time, wherein the collecting for actual activity is achieved by wireless transmission by a motion sensor and the motion sensor is a programmable accelerometer, the functional status of which is altered by:
  (i) positioning the accelerometer inside an engineered magnetic environment;
  (ii) collecting deflections of the accelerometer during the activity in various positions inside the engineered environment such that it records motion associated with one type of activity while excluding movement characteristic of another form of activity;
  (iii) applying a multiplier to the accelerometer deflections collected in (ii) to assign a weighted value indicative of the level of effort exerted during the activity;
  (iv) saving deflections from each type of movement such that deflection counts are segregated by activity type and determining the amount of relative energy expended by the user during any given time period in the activity type;
  (v) transferring deflection counts and relative energy expended to a device; and
  (vi) processing the deflection counts and relative energy expended for display by the device;
 (c) instantaneously deriving, via a computing device, a calculated currently determined constant that reflects efficiency, which is a rate at which the user extracts energy from the food units that can be referenced against predicted and actual changes in weight, wherein the constant is a surrogate for intrinsic metabolic rate (d) instantaneously calculating by an algorithm from the calculated currently determined constant in (c) a predicted energy balance for the user, by:
  (i) calculating a ratio of an amount of activity units expected divided by an amount of activity observed;
  (ii) calculating a ratio of an amount of food units expected divided by an amount of food units observed;
  (iii) weighting the ratio in (a) against the ratio in (b) according to goals of the user; and (iv) modifying the weighted ratio in (iii) by a rate at which the user performs the activity/work;

(e) instantaneously predicting a change in weight from the predicted energy balance; and (f) determining fitness level of the user based on the efficiency of energy consumption.

28. A system for instantaneously and continuously assessing real time energy balance for fitness management comprising:
  a computing device configured to:
  (a) collect food intake information for actual or expected food intake of a user over a specified period of time and contemporaneously converting the food intake information into food intake units for the specified period of time, wherein the food intake units are based on relative energy content of one food compared to another without relying on standard caloric values;
  (b) collect by a device activity information for actual or expected activity by the user over the specified period of time and contemporaneously converting the activity information into activity units for the user for the first period of time, wherein the collecting for actual activity is achieved by wireless transmission by a motion sensor and the motion sensor is a programmable accelerometer, the functional status of which is altered by:
    (i) positioning the accelerometer inside an engineered magnetic environment;
    (ii) collecting deflections of the accelerometer during the activity in various positions inside the engineered environment such that it records motion associated with one type of activity while excluding movement characteristic of another form of activity;
    (iii) applying a multiplier to the accelerometer deflections collected in (ii) to assign a weighted value indicative of the level of effort exerted during the activity;
    (iv) saving deflections from each type of movement such that deflection counts are segregated by activity type and determining the amount of relative energy expended by the user during any given time period in the activity type;
    (v) transferring deflection counts and relative energy expended to a device; and
    (vi) processing the deflection counts and relative energy expended for display by the device;
  (c) instantaneously derive, via a computing device, a calculated currently determined constant that reflects efficiency, which is a rate at which the user extracts energy from the food units that can be referenced against predicted and actual changes in weight, wherein the constant is a surrogate for intrinsic metabolic rate
  (d) instantaneously calculate by an algorithm from the calculated currently determined constant in (c) a predicted energy balance for the user, by:
    (i) calculating a ratio of an amount of activity units expected divided by an amount of activity observed;
    (ii) calculating a ratio of an amount of food units expected divided by an amount of food units observed;
    (iii) weighting the ratio in (a) against the ratio in (b) according to goals of the user; and (iv) modifying the weighted ratio in (iii) by a rate at which the user performs the activity/work;
  (e) instantaneously predict a change in weight from the predicted energy; and
  (f) determine fitness level of the user based on the efficiency of energy consumption.

* * * * *